United States Patent [19]

Tahara et al.

[11] Patent Number: 5,593,988
[45] Date of Patent: Jan. 14, 1997

[54] THERAPEUTIC AGENT FOR OSTEOPOROSIS AND DIAZEPINE COMPOUND

[75] Inventors: Tetsuya Tahara; Minoru Moriwaki, both of Chikujo-gun; Kenji Chiba, Iruma; Shunichi Manabe; Masanori Shindo, both of Takatsuki; Takashi Nakagawa; Takeshi Nakamura, both of Takatsuki, all of Japan

[73] Assignees: Yoshitomi Pharmaceutical Industries, Ltd., Osaka; Japan Tobacco, Inc., Tokyo, both of Japan

[21] Appl. No.: 211,572

[22] PCT Filed: Oct. 12, 1992

[86] PCT No.: PCT/JP92/01325

§ 371 Date: Aug. 2, 1994

§ 102(e) Date: Aug. 2, 1994

[87] PCT Pub. No.: WO93/07129

PCT Pub. Date: Apr. 15, 1993

[30] Foreign Application Priority Data

Oct. 11, 1991 [JP] Japan ............................. 3-327954

[51] Int. Cl.$^6$ .................... A61K 31/55; C07D 495/14; C07D 498/04; C07D 495/04
[52] U.S. Cl. .................... 514/219; 514/220; 514/211; 540/555; 540/560; 540/548; 540/546
[58] Field of Search ................ 540/555, 560; 514/220, 219

[56] References Cited

U.S. PATENT DOCUMENTS

| | | | |
|---|---|---|---|
| 3,872,089 | 3/1975 | Hromatka et al. | 260/239.3 T |
| 4,333,944 | 6/1982 | Weber et al. | 424/269 |
| 4,959,361 | 9/1990 | Walser | 514/220 |
| 5,286,858 | 2/1994 | Moriwaki et al. | 540/560 |

FOREIGN PATENT DOCUMENTS

| | | |
|---|---|---|
| 0403185 | 12/1990 | European Pat. Off. . |
| 2-138272 | 5/1990 | Japan . |
| 2-300124 | 12/1990 | Japan . |
| 3-47162 | 2/1991 | Japan . |

OTHER PUBLICATIONS

Okano, K. et al. *Chemical Abstract* 113:212028 (1990).
Tahara, T. et al. *Chemical Abstract* 80:133443 (1974).
Moriwaki, M. et al. *Chemical Abstract* 110:173267 (1989).
Moriwaki, M. et al. *Chemical Abstract* 112:216937 (1990).
Naka, Y. et al. *Chemical Abstract* 111:214514 (1989).
Moriwaki, M. et al. *Chemical Abstract* 112:77237 (1990).
Casals –Stenzel, J. et al. *Chemical Abstract* 105:146244 (1986).
Braquet, P. et al. *Chemical Abstract* 114:122431 (1991).
Walser, A. *Chemical Abstract* 114:143456 (1991).
Tahara, T. et al. *Chemical Abstract* 109:211096 (1988).
Braquet, P. et al. *Chemical Abstract* 116:128977 (1992).
Weber, K. H. et al. *Chemical Abstract* 115:114558 (1991).
Nakanishi, M. et al. *Chemical Abstract* 78:84416 (1973).
Nakanishi et al., "Thienodiazepine Derivatives", *Chemical Abstracts*, vol. 82, No. 9, 1975, Abstract No. 57752u (and JP-A-7411392)**.

Primary Examiner—Cecilia Tsang
Assistant Examiner—King Lit Wong
Attorney, Agent, or Firm—Wenderoth, Lind & Ponack

[57] ABSTRACT

A therapeutic agent for osteoporosis, comprising an azepine compound of the formula

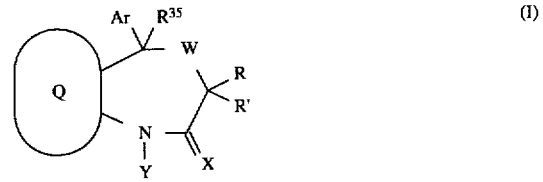

wherein each symbol is as defined in the specification, or a pharmaceutically acceptable salt thereof as an active ingredient, a method for treating osteoporosis comprising administering said compound and a use of said compound for the production of a therapeutic agent for osteoporosis. The compounds of the formula (I) have superior bone resorption-inhibitory activity and act to reduce the increased amount of calcium in blood serum, which is caused by bone resorption. Accordingly, these compounds are usable as pharmaceutical agents to effectively inhibit bone resorption, to prevent decrease of bone mass and to prevent or suppress the increase of calcium amount in blood serum which is caused by the progress of bone resorption, with regard to Paget's disease, hypercalcemia, osteoporosis and so on in which the progress of bone resorption is considered to be deeply associated with the symptom, and to the symptoms of progressing bone resorption (development into osteoporosis) along with inflammatory joint diseases such as rheumatoid arthritis.

7 Claims, No Drawings

THERAPEUTIC AGENT FOR OSTEOPOROSIS AND DIAZEPINE COMPOUND

This application is a 371 of PCT/JP92/01325, filed Oct. 12, 1992 and published as WO93/07129 Apr. 15, 1993.

TECHNICAL FIELD

The present invention relates to a therapeutic agent for osteoporosis containing, as an active ingredient, a certain azepine compound having superior bone resorption-inhibitory activity, a novel diazepine compound, a method for treating osteoporosis and use of said compound.

BACKGROUND ART

The osteoporosis is a syndrome which develops a symptom wherein a bone mass per unit volume is unusually decreased without causing any change in the chemical composition (ratio between organic substance and mineral substance) of the ossein per se and physiologically characterized by a decrease in protein, calcium and phosphorus in the bone.

The decrease in bone mass as a symptom includes that caused by physiological aging. Accordingly, the definition of the disease will be a remarkable decrease in bone mass which is greater than that caused by the physiological aging and the manifestation of clinical symptoms such as dorsolumbar pain, pathologic fracture, vertebral deformation and the like.

The osteoporosis proceeds with aging and generally damages vertebra and causes dorsolumbar pain and shortening of the height. In a very advanced case, long bone is also damaged to sometimes cause fracture. The femoral fractures seen in old people are said to be mostly due to senile osteoporosis.

The causes of the osteoporosis are diverse and include abnormal internal secretion inclusive of menopause, nutritional disorder and so on. The vitamin D preparations, calcium preparations, calcitonin preparations, bisphosphonate preparations and so on conventionally used for treating osteoporosis suffer from limitation on administration targets and unconclusive effects. As regards female hormone preparations, its dependable effects are associated with severe side effects such as genital cancer caused by a long-term use of the preparation.

Hence, the development of a therapeutic agent for osteoporosis, having reliable effects and high safety is strongly demanded.

In recent years, thionaphthene-2-carboxylic acid derivative and 3-phenyl-4H-1-benzopyran-4-one derivative (isoflavone derivative) having a completely different chemical structure from the aforementioned preparations have been reported to have bone resorption-inhibitory activity and to be useful as therapeutic agents for treating osteoporosis (A. J. Johannesson et al, Endocrinology, 117, P. 1508, EP-A-135172, EP-A-136569, EP-A-146921, U.S. Pat. No. 4,644,012).

As the derivative having bone resorption-inhibitory activity, (cycloalkylamino)methylenebis(phosphonic acid) derivative (U.S. Pat. No. 4,970,335), heterocyclic bisphosphonic acid derivative (U.S. Pat. No. 4,990,503) and benzofuroquinoline derivative (EP-A-357172) have been reported.

As the compounds having a diazepine skeleton, known are benzodiazepine compounds, thienodiazepine compounds, benzotriazolodiazepine compounds, benzimidazolodiazepine compounds and thienotriazolodiazepine compounds, having antianxiety, sedative and muscle-relaxing actions. Specific examples are bromazepam, clotiazepam, diazepam, flunitrazepam, flurazepam, lorazepam, medazepam, nitrazepam, oxazepam, azinazolam, alprazolam, brotizolam, estazolam, etizolam, midazolam and triazolam.

In addition, certain diazepine compounds such as devazepide and L-365260 are known to have cholecystokinin (CCK) antagonistic action or gastrin antagonistic action (Japanese Patent Unexamined Publication Nos. 63666/1986, 238069/1988 and 223290/1991 and WO89/05812).

As the compounds having a platelet activating factor (PAF)-antagonistic action and expected to be an antiasthma agent and a circulatory drug, known are thienotriazolodiazepine compounds such as 4-(2-chlorophenyl)-2-(2-(4-isobutylphenyl)ethyl)-6,9-dimethyl-6H-thieno[3,2-f][1,2,4]triazolo[4,3-a][1,4]diazepine, 3-(4-(2-chlorophenyl)-6,9-dimethyl-6H-thieno[3,2-f][1,2,4]-triazolo[4,3-a][1,4] diazepin-2-yl)propionic morpholide, 4-(3-(4-(2-chlorophenyl)-9-methyl-6H-thieno[3,2-f][1,2,4]triazolo-[4, 3-a][1,4]diazepin-2-yl)propionyl)morpholine, 4-((6-(2-chlorophenyl)-8,9-dihydro-1-methyl-4H,7H-cyclopenta[4, 5]thieno-[3,2-f][1,2,4]triazolo[4,3-a][1,4]diazepin-8-yl)carbonyl)-morpholine, 6-(2-chlorophenyl)-8,9-dihydro-1-methyl-N,N-dipropyl-4H,7H-cyclopenta[4,5]thieno[3,2-f][1,2,4]triazolo-[4,3-a][1,4]diazepine-8-carboxamide, 6-(2-chlorophenyl)-3-cyclopropanecarbonyl-8,11-dimethyl-2,3, 4,5-tetrahydro-8H-pyrido[4',3':4,5]thieno[3,2-f][1,2,4] triazolo[4,3-a][1,4]-diazepine, and optical isomers thereof (Japanese Patent Unexamined Publication Nos. 87623/1986, 87684/1986, 176591/1986, 181282/1987, 240686/1987, 33382/1988, 35574/1988, 197484/1989, 98835/1990, 79185/1989, 79186/1989, 85978/1989, 156982/1989, 256681/1990, 49787/1990, 191281/1990, 243691/1990, 256682/1990, 275883/1990, 286684/1990, 289582/1990, 145437/1991, 215489/1991, 264588/1991, 264589/1991, 66585/1992).

As stated above, the therapeutic agents for osteoporosis so far reported do not necessarily exhibit satisfactory effects and the development of a compound having superior action is awaited.

Accordingly, an object of the present invention is to provide a superior therapeutic agent for osteoporosis. Another object of the present invention is to provide a novel compound to be used as an active ingredient of a therapeutic agent for osteoporosis.

A still another object of the present invention is to provide a method for treating osteoporosis and use for the treatment of osteoporosis.

DISCLOSURE OF THE INVENTION

The present inventors have conducted intensive studies of bone resorption-inhibitory activity of certain azepine compounds in an attempt to develop a superior therapeutic agent for osteoporosis and found that the azepine compounds show superior action, which resulted in the completion of the invention.

Accordingly, the present invention relates to a therapeutic agent for osteoporosis, comprising an azepine compound of the formula

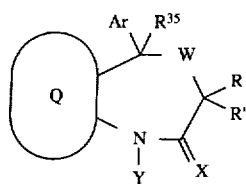 (I)

or a pharmaceutically acceptable salt thereof as an active ingredient, a method for treating osteoporosis comprising administering said compound and a use of said compound for the production of a therapeutic agent for osteoporosis.

In the above formula, each symbol is as defined in the following.

Ar means aryl or heteroaryl;

X is an oxygen atom or a sulfur atom;

Y is hydrogen, alkyl, alkenyl, alkynyl, —(CH$_2$)aCOOR$^1$ wherein R$^1$ is hydrogen, alkyl, aryl or aralkyl and a is an integer of 1 to 6, —(CH$_2$)a-cycloalkyl wherein a is an integer of 1 to 6, —(CH$_2$)aN(R$^2$)(R$^3$) wherein a is an integer of 1 to 6 and R$^2$ and R$^3$ are the same or different and each is hydrogen, alkyl or aralkyl, or form, together with the adjacent nitrogen atom, a heterocycle, —(CH$_2$)bCON(R$^{41}$)(R$^{42}$) wherein b is 0 or an integer of 1 to 6, and R$^{41}$ and R$^{42}$ are the same or different and each is hydrogen, alkyl, aryl or aralkyl, or form, together with the adjacent nitrogen atom, a heterocycle, —(CH$_2$)aCN wherein a is an integer of 1 to 6, or —(CH$_2$)aCR$^4{}_3$ wherein a is an integer of 1 to 6 and R$^4$ is halogen, or X and Y combinedly form =N—N=C(R$^6$)—, =N—C(R$^5$)=C(R$^6$)—, =C(R$^5$)—N=C(R$^6$)—, =N—O—CO— or =N—N(R$^5$)—CO— wherein R$^5$ and R$^6$ are each hydrogen, halogen, alkyl, alkenyl, alkynyl, cycloalkyl, cycloalkylalkyl, aryl, heteroaryl, aralkyl, heteroarylalkyl, aryloxyalkyl, —(CH$_2$)aCOOR$^7$ wherein a is an integer of 1 to 6 and R$^7$ is hydrogen, alkyl, alkenyl or aralkyl, or —(CH$_2$)aNHCOR$^{43}$ wherein a is an integer of 1 to 6 and R$^{43}$ is alkyl or aralkyl;

W is —N(R$^{36}$)— wherein R$^{36}$ is hydrogen or forms a bond with R$^{35}$, —O— or —S—;

R$^{35}$ is hydrogen or forms a bond with R$^{36}$;

R is hydrogen, alkyl, haloalkyl, aryl, heteroaryl, aralkyl, heteroarylalkyl or a group of the formula selected from —(CH$_2$)bN(R$^8$)(R$^9$)  (1)

—(CH$_2$)bOR$^{10}$  (2)

—(CH$_2$)bN(R$^{10}$)CN(R$^{11}$)(R$^{12}$)  (3)
 $\overset{Z}{\|}$

—(CH$_2$)bN(R$^{10}$)COR$^{a11}$  (4)

—(CH$_2$)bN(R$^{10}$)SO$_2$R$^{44}$  (5)

—(CH$_2$)bN(R$^{10}$)COOR$^{45}$  (6)

—(CH$_2$)bOCN(R$^{11}$)(R$^{12}$)  (7)
 $\overset{Z}{\|}$

—(CH$_2$)bOCOR$^{46}$  (8)

—(CH$_2$)bCON(R$^{47}$)(R$^{48}$)  (9)

—(CH$_2$)bOSO$_2$R$^{44}$  (10)

—(CH$_2$)bCOR$^{49}$  (11)

—(CH$_2$)bS(O)nR$^{11}$  (12)

—CON(R$^{10}$)OR$^8$  (13)

—CON(R$^{10}$)N(R$^{10}$)CR$^{a11}$  (14)
 $\overset{Z}{\|}$

—CON(R$^{10}$)N(R$^{10}$)SO$_2$R$^{a11}$  (15)

—N(R$^{10}$)CN(R$^{10}$)COR$^{a11}$  (16)
 $\overset{Z}{\|}$

—(R$^{10}$)CN(R$^{10}$)SO$_2$R$^{a11}$  (17)
 $\overset{Z}{\|}$

—CON(R$^{10}$)N(R$^{10}$)(R$^{11}$)  (18)

—(CH$_2$)bN(R$^{10}$)COCON(R$^{11}$)(R$^{12}$)  (19)

and

—(CH$_2$)aCOOR$^1$  (20)

wherein b is 0 or an integer of 1 to 6, Z is an oxygen atom or sulfur atom, R$^8$ and R$^9$ are the same or different and each is hydrogen, alkyl, aryl or aralkyl, R$^{10}$ is hydrogen, alkyl or aralkyl, R$^{11}$ and R$^{12}$ are the same or different and each is hydrogen, alkyl, cycloalkyl, cycloalkylalkyl, aryl, aralkyl, heteroaryl or heteroarylalkyl, R$^{a11}$ is alkyl, cycloalkyl, cycloalkylalkyl, aryl, aralkyl, heteroaryl or heteroarylalkyl, R$^{44}$ is alkyl, aryl, aralkyl, cycloalkyl or heteroaryl, R$^{45}$ is alkyl, aryl or aralkyl, R$^{46}$ is alkyl, alkenyl, alkynyl, cycloalkyl, cycloalkylalkyl, aryl, aralkyl, heteroaryl or heteroarylalkyl, R$^{47}$ and R$^{48}$ are the same or different and each is hydrogen, alkyl, acyl, aryl or aralkyl, R$^{49}$ is alkyl, aryl, aralkyl, heteroaryl or heteroarylalkyl, n is 0, 1 or 2, a is an integer of 1 to 6 and R$^1$ is hydrogen, alkyl, aryl or aralkyl;

R' is hydrogen or —COOR$^8$ wherein R$^8$ is hydrogen, alkyl, aryl or aralkyl, or R and R' combinedly form a spiro ring of the formula

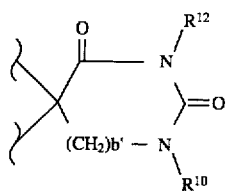

wherein b' is 0 or 1, R$^{10}$ is hydrogen, alkyl or aralkyl and R$^{12}$ is hydrogen, alkyl, cycloalkyl, cycloalkylalkyl, aryl, aralkyl, heteroaryl or heteroarylalkyl;

ring Q is a ring selected from

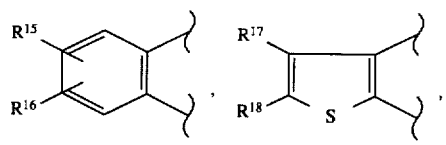

-continued

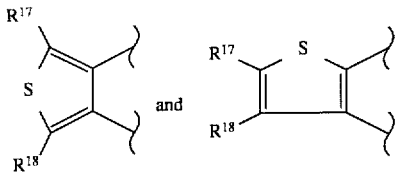

wherein $R^{15}$ and $R^{16}$ are the same or different and each is hydrogen, halogen, alkyl optionally substituted by halogen, alkoxy, nitro, amino, amino substituted by alkyl, cyclic amino, hydroxy, acyloxy, cyano, carbamoyl, carbamoyl substituted by alkyl, cyclic aminocarbonyl, carboxyl, alkoxycarbonyl or aralkyloxycarbonyl, aralkyl, aralkyl substituted by alkyl, alkoxy, nitro, amino, amino substituted by alkyl, cyclic amino, hydroxy, acyloxy, cyano, carbamoyl, carbamoyl substituted by alkyl, cyclic aminocarbonyl, carboxyl, alkoxycarbonyl or aralkyloxycarbonyl;

$R^{17}$ and $R^{18}$ are the same or different and each is hydrogen, halogen, alkyl, alkenyl, alkynyl, haloalkyl, alkoxy, nitro, amino, amino substituted by alkyl, cyclic amino, hydroxy, acyloxy, cyano, carbamoyl, carbamoyl substituted by alkyl, cyclic aminocarbonyl, carboxyl, alkoxycarbonyl, aralkyloxycarbonyl, cycloalkyl, alkylcarbonyl, a group of the formula $R^{19}$—A— wherein A is alkylene, alkenylene or alkynylene which may be substituted by 1 to 3 hydroxys and $R^{19}$ is alkoxy, nitro, amino, hydroxy, acyloxy, cyano, carboxyl, alkoxycarbonyl, aralkyloxycarbonyl, phenyl optionally substituted by 1 to 3 substituents (e.g. halogen, hydroxy, alkyl, alkoxy, aryl, aryloxy, aralkyl, aralkyloxy, alkenyl or alkynyl having 2 to 18 carbon atoms, which may be substituted by 1 to 3 hydroxys, aralkenyl or aralkynyl having alkenyl moiety or alkynyl moiety having 2 to 18 carbon atoms, which may be substituted by 1 to 3 hydroxys), a group of the formula $(R^{20})(R^{21})NCO$— or $(R^{20})(R^{21})N$—$SO_2$— wherein $R^{20}$ and $R^{21}$ are the same or different and each is hydrogen, aryl, aralkyl or straight- or branched chain alkyl, alkenyl or alkynyl which may be substituted by halogen, hydroxy, nitro, amino or substituted amino, or $R^{20}$ and $R^{21}$ may, together with the adjacent nitrogen atom, form a 3 to 7-membered ring which may be substituted by straight- or branched chain alkyl and may have, in the ring, nitrogen, oxygen or sulfur atom as a hetero atom (the additional nitrogen atom may be substituted by straight- or branched chain alkyl having 1 to 4 carbon atoms, aralkyl or diarylalkyl), a group of the formula $(R^{22})(R^{23})N$— wherein $R^{22}$ and $R^{23}$ are the same or different and each is hydrogen, straight- or branched chain alkyl, alkenyl or alkynyl, which may be substituted by halogen, hydroxy, amino, alkylamino, dialkylamino, cyclic amino or C-bonded heterocyclic group (carbons may be interrupted by nitrogen, oxygen or sulfur atom), straight- or branched chain alkylcarbonyl which may be mono- or di-substituted by hydroxy, halogen, amino, alkylamino, dialkylamino, cyclic amino or straight- or branched chain alkyl (this alkyl may be substituted by halogen or hydroxy), arylcarbonyl, arylsulfonyl, alkylsulfonyl, or $R^{22}$ and $R^{23}$ may form, together with the adjacent nitrogen atom, a saturated or unsaturated 3 to 7-membered ring which may be substituted by straight- or branched chain alkyl and may have, in the ring, nitrogen, oxygen or sulfur atom as a hetero atom (each additional nitrogen atom may be substituted by straight- or branched chain alkyl), a group of the formula

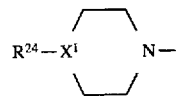

wherein $R^{24}$ is aryl, aralkyl, arylcarbonyl, a group of the formula

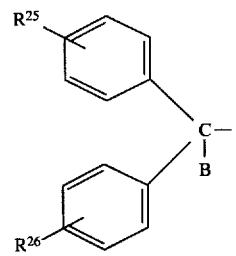

wherein $R^{25}$ and $R^{26}$ are the same or different and each is hydrogen, halogen, haloalkyl, amino, nitro, cyano, hydroxy, alkyl or alkoxy and B is hydrogen, hydroxy or esterified hydroxy, or alkyl having hydroxy and/or carbonyl and $X^1$ is CH or nitrogen atom, or a group of the formula

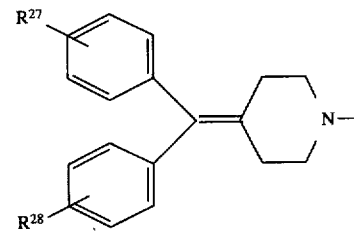

wherein $R^{27}$ and $R^{28}$ are the same or different and each is hydrogen, halogen, haloalkyl, amino, nitro, cyano, hydroxy, alkyl or alkoxy, a group of the formula $R^{29}$—$(CH_2)_d$—C≡C— wherein $R^{29}$ is aryl or optionally hydrogenated heteroaryl and d is 0, 1 or 2, a group of the formula $R^{29}$—O—$(CH_2)_e$—C≡C— wherein $R^{29}$ is as defined above and e is 1 or 2, or a group of the formula

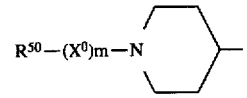

wherein $X^0$ is —OCO—, —CO— or —N($R^{51}$)CO— where $R^{51}$ is hydrogen or alkyl, m is 0 or 1, $R^{50}$ is alkyl, alkynyl, 2-phenylethynyl, 2-thienylsulfonyl, —(CH$_2$)aCN where a is an integer of 1 to 6, —(CH$_2$)b-R$^{52}$ where b is 0 or an integer of 1 to 6 and R$^{52}$ is cycloalkyl, morphlino, thienyl, alkoxy, aryl, imidazolyl or tetrahydropyranyl or —SO$_2$N(R$^{53}$)(R$^{54}$) where R$^{53}$ and R$^{54}$ are the same or different and each is hydrogen, alkyl, or R$^{53}$ and R$^{54}$, with the adjacent nitrogen atom, form a heterocycle, or adjacent R$^{17}$ and R$^{18}$ may combinedly form a saturated or unsaturated 5, 6 or 7-membered ring which is condensed to thiophene ring, said ring being optionally substituted by a substituent Ra$^{30}$ selected from hydrogen, halogen, alkyl, a group of the formula R$^{19}$—A— wherein each symbol is as defined above and a group of the formula (R$^{20}$)(R$^{21}$)NCO— or (R$^{20}$)(R$^{21}$)N—SO$_2$— wherein each symbol is as defined above, or R$^{17}$ and R$^{18}$ may combinedly form a 5, 6 or 7-membered hetero ring which may have oxygen, sulfur or —N(Rb$^{30}$)— as a hetero atom.

Examples of Rb$^{30}$ include hydrogen, alkyl, alkenyl, alkynyl, cycloalkyl, alkoxycarbonyl, alkanoyl, aroyl, cycloalkylcarbonyl, cycloalkoxycarbonyl, cycloalkylalkylcarbonyl, cycloalkylalkoxycarbonyl, cycloalkylaminocarbonyl, a group of the formula R$^{19}$—A— wherein each symbol is as defined above, a group of the formula (R$^{20}$)(R$^{21}$)NCO— wherein each symbol is as defined above, a group of the formula (R$^{20}$)(R$^{21}$)N—SO$_2$— wherein each symbol is as defined above, a group of the formula Ra$^{31}$—SO$_2$— wherein Ra$^{31}$ is alkyl, phenyl, phenyl substituted by halogen, alkyl, alkoxy, carboxy, alkylsulfonyl, alkylthio, haloalkyl or optionally substituted phenoxy, heteroaryl or naphthyl, a group of the formula

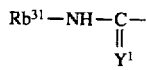

wherein Y$^1$ is oxygen atom or sulfur atom and Rb$^{31}$ is alkenyl, alkyl, cycloalkyl, aryl, aralkyl, heteroaryl, heteroarylalkyl, phenyl substituted by 1 to 3 substituents selected from alkyl, alkoxy, aryloxy, alkylsulfonyl, halogen and haloalkyl, quinolyl or sulfonyl substituted by phenyl, heteroaryl or naphthyl, or a group of the formula

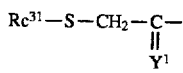

wherein Y$^1$ is oxygen atom or sulfur atom and Rb$^{31}$ is alkyl, phenyl substituted by phenyl, halogen, alkyl, alkoxy, haloalkyl or optionally substituted phenoxy, or heteroaryl.

In the above definitions, aryl, aryloxy, aryloxyalkyl, arylcarbonyl, arylsulfonyl, aralkyl, aralkyloxy, aralkyloxycarbonyl, aralkenyl, aralkynyl, diarylalkyl, heteroaryl and heteroarylalkyl may have, on the ring, 1 to 3 substituents selected from halogen, alkyl, alkoxy, haloalkyl, hydroxy, nitro, amino, cyano and acyloxy. Cycloalkyl of cycloalkyl, cyclo-alkylalkyl, cycloalkylcarbonyl, cycloalkylalkylcarbonyl, cycloalkoxycarbonyl, cycloalkylalkoxycarbonyl and cycloalkylaminocarbonyl may have 1 to 3 substituents selected from halogen, alkyl, alkoxy, haloalkoxy and aryl.

Furthermore, the present invention provides a diazepine compound of the formula

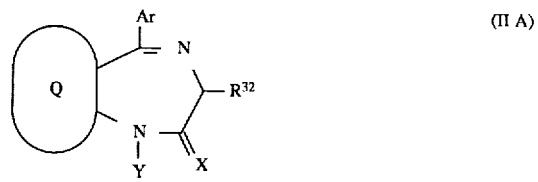

wherein R$^{32}$ is optionally substituted phenyl or optionally substituted phenylalkyl and other symbols are as defined above, a pharmaceutically acceptable salt thereof, a diazepine compound of the formula

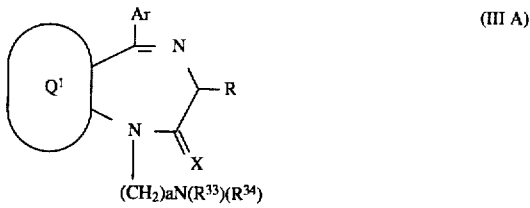

wherein a is an integer of 1 to 6, R$^{33}$ and R$^{34}$ are the same or different and each is alkyl or aralkyl or R$^{33}$ and R$^{34}$ may combinedly form a 5 to 7-membered ring which may have, in the ring, nitrogen, sulfur or oxygen atom, the ring Q$^1$ is

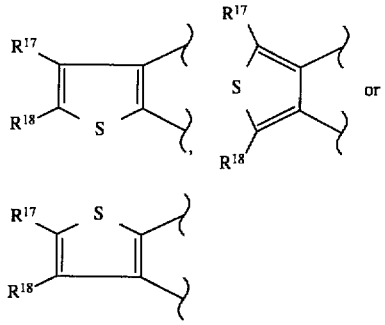

wherein R$^{17}$ and R$^{18}$ are as defined above, and other symbols are as defined above, and a pharmaceutically acceptable salt thereof.

In addition, the present invention provides a benzotriazolodiazepine compound of the formula

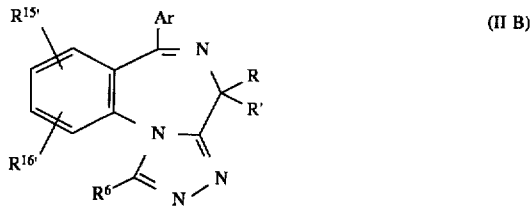

wherein R$^{15'}$ is alkyl or aralkyl having 8 to 15 carbon atoms, R$^{16'}$ is hydrogen and other symbols are as defined above, a pharmaceutically acceptable salt thereof, a benzotriazolodiazepine compound of the formula

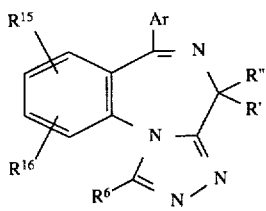
(III B)

wherein R" is a group of the formula selected from

—CON(R⁴⁷)(R⁴⁸)  (9')

—CON(R¹⁰)OR⁸  (13)

$$-CON(R^{10})N(R^{10})\overset{\overset{Z}{\|}}{C}Ra^{11}$$  (14)

$$-N(R^{10})\overset{\overset{Z}{\|}}{C}N(R^{10})CORa^{11}$$  (16)

$$-N(R^{10})\overset{\overset{Z}{\|}}{C}N(R^{10})SO_2Ra^{11}$$  (17)

—CON(R¹⁰)N(R¹⁰)(R¹¹)  (18)

and

—N(R¹⁰)CON(R¹⁰)Py  (21)

wherein Py is optionally substituted pyridyl and other symbols are as defined above, R' is hydrogen or R" and R' may combinedly form a spiro ring of the formula

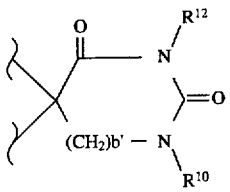

wherein each symbol is as defined above, and other symbols are as defined above, and a pharmaceutically acceptable salt thereof.

The preferable modes of the present invention include the following.

(1) A therapeutic agent for osteoporosis containing, as an active ingredient, a compound of the formula (I) wherein W is —(NR³⁶)— where R³⁶ forms a bond with R³⁵, or a pharmaceutically acceptable salt thereof, a method for treating osteoporosis by the administration of said compound and a use of said compound for producing a therapeutic agent for osteoporosis.

(2) A therapeutic agent for osteoporosis containing, as an active ingredient, a compound of the formula (I) wherein W is —(NR³⁶)— where R³⁶ forms a bond with R³⁵ and X and Y combinedly form =N—N=C(R⁶)— where R⁶ is as defined above, or a pharmaceutically acceptable salt thereof, a method for treating osteoporosis by the administration of said compound and a use of said compound for producing a therapeutic agent for osteoporosis.

(3) A therapeutic agent for osteoporosis containing, as an active ingredient, a compound of the formula (I) wherein W is —(NR³⁶)— where R³⁶ forms a bond with R³⁵ and X and Y combinedly form =N—N=C(R⁶')— where R⁶' is alkyl having 6 to 20 carbon atoms, or a pharmaceutically acceptable salt thereof, a method for treating osteoporosis by the administration of said compound and a use of said compound for producing a therapeutic agent for osteoporosis.

(4) A therapeutic agent for osteoporosis containing, as an active ingredient, a compound of the formula (I) wherein the ring Q is

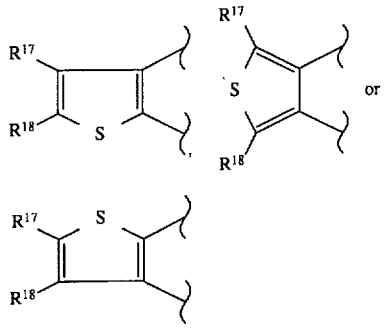

wherein R¹⁷ and R¹⁸ are as defined above, or a pharmaceutically acceptable salt thereof, a method for treating osteoporosis by the administration of said compound and a use of said compound for producing a therapeutic agent for osteoporosis.

(5) A therapeutic agent for osteoporosis containing, as an active ingredient, a compound of the formula (I) wherein W is —(NR³⁶)— where R³⁶ forms a bond with R³⁵, R is alkyl, aryl, heteroaryl, aralkyl, heteroarylalkyl or a group of the formula selected from —(CH₂)bN(R⁸)(R⁹)  (1)

—(CH₂)bOR¹⁰  (2)

$$-(CH_2)bN(R^{10})\overset{\overset{Z}{\|}}{C}N(R^{11})(R^{12})$$  (3)

—(CH₂)bN(R¹⁰)CORa¹¹  (4)

—(CH₂)bN(R¹⁰)SO₂R⁴⁴  (5)

—(CH₂)bN(R¹⁰)COOR⁴⁵  (6)

$$-(CH_2)b\overset{\overset{Z}{\|}}{O}CN(R^{11})(R^{12})$$  (7)

—(CH₂)bOCOR⁴⁶  (8)

—(CH₂)bCON(R⁴⁷)(R⁴⁸)  (9)

—(CH₂)bOSO₂R⁴⁴  (10)

—(CH₂)bCOR⁴⁹  (11)

—(CH₂)bS(O)nR¹¹  (12)

—CON(R¹⁰)OR⁸  (13)

$$-CON(R^{10})N(R^{10})\overset{\overset{Z}{\|}}{C}Ra^{11}$$  (14)

—CON(R¹⁰)N(R¹⁰)SO₂Ra¹¹  (15)

$$-N(R^{10})\overset{\overset{Z}{\|}}{C}N(R^{10})CORa^{11}$$  (16)

$$-(R^{10})\overset{\overset{Z}{\|}}{C}N(R^{10})SO_2Ra^{11}$$  (17)

—CON(R¹⁰)N(R¹⁰)(R¹¹)  (18)

—(CH$_2$)bN(R$^{10}$)COCON(R$^{11}$)(R$^{12}$)  (19)

and

—(CH$_2$)aCOOR$^1$  (20)

wherein each symbol is as defined above and the ring Q is a group of the formula

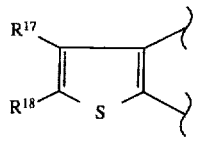

wherein each symbol is as defined above, or a pharmaceutically acceptable salt thereof, a method for treating osteoporosis by the administration of said compound and a use of said compound for producing a therapeutic agent for osteoporosis.

(6) A therapeutic agent for osteoporosis containing, as an active ingredient, a compound of the formula (I) wherein W is —(NR$^{36}$)— wherein R$^{36}$ forms a bond with R$^{35}$, R is alkyl, aryl, aralkyl or a group of the formula selected from —(CH$_2$)bN(R$^8$)(R$^9$)  (1)

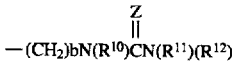  (3)

—(CH$_2$)bN(R$^{10}$)CORa$^{11}$  (4)

—(CH$_2$)bN(R$^{10}$)SO$_2$R$^{44}$  (5)

—(CH$_2$)bN(R$^{10}$)COOR$^{45}$  (6)

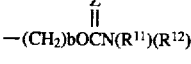  (7)

—(CH$_2$)bCON(R$^{47}$)(R$^{48}$)  (9)

—(CH$_2$)bOSO$_2$R$^{44}$  (10)

—(CH$_2$)bCOR$^{49}$  (11)

and

—(CH$_2$)aCOOR$^1$  (20)

wherein each symbol as defined above and the ring Q is a group of the formula

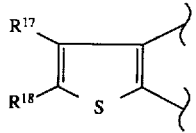

wherein each symbol is as defined above, or a pharmaceutically acceptable salt thereof, a method for treating osteoporosis by the administration of said compound and a use of said compound for producing a therapeutic agent for osteoporosis.

(7) A therapeutic agent for osteoporosis containing, as an active ingredient, a compound of the formula (I) which is selected from:

9-tert-butyl-4-(2-chlorophenyl)-2-(2-(4-isobutylphenyl)ethyl)-6-methyl-6H-thieno[3,2-f][1,2,4]triazolo[4,3-a][1,4]diazepine, 3-[4-(2-chlorophenyl)-6,9-dimethyl-6H-thieno[3,2-f][1,2,4]triazolo[4,3-a][1,4]diazepin-2-yl]propionic morpholide, 4-(2-chlorophenyl)-6,9-dimethyl-2-(3-morpholinopropyl)-6H-thieno[3,2-f][1,2,4]triazolo[4,3-a][1,4]diazepine, 4-(2-chlorophenyl)-2-(2-(4-isobutylphenyl)ethyl)-9-methyl-6-propyl-6H-thieno[3,2-f][1,2,4]triazolo[4,3-a][1,4]diazepine, 4-(2-chlorophenyl)-6-isobutyl-2-(2-(4-isobutylphenyl)ethyl)-9-methyl-6H-thieno[3,2-f][1,2,4]triazolo[4,3-a][1,4]diazepine, 4-(2-chlorophenyl)-2-(2-(4-isobutylphenyl)ethyl)-9-methyl-6-phenyl-6H-thieno[3,2-f][1,2,4]triazolo[4,3-a][1,4]diazepine, 6-benzyl-4-(2-chlorophenyl)-2-(2-(4-isobutylphenyl)ethyl)-9-methyl-6H-thieno[3,2-f][1,2,4]triazolo[4,3-a][1,4]diazepine, N-(4-(2-chlorophenyl)-2-ethyl-9-methyl-6H-thieno[3,2-f][1,2,4]triazolo[4,3-a][1,4]diazepin-6-yl)-2-indolecarboxamide, N-(4-(2-chlorophenyl)-2-ethyl-9-methyl-6H-thieno[3,2-f][1,2,4]triazolo[4,3-a][1,4]diazepin-6-yl)-3-indoleacetamide, 6-benzoylamino-4-(2-chlorophenyl)-2-ethyl-9-methyl-6H-thieno[3,2-f][1,2,4]triazolo[4,3-a][1,4]diazepine, 4-(2-chlorophenyl)-2-ethyl-9-methyl-6-(3-(3-tolyl)ureido)-6H-thieno[3,2-f][1,2,4]triazolo[4,3-a][1,4]diazepine, 8S-(+)-6-(2-chlorophenyl)-3-cyclopropanecarbonyl-8,11-dimethyl-2,3,4,5-tetrahydro-8H-pyrido[4',3':4,5]thieno[3,2-f][1,2,4]triazolo[4,3-a][1,4]diazepine, 6-(2-chlorophenyl)-8,9-dihydro1,4-dimethyl-8-morpholinocarbonyl-4H,7H-cyclopenta[4,5]thieno[3,2-f][1,2,4]triazolo[4,3-a][1,4]diazepine, (4-(4-chlorophenyl)-2-ethyl-9-methyl-6H-thieno[3,2-f][1,2,4]triazolo[4,3-a][1,4]diazepin-6-yl)acetic acid, N-(2-methoxyphenyl)-(4-(4-chlorophenyl)-2-ethyl-9-methyl-6H-thieno[3,2-f][1,2,4]triazolo[4,3-a][1,4]diazepin-6-yl)acetamide, N-phenyl-(4-(4-chlorophenyl)-2-ethyl-9-methyl-6H-thieno[3,2-f][1,2,4]triazolo[4,3-a][1,4]diazepin-6-yl)acetamide, N-(4-(4-chlorophenyl)-2-ethyl-9-methyl-6H-thieno[3,2-f][1,2,4]triazolo[4,3-a][1,4]diazepin-6-yl)-p-toluenesulfonamide, (4-(4-methoxyphenyl)-2-ethyl-9-methyl-6H-thieno[3,2-f][1,2,4]triazolo[4,3-a][1,4]diazepin-6-yl)-N-(3-methylphenyl)carbamate, 4-(2-chlorophenyl)-2-ethyl-9-methyl-6-phenylacetylamino-6H-thieno[3,2-f][1,2,4]triazolo[4,3-a][1,4]diazepine, N-(4-chlorophenyl)-N'-(4-(4-chlorophenyl)-2-ethyl-9-methyl-6H-thieno[3,2-f][1,2,4]triazolo[4,3-a][1,4]diazepin-6-yl)urea, N-(4-(4-chlorophenyl)-2-ethyl-9-methyl-6H-thieno[3,2-f][1,2,4]triazolo[4,3-a][1,4]diazepin-6-yl)-N'-(3-methoxyphenyl)urea, N-(4-(4-chlorophenyl)-2-hexyl-9-methyl-6H-thieno[3,2-f][1,2,4]triazolo[4,3-a][1,4]diazepin-6-yl)-N'-(3-methylphenyl)urea, N-(4-(2-chlorophenyl)-2,3,9-trimethyl-6H-thieno[3,2-f][1,2,4]triazolo[4,3-a][1,4]diazepin-6-yl)-N'-(3-methylphenyl)urea, N-(4-(2-chlorophenyl)-9-cyclohexyl-2-ethyl-6H-thieno[3,2-f][1,2,4]triazolo[4,3-a][1,4]diazepin-6-yl)-N'-(3-methoxyphenyl)urea, N-(2-ethyl-9-methyl-4-(4-methylphenyl)-6H-thieno[3,2-f][1,2,4]triazolo[4,3-a][1,4]diazepin-6-yl)-N'-(3-methylphenyl)urea, N-(4-(2-chlorophenyl)-2-ethyl-9-methyl-6H-thieno[3,2-f][1,2,4]triazolo[4,3-a][1,4]diazepin-6-yl)-N'-phenylurea, N-(2-ethyl-9-methyl-4-phenyl-6H-thieno[3,2-f][1,2,4]triazolo[4,3-a][1,4]diazepin-6-yl)-N'-(3-methylphenyl)urea, N-(4-(4-chlorophenyl)-2-ethyl-9-methyl-6H-thieno[3,2-f][1,2,4]triazolo[4,3-a][1,4]diazepin-6-yl)-N'-(2-methoxyphenyl)urea, N-(4-(2-chlorophenyl)-2-ethyl-9-methyl-6H-thieno[3,2-f][1,2,4]triazolo[4,3-a][1,4]diazepin-6-yl)-N'-phenylthiourea, N-(2-butyl-4-(4-chlorophenyl)-9-methyl-6H-thieno[3,2-f][1,2,4]triazolo[4,3-a][1,4]diazepin-6-yl)-N'-(3-methylphenyl)urea, N-(4-(2-chlorophenyl)-2-ethyl-9-cyclohexyl-6H-thieno[3,2-f][1,2,4]triazolo[4,3-a][1,4]diazepin-6-yl)-N'-(2-methylphenyl)urea, 4-(4-chlorophenyl)-2-ethyl-9-methyl-6-(3-phenylpropyl)-6H-thieno[3,2-f][1,2,4]triazolo[4,3-a][1,4]diazepine, 2-ethyl-4-phenyl-9-undecyl-4H,6H-thieno[2,3-e][1,2,4]triazolo[3,4-c][1,4]oxazepine, 6-(2-chlorophenyl)-1-undecyl-7,8,9,10-hexahydro-4H,6H -triazolo[3,4-c][1]benzothieno[2,3-e][1,4oxazepine, 4-(2-chlorophenyl)-2-(2-(4-isobutylphenyl)ethyl)-9-methyl-4H,6H-thieno[2,3-e][1,2,4]triazolo[3,4-c][1,4]oxazepine, 4-(4-chlorophenyl)-2-ethyl-9-(3-(4-isobutylphenyl)propyl)-4H,6H-thieno[2,3-e][1,2,4]triazolo[3,4-c][1,4]oxazepine, 2-ethyl-9-heptyl-4-(4-methoxyphenyl)-4H,6H-thieno[2,3-e][1,2,4]triazolo[3,4-c][1,4]oxazepine, 2-ethyl-4-(4-methylphenyl)-9-undecyl-4H,6H-thieno[2,3-e][1,2,4]triazolo[3,4-c][1,4]oxazepine, 2-ethyl-4-(4-hydroxyphenyl)-9-undecyl-4H,6H-thieno[2,3-e][1,2,4]triazolo[3,4-c][1,4]oxazepine, and 2-ethyl-4-(4-(2-dimethylaminoethoxy)phenyl)-9-undecyl-4H,6H-thieno[2,3-e][1,2,4]triazolo[3,4-c][1,4]oxazepine or a pharmaceutically acceptable salt thereof, a method for treating osteoporosis by the administration of said compound and a use of said compound for producing a therapeutic agent for osteoporosis.

(8) A therapeutic agent for osteoporosis containing, as an active ingredient, a compound of the formula (I) wherein the ring Q is a group of the formula

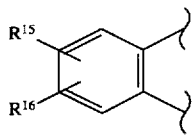

wherein $R^{15}$ and $R^{16}$ are as defined above, or a pharmaceutically acceptable salt thereof, a method for treating osteoporosis by the administration of said compound and a use of said compound for producing a therapeutic agent for osteoporosis.

(9) A therapeutic agent for osteoporosis containing, as an active ingredient, a compound of the formula (I) wherein the ring Q is a group of the formula

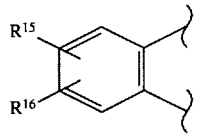

wherein $R^{15}$ and $R^{16}$ are as defined above, N is —(NR$^{36}$)— where $R^{36}$ is hydrogen or forms a bond with $R^{35}$ or —O—, R is hydrogen, heteroarylalkyl or a group of the formula selected from

 (3)

 (5)

 (6)

 (7)

 (8)

 (9)

 (10)

 (13)

 (14)

 (16)

 (17)

and

 (18)

where in each symbol is as defined above, and R' is hydrogen or —COOR$^8$ wherein $R^8$ is as defined above, or R and R' combinedly form a spiro ring of the formula

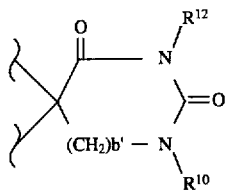

wherein each symbol is as defined above, or a pharmaceutically acceptable salt thereof, a method for treating osteoporosis by the administration of said compound and a use of said compound for producing a therapeutic agent for osteoporosis.

(10) A therapeutic agent for osteoporosis containing, as an active ingredient, a compound of the formula (I) which is selected from 6-(4-chlorophenyl)-1-undecyl-4H,6H-[1,2,4]triazolo[4,3-a][1,4]benzoxazepine, 8-decyl1,4-dimethyl-6-phenyl-4H-[1,2,4]triazolo[4,3-a] [1,4]benzodiazepine, 9-decyl1,4-dimethyl-6-phenyl-4H-[1,2,4]triazolo[4,3-a] [1,4]benzodiazepine, 6-(4-chlorophenyl)-1-undecyl-4H-[1,2,4]triazolo[4,3-a] [1,4]benzodiazepine, 6-(4-chlorophenyl)-1-undecyl-4H,5H,6H-[1,2,4]triazolo [4,3-a][1,4]benzodiazepine, 6-(4-chlorophenyl)-1-(3-(isobutylphenyl)propyl)-4H-[1, 2,4]triazolo[4,3-a][1,4]benzodiazepine, N-benzoyl-N'-(6-(4-chlorophenyl)-1-methyl-4H-[1,2,4] triazolo[4,3-a][1,4]benzodiazepin-4-yl)urea, N-(6-(4-chlorophenyl)-1-methyl-4H-[1,2,4]triazolo[4,3-a][1,4]benzodiazepin-4-yl)-N'-(2-pyridyl)urea, N-(6-(4-chlorophenyl)-1-methyl-4H-[1,2,4]triazolo[4,3-a][1,4]benzodiazepin-4-yl)-N'-(3-pyridyl)urea, N-(8-chloro-1-methyl-6-phenyl-4H-[1,2,4]triazolo[4,3-a] [1,4]benzodiazepin-4-yl)-N'-(2-methoxyphenyl)urea, N-(6-(4-chlorophenyl)-1-methyl-4H-[1,2,4]triazolo[4,3-a][1,4]benzodiazepin-4-yl)-N'-(2-methoxyphenyl)urea, N-(6-(4-chlorophenyl)-1-methyl-4H-[1,2,4]triazolo[4,3-a][1,4]benzodiazepin-4-yl)-N'-(3-tolyl)urea, N-(6-(4-chlorophenyl)-1-methyl-4H-[1,2,4]triazolo[4,3-a][1,4]benzodiazepin-4-yl)-N'-phenyl-oxalyldiamide, N-(1-methyl-6-(2-thienyl)-4H-[1,2,4]triazolo[4,3-a][1,4] benzodiazepin-4-yl)-N'-(3-tolyl)urea, 6-(4-chlorophenyl)-1-methyl-4H-[1,2,4]triazolo[4,3-a][1, 4]benzodiazepine-4-spiro-5'-(3'-(3-tolyl)-2',4'-dioxoimidazolidine), N-(6-(4-chlorophenyl)-4-ethoxycarbonyl-1-methyl-4H-[1,2,4]triazolo[4,3-a][1,4]benzodiazepin-4-yl)-N'-(3-tolyl)urea, (1-methyl-6-phenyl-4H-[1,2,4]triazolo[4,3-a][1,4]benzodiazepin-4-yl)methyl-p-toluenesulfonate, N-(6-(4-chlorophenyl)-1-methyl-4H-[1,2,4]triazolo[4,3-a][1,4]benzodiazepin-4-yl)methyl-N'-(2-methoxyphenyl)urea, N-[6-(4-chlorophenyl)-1-methyl-4H-[1,2,4]triazolo[4,3-a][1,4]benzodiazepin-4-yl)methyl]-N'-(3-tolyl)urea, N-(3-tolyl)-O-((1-methyl-6-phenyl-4H-[1,2,4]triazolo[4, 3-a][1,4]benzodiazepin-4-yl)methyl)carbamate, N-(2-methoxyphenyl)-O-((1-methyl-6-phenyl-4H-[1,2,4] triazolo[4,3-a][1,4]benzodiazepin-4-yl)methyl)carbamate, (1-methyl-6-phenyl-4H-[1,2,4]triazolo[4,3-a][1,4]benzodiazepin-4-yl)methyl phenylacetate, 6-(4-chlorophenyl)-4-(3-indolylmethyl)-1-methyl-4H-[1, 2,4]triazolo[4,3-a][1,4]benzodiazepine, N-(6-(4-chlorophenyl)-1-methyl-4H-[1,2,4]triazolo[4,3-a][1,4]benzodiazepin-4-yl)-O-benzyl carbamate, N-(6-(4-chlorophenyl)-1-methyl-4H-[1,2,4]triazolo[4,3-a][1,4]benzodiazepin-4-yl)benzylsulfonamide, (6-(4-chlorophenyl)-1-methyl-4H-[1,2,4]triazolo[4,3-a] [1,4]benzodiazepin-4-yl)carbohydrazide, N'-p-tosyl-(6-(4-chlorophenyl)-1-methyl-4H-[1,2,4]triazolo[4,3-a][1,4]benzodiazepin-4-yl)carbohydrazide, O-benzyl-N-(6-(4-chlorophenyl)-1-methyl-4H-[1,2,4] triazolo[4,3-a][1,4]benzodiazepin-4-yl)carbohydroxamate, N-benzyl-(6-(4-chlorophenyl)-1-methyl-4H-[1,2,4]triazolo[4,3-a][1,4]benzodiazepine-1-yl)carboxamide, N-(6-(4-chlorophenyl)-1-methyl-4H-[1,2,4]triazolo[4,3-a][1,4]benzodiazepin-4-yl)methyl-2-indolecarboxamide, N-benzyl-N'-(6-(4-chlorophenyl)-1-methyl-4H-[1,2,4] triazolo[4,3-a][1,4]benzodiazepin-4-yl)urea, N-(6-(4-chlorophenyl)-1-methyl-4H-[1,2,4]triazolo[4,3-a][1,4]benzodiazepin-4-yl)-N'-(cyclohexyl)urea, N-(6-(4-chlorophenyl)-1-methyl-4H-[1,2,4]triazolo[4,3-a][1,4]benzodiazepin-4-yl)-2-indolecarboxamide, 8-chloro-6-(2-chlorophenyl)-1-methyl-4H-[1,2,4]triazolo [4,3-a][1,4]benzodiazepine, 8-chloro-6-phenyl-1-methyl-4H-[1,2,4]triazolo[4,3-a][1, 4]benzodiazepine, and 8-chloro-6-(2-chlorophenyl)-4H-imidazo[1,2-a][1,4]benzodiazepine or a pharmaceutically acceptable salt thereof, a method for treating osteoporosis by the administration of said compound and a use of said compound for producing a therapeutic agent for osteoporosis.

(11) A benzotriazolodiazepine compound selected from 8-decyl1,4-dimethyl-6-phenyl-4H-[1,2,4]triazolo[4,3-a] [14]benzodiazepine, 9-decyl1,4-dimethyl-6-phenyl-4H-[1,2,4]triazolo[4,3-a] [1,4]benzodiazepine, N-benzoyl-N'-6-(4-chlorophenyl)-1-methyl-4H-[1,2,4] triazolo[4,3-a][1,4]benzodiazepin-4-yl)urea, N-(p-tosyl)-N'-(6-(4-chlorophenyl)-1-methyl-4H-[1,2,4] triazolo[4,3-a][1,4]benzodiazepin-4-yl)urea, N-(6-(4-chlorophenyl)-1-methyl-4H-[1,2,4]triazolo[4,3-a][1,4]benzodiazepin-4-yl)-N'-(2-pyridyl)urea, N-(6-(4-chlorophenyl)-1-methyl-4H-[1,2,4]triazolo[4,3-a][1,4]benzodiazepin-4-yl)-N'-(3-pyridyl)urea, N-(6-(4-chlorophenyl)-1-methyl-4H-[1,2,4]triazolo[4,3-a][1,4]benzodiazepin-4-yl)-N'-phenyl-oxalyldiamide, N-(1-methyl-6-(2-thienyl)-4H-[1,2,4]triazolo[4,3-a][1,4] benzodiazepin-4-yl)-N'-(3-tolyl)urea, 6-(4-chlorophenyl)-1-methyl-4H-[1,2,4]triazolo[4,3-a][1, 4]benzodiazepine-4-spiro-5'-(3'-(3-tolyl)-2'-4'-dioxoimidazolidine), N'-phenyl-(6-(4-chlorophenyl)-1-methyl-4H-[1,2,4]triazolo[4,3-a][1,4]benzodiazepin-4-yl)carbohydrazide, N'-benzoyl-(6-(4-chlorophenyl)-1-methyl-4H-[1,2,4]triazolo[4,3-a][1,4]benzodiazepin-4-yl)carbohydrazide, O-benzyl-N-(6-(4-chlorophenyl)-1-methyl-4H-[1,2,4] triazolo[4,3-a][1,4]benzodiazepin-4-yl)carbohydraxamate, N-benzyl-(6-(4-chlorophenyl)-1-methyl-4H-[1,2,4]triazolo[4,3-a][1,4]benzodiazepin-4-yl)carboxamide, 6-(4-chlorophenyl)-1-undecyl-4H,5H,6H-[1,2,4]triazolo [4,3-a][1,4]benzodiazepine, (1-methyl-6-phenyl-4H-[1,2,4]triazolo[4,3-a][1,4]benzodiazepin-4-yl)methyl-p-toluenesulfonate, (6-(4-chlorophenyl)-1-methyl-4H-[1,2,4]triazolo[4,3-a] [1,4]benzodiazepin-4-yl)carbohydrazide, N'-p-tosyl-(6-(4-chlorophenyl)-1-methyl-4H-[1,2,4]triazolo[4,3-a][1,4]benzodiazepin-4-yl)carbohydrazide, N-(6-(4-chlorophenyl)-1-methyl-4H-[1,2,4]triazolo[4,3-a][1,4]benzodiazepin-4-yl)methyl-2-indolecarboxamide, N-(6-(4-chlorophenyl)-1-methyl-4H-[1,2,4]triazolo[4,3-a][1,4]benzodiazepin-4-yl)-N'-(cyclohexyl)urea, and N-(6-(4-chlorophenyl)-1-methyl-4H-[1,2,4]triazolo[4,3-a][1,4]benzodiazepin-4-yl)-2-indolecarboxamide or a pharmaceutically acceptable salt thereof.

As used herein, each substituent is defined as follows.

Aryl in Ar, $R^1$, $R^5$ and $R^6$ is phenyl which may have, on the ring, 1 to 3 substituents selected from halogen (chlorine, bromine, fluorine), alkyl (alkyl having 1 to 6 carbon atoms such as methyl, ethyl, propyl, isopropyl, butyl, tert-butyl, isobutyl, pentyl, isopentyl and hexyl), alkoxy (alkoxy having 1 to 6 carbon atoms such as methoxy, ethoxy, propoxy, isopropoxy, butoxy, tert-butoxy and hexyloxy), haloalkyl (that wherein alkyl moiety is C1–C4 alkyl, such as chloromethyl, bromomethyl, fluoromethyl, trifluoromethyl, trifluoroethyl, pentafluoropropyl and chlorobutyl), hydroxy, nitro, amino, cyano, acyloxy (e.g. that wherein acyl moiety is alkanoyl having 2 to 5 carbon atoms, such as acetyl, propionyl, butyryl and pivaloyl, or aroyl (e.g. benzoyl which may have, on the ring, 1 to 3 substituents selected from halogen (as defined above), alkyl (as defined above), alkoxy (as defined above), haloalkyl (as defined above) and hydroxy, such as benzoyl, chlorobenzoyl, methylbenzoyl and methoxybenzoyl) and aralkyl (that wherein alkyl moiety has 1 to 6 carbon atoms, which may have, on the ring, 1 to 3 substituents selected from halogen (as defined above), alkyl (as defined above), alkoxy (as defined above), and hydroxy, such as benzyl, 2-phenylethyl and 3-phenylpropyl).

Heteroaryl of Ar is pyridyl or thienyl which may have, on the ring, 1 to 3 substituents selected from halogen (chlorine, bromine, fluorine), alkyl (alkyl having 1 to 6 carbon atoms such as methyl, ethyl, propyl, isopropyl, butyl, tert-butyl, isobutyl, pentyl, isopentyl and hexyl), alkoxy (alkoxy having 1 to 6 carbon atoms such as methoxy, ethoxy, propoxy, isopropoxy, butoxy, tert-butoxy and hexyloxy), haloalkyl (that wherein alkyl moiety is alkyl having 1 to 4 carbon atoms, such as chloromethyl, bromomethyl, fluoromethyl, trifluoromethyl, trifluoroethyl, pentafluoropropyl and chlorobutyl), hydroxy, nitro, amino, cyano, acyloxy (e.g. that wherein acyl moiety is alkanoyl having 2 to 5 carbon atoms, such as acetyl, propionyl, butyryl and pivaloyl, or aroyl such as benzoyl which may have, on the ring, 1 to 3 substituents selected from halogen (as defined above), alkyl (as defined above), alkoxy (as defined above), haloalkyl (as defined above) and hydroxy, such as benzoyl, chlorobenzoyl, methylbenzoyl and methoxybenzoyl).

Unless otherwise specified, as used in the present specification, alkyl means straight or branched alkyl having 1 to 20 carbon atoms, such as methyl, ethyl, propyl, isopropyl, butyl, isobutyl, tert-butyl, pentyl, tert-pentyl, hexyl, heptyl, octyl, 2-ethylhexyl, 2,2-diethyloctyl, 1,1,3,3-tetramethylbutyl, nonyl, decyl, undecyl, dodecyl, tetradecyl, pentadecyl, octadecyl, heptadecyl and eicosyl. The preferable carbon number of the alkyl is 1 to 6.

Unless specifically indicated, alkenyl means that having 2 to 20 carbon atoms, such as vinyl, propenyl, 2-methyl-1-propenyl, 3-methyl-1-butenyl, 2,3-dimethyl-1-butenyl, 3,4,5-trimethyl-1-butenyl, 3-butenyl, 3-hexenyl, 5-dodecenyl, 6-ethyl -3-decenyl, 11,11-dimethyl-7-tetradecenyl, 14-octadecenyl and 8-eicosenyl. The preferable carbon number of the alkenyl is 2 to 8.

Unless specifically indicated, alkynyl means that having 2 to 20 carbon atoms, such as 1-propynyl, 3-methyl-1-butynyl, 1,4-dimethyl-1-hexynyl, ethynyl, propargyl, 3-hexynyl, 3,4-diethyl-1-octynyl, 5-dodecynyl, 6-ethyl-3-decynyl, 11,11-dimethyl-7-tetradecynyl, 14-octadecynyl and 8-eicosynyl. The preferable carbon number of the alkynyl is 2 to 8.

Aralkyl is that where aryl moiety is phenyl and alkyl moiety is C1–C6 alkyl and exemplified by benzyl, phenylethyl, phenylpropyl, phenylbutyl and phenylhexyl, which may have, on the ring, 1 to 3 substituents selected from halogen (chlorine, bromine, fluorine), alkyl (alkyl having 1 to 6 carbon atoms such as methyl, ethyl, propyl, isopropyl, butyl, tert-butyl, isobutyl, pentyl, isopentyl and hexyl), alkoxy (alkoxy having 1 to 6 carbon atoms such as methoxy, ethoxy, propoxy, isopropoxy, butoxy, tert-butoxy and hexyloxy), haloalkyl (that wherein alkyl moiety is alkyl having 1 to 4 carbon atoms, such as chloromethyl, bromomethyl, fluoromethyl, trifluoromethyl, trifluoroethyl, pentafluoropropyl and chlorobutyl), hydroxy, nitro, amino, cyano, acyloxy (e.g. that wherein acyl moiety is alkanoyl having 2 to 5 carbon atoms such as acetyl, propionyl, butyryl and pivaloyl, or aroyl such as benzoyl which may have, on the ring, 1 to 3 substituents selected from halogen (as defined above), alkyl (as defined above), alkoxy (as defined above), haloalkyl (as defined above) and hydroxy, such as benzoyl, chlorobenzoyl, methylbenzoyl and methoxybenzoyl).

Cycloalkyl has 3 to 10 carbon atoms and is exemplified by cyclopropyl, 2,3-dimethylcyclopropyl, cyclobutyl, 3-methylcyclobutyl, cyclopentyl, 3,4-dimethylcyclopentyl, cyclohexyl, 4-methylcyclohexyl, cycloheptyl, cyclooctyl, norbornyl, adamantyl, bicyclo[3.3.0]octan-1-yl and bicyclo [3.3.1]nonan-9-yl.

The heterocycle formed by $R^2$ and $R^3$, or $R^{41}$ and $R^{42}$, or $R^{53}$ and $R^{54}$ together with the adjacent nitrogen atom is exemplified by 1-pyrrolidinyl, piperidino, homopiperidino, 1-piperazinyl, 1-piperazinyl substituted by alkyl at the 4-position, morpholino and thiomorpholino.

Halogen means chlorine, bromine, fluorine and iodine.

Cycloalkylalkyl is that wherein cycloalkyl moiety has 3 to 10 carbon atoms and alkyl moiety has 1 to 6, preferably 1 to 3 carbon atoms and is exemplified by cyclopropylmethyl, 2,3-dimethylcyclopropylmethyl, cyclobutylmethyl, 3-methylcyclobutylmethyl, cyclopentylmethyl, 3,4-dimethylcyclopentylmethyl, cyclohexyl methyl, 4-methylcyclohexylmethyl, cycloheptylmethyl, cyclooctylmethyl, 2-cyclohexylethyl, 3-cyclohexylpropyl, norbornylmethyl, 1-adamantyl methyl, bicyclo[3.3.0]octan-1-ylmethyl and bicyclo[3.3.1]nonan-9-ylmethyl.

Heteroaryl at $R^5$ and $R^6$ may have at least one hetero atom selected from oxygen, sulfur and optionally substituted nitrogen as a ring constituting atom and is a 5 to 7-membered ring which may be condensed with aryl or heteroaryl optionally having, on the ring, the aforementioned substituent. Examples thereof include furyl, thienyl, pyrrolyl, imidazolyl, tetrazolyl, oxazolyl, thiazolyl, pyridyl, pyridazinyl, pyrimidinyl, triazinyl, benzofuryl, 2,3-dihydrobenzofuryl, benzopyranyl, benzimidazolyl, benzoxazolyl, quinolyl and benzoxazinyl, which may have, on the ring, to 3 substituents selected from halogen (chlorine, bromine, fluorine), alkyl (alkyl having 1 to 6 carbon atoms such as methyl, ethyl, propyl, isopropyl, butyl, tert-butyl, isobutyl, pentyl, isopentyl and hexyl), alkoxy (alkoxy having 1 to 6 carbon atoms such methoxy, ethoxy, propoxy, isopropoxy, butoxy, tert-butoxy and hexyloxy), haloalkyl (that wherein alkyl moiety is alkyl having 1 to 4 carbon atoms, such as chloromethyl, bromomethyl, fluoromethyl, trifluoromethyl, trifluoroethyl, pentafluoropropyl and chlorobutyl), hydroxy, nitro, amino, cyano, acyloxy (e.g. that wherein acyl moiety is alkanoyl having 2 to 5 carbon atoms, such as acetyl, propionyl, butyryl and pivaloyl, or aroyl such as benzoyl which may have, on the ring, 1 to 3 substituents selected from halogen (as defined above), alkyl (as defined above), alkoxy (as defined above), haloalkyl (as defined above) and hydroxy, such as benzoyl, chlorobenzoyl, methylbenzoyl and methoxybenzoyl).

Heteroarylalkyl may have, on the ring, 1 to 8 substituents selected from halogen, C1–C6 alkyl, C1–C6 alkoxy, trifluoromethyl, nitro, amino, cyano and hydroxy and alkyl moiety has 1 to 4, preferably 1 to 2 carbon atoms and the hetero atom constituting the ring is nitrogen, oxygen or sulfur. Examples thereof include pyridyl(2-pyridyl, 3-pyridyl, 4-pyridyl)methyl, quinolyl(2-quinolyl, 3-quinolyl)methyl, indolyl(2-indolyl, 3-indolyl)methyl, thienyl(2-thienyl, 3-thienyl)methyl, furyl(2-furyl, 3-furyl)methyl, benzofuryl(2-benzofuryl, 3-benzofuryl)methyl, 1H-benzimidazol-2-ylmethyl, 2-benzothiazolylmethyl, 2-(2-thienyl)ethyl and 2-(2-furyl)ethyl.

Aryloxyalkyl is that wherein aryl moiety is phenyl and alkyl moiety is C1–C6 alkyl and is exemplified by phenoxymethyl, phenoxyethyl, phenoxypropyl, phenoxybutyl and phenoxyhexyl, which may have, on the ring, 1 to 3 substituents selected from halogen (chlorine, bromine, fluorine), alkyl (alkyl having 1 to 6 carbon atoms such as methyl, ethyl, propyl, isopropyl, butyl, tert-butyl, isobutyl, pentyl, isopentyl and hexyl), alkoxy (alkoxy having 1 to 6 carbon atoms such as methoxy, ethoxy, propoxy, isopropoxy, butoxy, tert-butoxy and hexyloxy), haloalkyl (that wherein alkyl moiety is alkyl having 1 to 4 carbon atoms, such as chloromethyl, bromomethyl, fluoromethyl, trifluoromethyl, trifluoroethyl, pentafluoropropyl and chlorobutyl), hydroxy, nitro, amino, cyano and acyloxy (e.g. that wherein acyl moiety is alkanoyl having 2 to 5 carbon atoms, such as acetyl, propionyl, butyryl and pivaloyl, or aroyl such as benzoyl which may have, on the ring, 1 to 3 substituents selected from halogen (as defined above), alkyl (as defined above), alkoxy (as defined above), haloalkyl (as defined above) and hydroxy, such as benzoyl, chlorobenzoyl, methylbenzoyl, methoxybenzoyl).

Haloalkyl is that wherein alkyl moiety has 1 to 5 carbon atoms and is exemplified by chloromethyl, bromomethyl, fluoromethyl, trifluoromethyl, trifluoroethyl, pentafluoropropyl and chlorobutyl.

Aryl may be, for example, phenyl, 1-naphthyl or 2-naphthyl which may have, on the aromatic ring, 1 to 3 substituents selected from halogen, C1–C6 alkyl, C1–C6 alkoxy, trifluoromethyl, nitro, amino, cyano and hydroxy.

Heteroaryl may have, on the ring, 1 to 3 substituents selected from halogen, C1–C6 alkyl, C1–C6 alkoxy, trifluoromethyl, nitro, amino, cyano and hydroxy and the hetero atom constituting the ring is nitrogen, oxygen or sulfur. Examples thereof include pyridyl (2-pyridyl, 3-pyridyl, 4-pyridyl), quinolyl (2-quinolyl, 3-quinolyl), indolyl (2-indolyl, 3-indolyl), thienyl (2-thienyl, 3-thienyl), furyl (2-furyl, 3-furyl), benzofuryl (2-benzofuryl, 3-benzofuryl), 1H-benzimidazol-2-yl and 2-benzothiazolyl.

Alkoxy is exemplified by alkoxy having 1 to 6 carbon atoms, such as methoxy, ethoxy, propoxy, isopropoxy, butoxy, isobutoxy, tert-butoxy, pentyloxy, isopentyloxy and hexyloxy.

Acyl is alkanoyl having 2 to 5 carbon atoms, such as acetyl, propionyl, butyryl and pivaloyl, or benzoyl.

Acyloxy is alkanoyloxy having 2 to 5 carbon atoms, such as acetyloxy, propionyloxy, butyryloxy and pivaloyloxy, or benzoyloxy.

Amino substituted by alkyl is amino mono- or di-substituted by alkyl having 1 to 5 carbon atoms and is exemplified by methylamino, dimethylamino, ethylamino, diethylamino, propylamino and dipropylamino.

Cyclic amino is exemplified by pyrrolidinyl, piperidino, and morpholino, thiomorpholino and piperazinyl having, as a hetero atom, oxygen, sulfur or nitrogen atom wherein the nitrogen atom may be substituted by alkyl or aralkyl.

Carbamoyl substituted by alkyl is carbamoyl mono- or di-substituted by alkyl having 1 to 5 carbon atoms and is exemplified by methylcarbamoyl, dimethylcarbamoyl, ethylcarbamoyl, diethylcarbamoyl, propylcarbamoyl and dipropylcarbamoyl.

Cyclic aminocarbonyl is that having the aforementioned cyclic amino moiety and is exemplified by pyrrolidinylcarbonyl, piperidinocarbonyl, morpholinocarbonyl, thiomorpholinocarbonyl, piperazinylcarbonyl and 4-methyl-1-piperazinylcarbonyl.

Alkoxycarbonyl is that wherein alkoxy moiety has 1 to 5 carbon atoms and is exemplified by methoxycarbonyl, ethoxycarbonyl, propoxycarbonyl, isopropoxycarbonyl, butoxycarbonyl, isobutoxycarbonyl and tert-butoxycarbonyl.

Aralkyloxycarbonyl is that wherein alkoxy moiety has 1 to 5 carbon atoms and is exemplified by benzyloxycarbonyl, 2-phenylethoxycarbonyl and 3-phenylpropoxycarbonyl, which may have halogen, nitro, alkyl, alkoxy, trifluoromethyl or the like as a substituent.

Alkylcarbonyl is that where alkyl moiety has 1 to 5 carbon atoms and is exemplified by acetyl, propionyl, butyryl, isobutyryl and pivaloyl.

Alkylene is exemplified by alkylene having 1 to 10 carbon atoms such as methylene, ethylene, trimethylene, tetramethylene, hexamethylene, octamethylene and decamethylene, which may optionally have branched chain and may be substituted by 1 to 3 hydroxys.

Alkenylene is exemplified by alkenylene having 2 to 8 carbon atoms and optionally having branched chain, such as vinylene, propenylene, butynylene, hexenylene and octenylene; alkynylene is exemplified by alkynylene having 2 to 8 carbon atoms and optionally having branched chain, such as ethynylene, propynylene, butynylene, hexynylene and octynylene.

Aryloxy may be, for example, phenoxy or naphthyloxy.

Aralkyloxy is that wherein alkyl moiety has 1 to 6 carbon atoms and is exemplified by benzyloxy, 2-phenylethoxy and 3-phenylpropoxy.

Alkenyl or alkynyl having 2 to 18 carbon atoms which may be substituted by 1 to 3 hydroxys is exemplified by 3-hydroxy-1-propenyl, 3-methyl-3-hydroxy-1-butenyl, 3,4-dihydroxy-1-butenyl, 3,4,5-trihydroxy-1-hexenyl, 3-hydroxy-1-propynyl, 1-hydroxy-2-butynyl and 1,4-dihydroxy-2-butynyl.

Aralkenyl or aralkynyl having alkenyl moiety or alkynyl moiety having 2 to 18 carbon atoms which may be substituted by 1 to 3 hydroxys is exemplified by 3-phenyl-1-propynyl, 3-phenyl-2-butenyl, 3-(4-methylphenyl)-2-butenyl, 2-methyl-4-phenyl-1-butenyl, 4-(4-methylphenyl)-1-butenyl, 4-phenyl-1-butenyl, 3-phenyl-1-propynyl, 4-(3-methoxyphenyl)-2-butynyl, 4-phenyl-3-methyl-1-butynyl, 4-phenyl-1-butynyl, 4-(4-methylphenyl)-1-butynyl and 3-phenyl-3-hydroxy-1-butenyl, 3-phenyl-4-hydroxy-1-hexenyl, 3-phenyl-3-hydroxy-1-propynyl, 3,4-dihydroxy-5-phenyl-1-pentynyl and 4-(2-methylphenyl)-1-hydroxy-2-butynyl.

In the definitions for $R^{20}$, $R^{21}$, $R^{22}$ and $R^{23}$, a saturated or unsaturated 3 to 7-membered ring formed combinedly with the adjacent nitrogen atom, which may be substituted by straight- or branched chain alkyl and which may have, in the ring, nitrogen, oxygen or sulfur atom as a hetero atom (the additional nitrogen atom being optionally substituted by straight- or branched chain alkyl having 1 to 4 carbon atoms, aralkyl or diarylalkyl) is exemplified by 1-aziridinyl, 1-azetidinyl, 1-pyrrolidinyl, piperidino, 1-piperazinyl, 1-azepinyl, 1-perhydroazepinyl, morpholino, thiomorpholino, 1-imidazolyl, 4-methyl-1-piperazinyl, 2,6-dimethylmorpholino, 1,2,4-triazol-1-yl, 1-pyrazolyl, 1-pyrrolyl, 4-benzyl-1-piperazinyl, 4-benzylpiperidino, 4-diphenylmethylpiperidino and 4-diphenylmethyl-1-piperazinyl.

Straight- or branched chain alkyl, alkenyl or alkynyl which may be substituted by halogen, hydroxy, amino, alkylamino, dialkylamino, cyclic amino or C-bonded heterocycle (carbons may be interrupted by nitrogen, oxygen or sulfur) is exemplified by methyl, ethyl, propyl, isopropyl, butyl, isobutyl, tert-butyl, pentyl, isopentyl, neopentyl, hexyl, octyl, decyl, vinyl, allyl, isopropenyl, 2-butenyl, ethynyl, 2-propynyl, chloromethyl, trifluoromethyl, 2-hydroxyethyl, aminomethyl, methyl aminomethyl, dimethylaminomethyl, 2-dimethylaminoethyl, 2-morpholinoethyl, 2-piperidinoethyl, furfuryl, 2-(2-indolyl)-ethyl, 2-thenyl, 2-pyridylmethyl, 2-quinolylmethyl and 2-pyrimidinylmethyl.

Straight- or branched chain alkylcarbonyl which may be mono- or di-substituted by hydroxy, halogen, amino, alkylamino, dialkylamino, cyclic amino or straight- or branched chain alkyl (the alkyl may be substituted by halogen or hydroxy) is exemplified by acetyl, propionyl, butyryl, isobutyryl and pivaloyl and those substituted by hydroxy, chlorine, amino, methylamino, dimethylamino, morpholino, methyl or ethyl.

Arylcarbonyl means, for example, benzoyl, 4-hydroxybenzoyl, 2-chlorobenzoyl or 4-methylbenzoyl.

Arylsulfonyl is, for example, phenylsulfonyl, 4-methylphenylsulfonyl, 4-aminophenylsulfonyl or 4-acetylaminophenylsulfonyl.

Alkylsulfonyl is, for example, methanesulfonyl, ethanesulfonyl, propanesulfonyl or butanesulfonyl.

Arylcarbonyl at $R^{24}$ is, for example, benzoyl, thiazolylcarbonyl, imidazolylcarbonyl; alkyl having hydroxy and/or carbonyl may be, for example, hydroxymethyl, 1-hydroxy-2-methylpropyl, 3-hydroxy-2-methylpropyl, 1-hydroxyethyl, 2-hydroxy-2-methylpropyl or isobutyryl.

Heteroaryl which may be hydrogenated is monocyclic 5-, 6- or 7-membered heterocyclic group or bicyclic or tricyclic group having one or more hetero atoms selected from nitrogen, oxygen and sulfur and said group may be substituted, preferably mono- or di-substituted by lower alkyl, lower alkoxy, oxo, hydroxy, chlorine or fluorine and is exemplified by the groups of the following formulas.

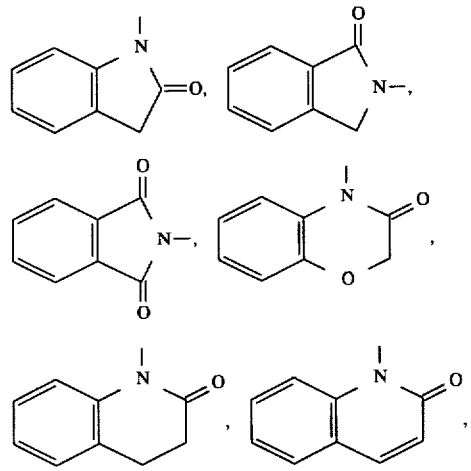

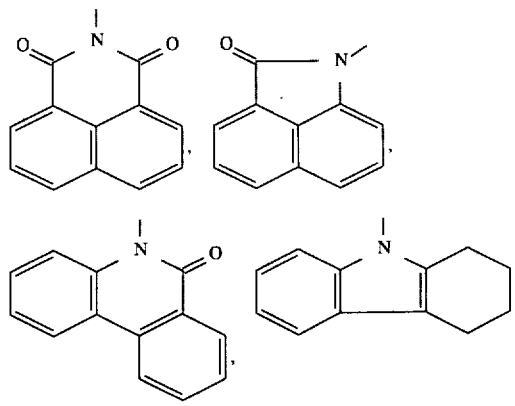

A saturated or unsaturated 5-, 6- or 7-membered ring which is, together with $R^{17}$ and $R^{18}$, condensed to thiophene ring is exemplified by

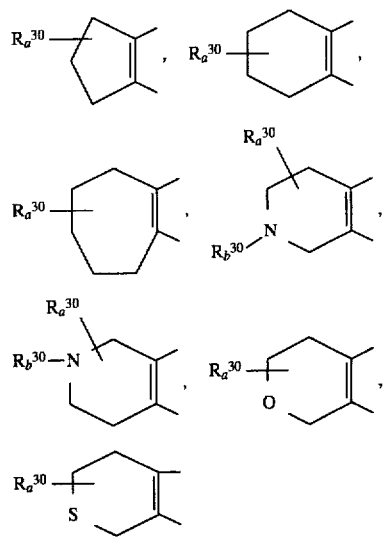

Examples of cycloalkyl in cycloalkyl, cycloalkylcarbonyl, cycloalkoxycarbonyl, cycloalkylalkylcarbonyl, cycloalkylalkoxycarbonyl and cycloalkylaminocarbonyl include cyclopropyl, cyclobutyl, cyclopentyl, cyclohexyl and cycloheptyl, which may be substituted by halogen, alkyl, alkoxy, trifluoromethyl or phenyl.

When the compound of the present invention has one or more asymmetric carbons, the present invention encompasses all racemates, diastereomers and individial optical isomers.

Most of the compounds of the formula (I) can be produced, separated and purified by the methods described in the prior art references indicated under Background Art.

Of the compounds of formula (I), novel compounds can be produced by the methods described in the following.

Method 1

An aminoketone described in Japanese Patent Unexamined Publication No. 256681/1990

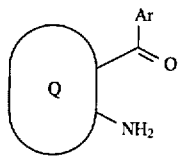

(IV)

wherein each symbol is as defined above, is reacted with a compound of the formula

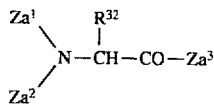

(V)

wherein $Za^1$ and $Za^2$ are each hydrogen, an amino-protecting group such as tert-butoxycarbonyl or benzyloxycarbonyl, or both combinedly form an amino-protecting group such as phthaloyl and $Za^3$ is a reactive group of hydroxy or carboxyl such as halogen, a mixed anhydride-forming group and an imidazolidide-forming group, to give an acyl compound, which is then deprotected by a conventional method using hydrazine hydrate or the like. The compound thus obtained of the formula

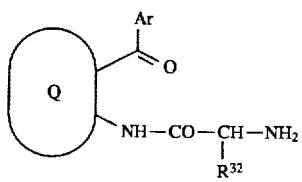

(VI)

wherein each symbol is as defined above, is subjected to a ring closure reaction with dehydration in an inert solvent such as ethanol, isopropyl alcohol, benzene or toluene in the presence of a weak acid such as acetic acid, propionic acid or silica gel at room temperature or under heating to give a compound of the formula (VII)

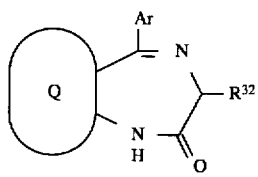

(VII)

wherein each symbol is as defined above.

The compound (VII) can be led to a compound (VIII) by the method described in Japanese Patent Unexamined Publication No. 82/1989 or 256681/1990.

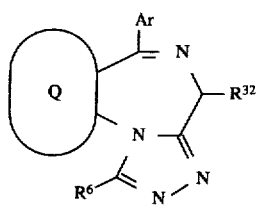

(VIII)

wherein each symbol is as defined above. The Compound (VII) and the Compound (VIII) are encompassed in the Compound (IIA).

The reaction of a compound of the formula (IV) with a compound of the formula (V) and elimination of protecting group are carried out according to the method described, for example, in "Pepuchido Gosei no Kiso to Jikken (Basic and Experiment of Peptide Synthesis)", Nobuo Izumiya, Maruzen or "Protective Groups in Organic Synthesis", T. W. Green & P. G. Wuts, John Willey & Sons, Inc. These known references teach various amino-protecting groups inclusive of the exemplified above and those are also usable in the present invention.

Method 2

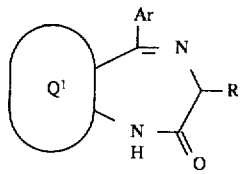

(IX)

wherein each symbol is as defined above.

For example, the above-mentioned Compound (IX) is reacted with a compound of the formula (X)

(X)

wherein Hal means halogen and other symbols are as defined above, in an inert solvent such as methanol, ethanol, propanol, isopropyl alcohol or dimethylformamide in the presence of sodium hydride, lithium hydride, potassium carbonate, sodium carbonate, sodium methoxide or sodium ethoxide to give a compound of the aforementioned formula (IIA).

A compound (IV') wherein $R^{15'}$ is alkyl having 8 to 15 carbon atoms or aralkyl, which is the starting compound (IIB), is produced by the following method.

Haloalkyl of the formula

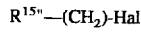

(XI)

wherein $R^{15''}$ is alkyl or aralkyl having a carbon number less 2 from that of the aforementioned $R^{15'}$, is reacted with triphenylphosphine in an inert solvent such as toluene, chloroform or tetrahydrofuran and thereto is added a base such as n-butyl lithium to give phosphorane. The phosphorane is reacted with p-nitrobenzaldehyde (Wittig reaction) to give a compound of the formula

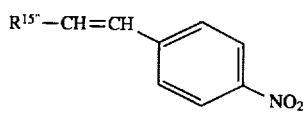

(XII)

wherein each symbol is as defined above. Then, the compound is subjected to reduction in the presence of an acid such as acetic acid or hydrochloric acid with 1–5 atm hydrogen to give a compound of the formula

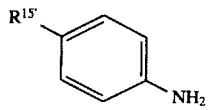

(XIII)

wherein each symbol is as defined above. Thereto are added benzonitrile, aluminum chloride and boron trichloride to allow reaction to give a compound of the formula

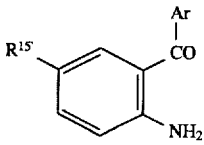

(IV')

wherein each symbol is as defined above.

Method 3

A compound of the formula (I) wherein W is —O—, and X and Y combinedly form =N—N=C($R^6$)—, which is represented by the formula

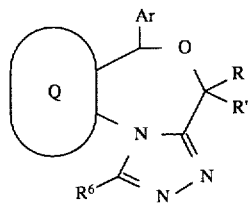 (1-a)

wherein each symbol is as defined above, is synthesized, for example, by the following methods.

Method A

An aminoketone of the formula

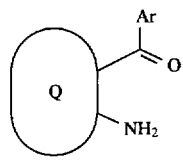 (8)

wherein each symbol is as defined above, is reacted with (a) a compound of the formula

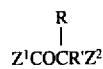 (9)

wherein $Z^1$ and $Z^2$ are the same or different and each is halogen such as chlorine or bromine and R and R' are as defined above, in a solvent such as acetone, tetrahydrofuran or dioxane under cooling, at room temperature or under heating to give an N-haloacetyl compound. The N-haloacetyl compound is reacted with potassium iodide or sodium iodide as necessary to convert same to an N-iodoacetyl compound which is then reacted with ammonia to give an N-glycyl compound of the formula

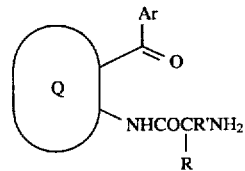 (10)

wherein each symbol is as defined above; or (b) a compound of the formula

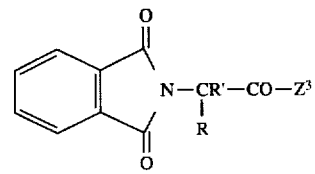 (11)

wherein $Z^3$ is halogen such as chlorine or bromine and R and R' are as defined above, to give an acetyl compound, followed by deprotection by a conventional method using hydrazine hydrate, etc. to give a compound of the formula (10).

The N-glycyl compound thus obtained is subjected to a ring closure reaction with dehydration in a solvent inert to the reaction, such as ethanol, propanol, isopropyl alcohol, butanol, benzene, toluene, dimethylformamide or dimethylacetamide, preferably in the presence of a weak acid catalyst such as acetic acid, propionic acid or silica gel at room temperature or under heating to give a compound of the formula

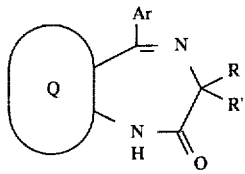 (12)

wherein each symbol is as defined above. A thionating agent is reacted with the compound of the formula (12) to give a compound of the formula

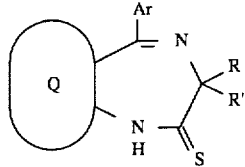 (13)

wherein each symbol is as defined above. Further, (a) a compound of the formula (13) is reacted with a compound of the formula $R^6CONHNH_2$ (14)

wherein $R^6$ is as defined above, to give a triazolodiazepine compound of the formula

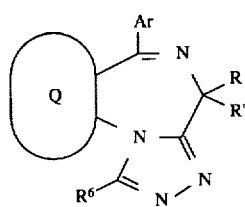 (3-a)

wherein each symbol is as defined above. Alternatively, (b) a compound of the formula

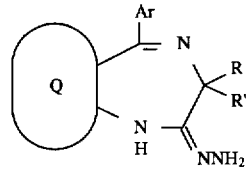 (15)

wherein each symbol is as defined above, which is obtained by reacting a compound of the formula (13) with a hydrazine hydrate, is reacted with a compound of the formula $R^6COOH$ (16)

wherein $R^6$ is as defined above, or a reactive derivative thereof or a compound of the formula $R^6C(OR^{62})_3$ (17)

wherein $R^{62}$ is alkyl having 1 to 5 carbon atoms such as methyl or ethyl and $R^6$ is as defined above, to give a compound of the formula (3-a).

In the above-mentioned methods, the thionating reagent may be, for example, phosphorus pentasulfide, Lawesson's reagent [2,4-bis(4-methoxyphenyl)1,3,2,4-dithiadiphosphetane-2,4-disulfide] or the like and the reactive derivative of the compound of the formula (16) may be, for example, carboxylic acid halide (carboxylic acid chloride, carboxylic acid bromide), carboxylic acid anhydride, mixed anhydride (lower alkyl carboxylic acid mixed anhydride, alkyl phosphoric acid mixed acid anhydride), lower alkyl ester (methyl ester, ethyl ester), activated ester (benzyl ester, p-nitrobenzyl ester, p-nitrophenyl ester, p-chlorophenyl ester) or the like.

The reaction of a compound of the formula (12) with a thionating reagent proceeds in a solvent inert to the reaction, such as pyridine, dimethylaniline, benzene, toluene, xylene, tetrahydrofuran, chloroform, dichloromethane, dioxane or mixed solvent thereof at 30°–100° C.

The reaction of a compound of the formula (13) with a compound of the formula (14) proceeds in a solvent inert to the reaction, such as benzene, toluene, xylene, tetrahydrofuran, dioxane, methanol, ethanol, propanol or isopropyl alcohol in the presence of an organic acid such as acetic acid or propionic acid, inorganic acid such as hydrochloric acid or sulfuric acid, or silica gel at room temperature to the refluxing temperature of the solvent used.

The reaction of a compound of the formula (13) with hydrazine or a hydrate thereof generally proceeds in a solvent inert to the reaction, such as methanol, ethanol, propanol, isopropyl alcohol, butanol or tetrahydrofuran at 0°–40° C.

The reaction of a compound of the formula (15) with a compound of the formula (16) or a reactive derivative thereof or a compound of the formula (17) proceeds in a solvent inert to the reaction, such as benzene, toluene, xylene, tetrahydrofuran or dioxane, preferably in the presence of an organic acid such as acetic acid or propionic acid, inorganic acid such as hydrochloric acid, sulfuric acid or phosphoric acid, or silica gel at room temperature to the refluxing temperature of the solvent used.

The obtained compound of the formula (3-a) is hydrolyzed with an inorganic acid such as hydrochloric acid or sulfuric acid and reacted with an aqueous solution of nitrous acid to give a compound of the formula

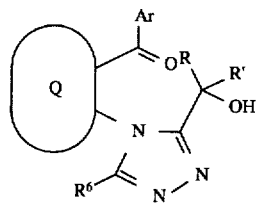

(4-a)

wherein each symbol is as defined above.

A compound of the formula (4-a) is dissolved in a suitable solvent such as methanol or ethanol and reduced with a suitable reducing agent such as sodium borohydride, sodium cyanoborohydride or lithium aluminum hydride to give a compound of the formula

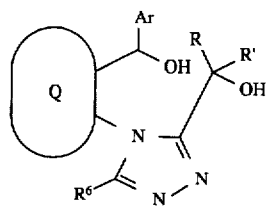

(18)

wherein each symbol is as defined above.

The compound of the formula (18) is subjected to a ring closure reaction with dehydration in an inert solvent such as benzene, toluene or xylene, preferably in the presence of a strong acid catalyst such as hydrochloric acid or sulfuric acid under heating to give a compound of the formula (1-a).

Method B

A compound of the formula (1-a) wherein $R^6$ is $R^{43}CONH(CH_2)a-$ wherein each symbol is as defined above is synthesized by the following method.

A compound of the formula (15) obtained by the Method A is reacted with a compound of the formula

$$Am(CH_2)aCOZ^4 \quad (19)$$

wherein Am is amine protected with a protecting group such as phthalimido, 2,3-diphenylmaleimido or dithiasuccinimido, $Z^4$ is halogen such as chlorine or bromine and a is as defined above, to give an acetyl compound.

The obtained acetyl compound is subjected to a ring closure reaction with dehydration in a solvent inert to the reaction, such as ethanol, propanol, isopopyl alcohol, butanol, benzene, toluene dimethylformamide or dimethylacetamide, preferably in the presence of a weak acid catalyst such as acetic acid, propionic acid or silica gel at room temperature or under heating, followed by deprotection by a conventional method to give a compound of the formula

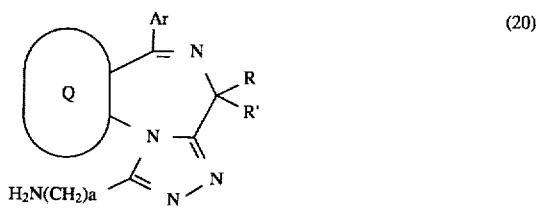

(20)

wherein each symbol is as defined above.

The obtained compound of the formula (20) is reacted with a compound of the formula

$$R^{43}COOH \quad (21)$$

wherein $R^{43}$ is as defined above, or a reactive derivative thereof in a solvent inert to the reaction, such as benzene, toluene, xylene, tetrahydrofuran or dioxane at room temperature to the refluxing temperature of the solvent used, to give a compound of the formula

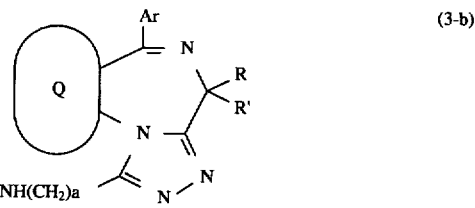

(3-b)

wherein each symbol is as defined above.

This compound is subjected to a series of reactions for forming a triazoloxazepine ring, as described in the Synthesis Method A for the compound of the formula (1-a) to give a triazole compound of the formula

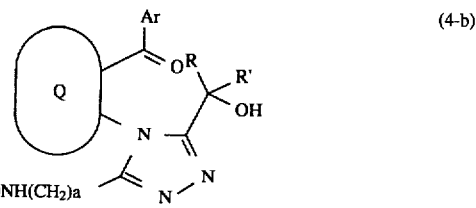

(4-b)

wherein each symbol is as defined above, from which the objective compound is obtained.

Method 4

A compound of the formula (I) wherein R is of the formula (3), (16) or (17) is produced by an addition reaction of isocyanate or isothiocyanate of the formula

$$R^{63}-N=C=Z \quad (XV)$$

wherein $R^{63}$ is $R^{11}$, $R^{12}$, —$CORa^{11}$ or —$SO_2Ra^{11}$, and $R^{11}$, $R^{12}$, $Ra^{11}$ and Z are as defined above, to a compound of the formula

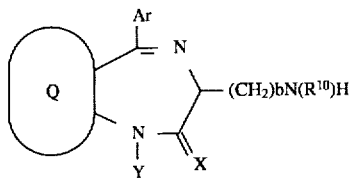 (XIV)

wherein each symbol is as defined above, or a compound of the formula (I) wherein R is of the formula (3) is produced by condensing a compound of the formula (XIV) with a compound of the formula $R^{11}COG$ (XVI)

wherein $R^{11}$ is as defined above and G is a leaving group such as hydroxy, halogen, ester (e.g. pentachlorophenoxy, p-nitrophenoxy) or thioester (e.g. phenylthio, 2,6-dimethylpyridine-4-thio).

The addition reaction of a compound of the formula (XIV) and a compound of the formula (XV) is carried out in a suitable solvent which does not interfere with the reaction. Examples of the solvent include organic solvents such as tetrahydrofuran, diethyl ether, diisopropyl ether, dioxane, dichloromethane, chloroform, carbon tetrachloride, ethyl acetate, benzene, toluene, xylene, dimethylformamide and dimethylacetamide. While the reaction temperature varies depending on the reagent and solvent to be used, it is generally from –20° C. to the boiling point of the solvent.

The condensation reaction of a compound of the formula (XIV) and a compound of the formula (XVI) is carried out in a suitable solvent according to the conventional peptide synthesis method as described in Method 1. Examples of the solvent include organic solvents such as tetrahydrofuran, diethyl ether, diisopropyl ether, dioxane, dichloromethane, chloroform, carbon tetrachloride, ethyl acetate, benzene, toluene, xylene, dimethylformamide and dimethylacetamide. Where necessary, the reaction is carried out in the presence of a base or a dehydrative condensing agent at a temperature of from –20° C. to the boiling point of the solvent.

Examples of the base to be used as necessary include alkaline metal hydroxides (sodium hydroxide, potassium hydroxide), alkaline metal carbonates (sodium carbonate, potassium carbonate), alkaline metal hydrogencarbonates (sodium hydrogencarbonate, potassium hydrogencarbonate), alkaline metal hydrides (sodium hydride) and organic base (triethylamine, pyridine, picoline, N-methylmorpholine). Where necessary, alkaline metal hydroxide may be used in two phases of the above-mentioned organic solvent and water by using a phase transfer catalyst such as tetrabutylammonium bromide or benzyltriethylammonium iodide. Examples of the dehydrative condensing agent include those used for amide synthesis, such as dicyclohexylcarbodiimide, N-ethyl-N'-(3-dimethylaminomethyl)carbodiimide hydrochloride, diphenylphosphoryl azide and N-methyl-2-chloropyridinium iodide.

Method 5

A compound of the formula (XIV) wherein b is 0, which is represented by the formula

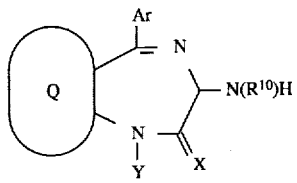 (XIV-1)

wherein each symbol is as defined above, can be obtained as follows.

A compound of the formula

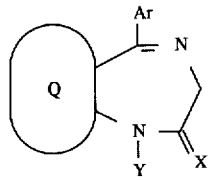 (XVII)

wherein each symbol is as defined above, is reacted with dialkyl carbonate such as diethyl carbonate in the presence of a base such as sodium hydride, potassium t-butoxide, lithium diisopropylamide or butyl lithium to introduce alkoxycarbonyl such as ethoxycarbonyl at the 6-position and the obtained compound is reacted with O-(2,4-dinitrophenyl)hydroxylamine to give a compound of the formula

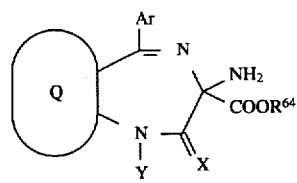 (XVIII)

wherein $R^{64}$ is alkyl such as ethyl and other symbols are as defined above, and the compound of the formula (XVIII) is subjected to hydrolysis in water or a mixed solvent of water and an organic solvent such as methanol, ethanol, diethyl ether, tetrahydrofuran or dioxane in the presence of a base such as sodium hydroxide, potassium hydroxide, barium hydroxide or lithium hydroxide at a temperature of from about 0° C. to the boiling point of the solvent used, and the obtained reaction mixture is subjected to decarboxylation by converting same to acidic with an acid such as hydrochloric acid, sulfuric acid, hydrobromic acid, trifluoroacetic acid or trifluoromethanesulfonic acid to give a compound of the formula

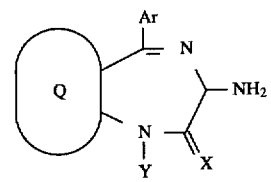 (XIX)

wherein each symbol is as defined above, and the obtained compound is reacted with an alkyl halide of the formula $R^{10}$-Hal (XX)

wherein Hal is halogen and $R^{10}$ is as defined above, in a suitable solvent such as diethyl ether, diisopropyl ether, tetrahydrofuran, dioxane, benzene, toluene, xylene or dimethylformamide in the presence of a base such as sodium hydride, potassium t-butoxide, lithium diisopropylamide, butyl lithium, pyridine, triethylamine, potassium carbonate, sodium carbonate or sodium hydrogencarbonate at a temperature of from −20° C. to the boiling point of the solvent used, or reacted with an aldehyde in the presence of a reducing agent such as sodium borohydride or sodium cyanoborohydride.

Method 6

A compound of the formula (XIV) wherein b is 1–6 is obtained as follows. After introducing alkoxycarbonyl in the same manner as in the case of the compound of the aforementioned formula (XVIII), a compound of the formula

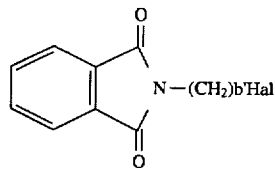
(XXI)

wherein b' is an integer of 1 to 6 and Hal is halogen, is reacted with the compound obtained in the above to give a compound of the formula

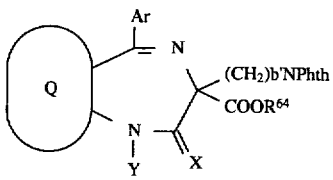
(XXII)

wherein Phth means phthaloyl and other symbols are as defined above, and the compound of the formula (XXII) is subjected to hydrolysis in water or a mixed solvent of water and an organic solvent such as methanol, ethanol, diethyl ether, tetrahydrofuran or dioxane in the presence of a base such as sodium hydroxide, potassium hydroxide, barium hydroxide or lithium hydroxide at a temperature of from about 0° C. to the boiling point of the solvent used, and the obtained reaction mixture is subjected to decarboxylation by converting same to acidic with an acid such as hydrochloric acid, sulfuric acid, hydrobromic acid, trifluoroacetic acid or trifluoromethanesulfonic acid, and the obtained compound is deprotected in a suitable solvent such as water, methanol, ethanol, isopropyl alcohol, tetrahydrofuran, dioxane or a mixed solvent thereof by adding hydrazine at a temperature of from about 0° C. to the boiling point of the solvent used to give a compound of the formula

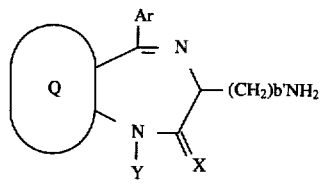
(XXIII)

wherein each symbol is as defined above, and the obtained compound is reacted with an alkyl halide of the formula (XX) in a suitable solvent such as diethyl ether, diisopropyl ether, tetrahydrofuran, dioxane, benzene, toluene, xylene or dimethylformamide in the presence of a base such as sodium hydride, potassium t-butoxide, lithium diisopropylamide, butyl lithium, pyridine, triethylamine, potassium carbonate, sodium carbonate or sodium hydrogencarbonate at a temperature of from −20° C. to the boiling point of the solvent used, or reacted with an aldehyde in the presence of a reducing agent such as sodium borohydride or sodium cyanoborohydride.

A compound of the formula (XXIII) wherein b' is 1, which is represented by the formula

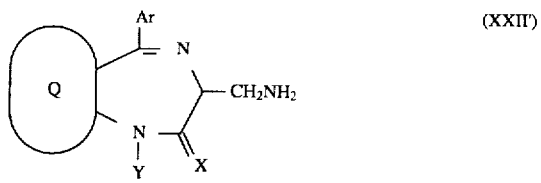
(XXII')

can be produced by the following method.

A compound of the formula

(IV)

wherein each symbol is as defined above, is condensed with 2,3-diaminopropionic acid wherein an amino group has been protected as necessary, according to the conventional peptide synthesis method described in Method 1 and deprotected to give a compound of the formula

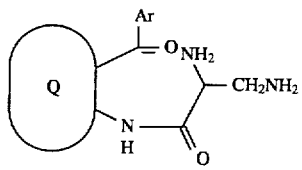

wherein each symbol is as defined, above and the amino at the 3-position may be protected as necessary. The obtained compound is subjected to a ring closure reaction with dehydration in an inert solvent such as ethanol, isopropanol, benzene or toluene in the presence of a weak acid such as acetic acid, propionic acid or silica gel at room temperature or under heating to give a compound of the formula

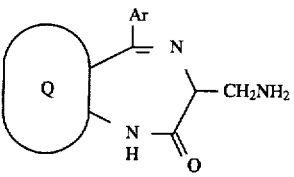

wherein each symbol is as defined above. According to the similar method as Method A in the aforementioned Method 3, a 5-membered ring can be formed in the obtained compound.

Method 7

A compound of the formula (XVII) wherein X and Y combinedly form =N—N=C($R^6$)— is produced by reacting a compound obtained according to Japanese Patent Unexamined Publication No. 79185/1989 or 156982/1989, which has the formula

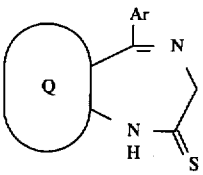
(XXIV)

wherein each symbol is as defined above, with a compound of the formula

R⁶CONHNH₂ (XXV)

wherein R⁶ is as defined above, or by reacting a compound obtained by reacting a compound of the formula (XXIV) with a hydrazine hydrate, which has the formula

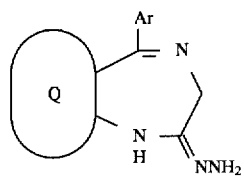
(XXVI)

wherein each symbol is as defined above, with a compound of the formula

R⁶COOH (XXVII)

wherein R⁶ is as defined above, or a reactive derivative thereof, or a compound of the formula

R⁶C(OR⁶⁵)₃ (XXVIII)

wherein R⁶⁵ is alkyl such as methyl or ethyl and R⁶ is as defined above.

The reaction of a compound of the formula (XXIV) with a hydrazine hydrate usually proceeds in a solvent inert to the reaction such as methanol, ethanol, propanol, isopropyl alcohol or butanol at 0°–40° C. for 5 minutes to 3 hours.

The reaction of a compound of the formula (XXVI) with a compound of the formula (XXVII) or a reactive derivative thereof or a compound of the formula (XXVIII) proceeds in a solvent inert to the reaction such as benzene, toluene, xylene, tetrahydrofuran, dioxane or a mixed solvent thereof in the presence of an organic acid such as acetic acid or propionic acid, an inorgnic acid such as hydrochloric acid or sulfuric acid, or silica gel at a temperature of from room temperature to the refluxing temperature of the solvent used for 30 minutes to 6 hours.

Method 8

A compound of the formula (XVII) wherein X and Y combinedly form =N—C(R⁵)=C(R⁶)— is produced by reacting a compound of the formula (XXIV) with a compound of the formula

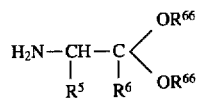
(XXIX)

wherein R⁶⁶ is alkyl such as methyl or ethyl, or aralkyl such as benzyl and R⁶ and R⁵ are as defined above.

The reaction usually proceeds in a solvent inert to the reaction such as methanol, ethanol, dioxane, dimethylformamide, tetrahydrofuran, benzene, toluene, xylene or a mixed solvent thereof in the presence of an acid catalyst such as mineral acid (e.g. hydrochloric acid, sulfuric acid, polyphosphoric acid), lower fatty acid (e.g. formic acid, acetic acid, propionic acid), or organic sulfonic acid (e.g. methanesulfonic acid, p-toluenesulfonic acid) at a temperature of from room temperature to 150° C., preferably while refluxing the solvent. When the acid catalyst itself which is used in the above reaction is liquid, it may act as a solvent. When a solvent is not used, the reaction is carried out at a temperature somewhat higher than the melting point of the compound of the formula (XVII), generally 150°–220° C.

Method 9

A compound of the formula

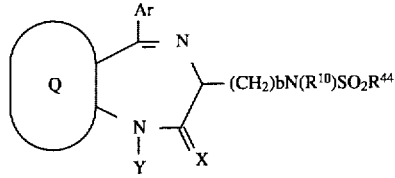
(Ib-3)

wherein each symbol is as defined above, can be obtained by reacting a compound of the formula

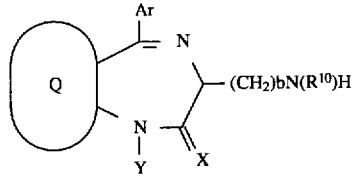
(IIb)

wherein each symbol is as defined above, with a sulfonyl halide of the formula

Hal-SO₂R⁴⁴ (IIIb)

wherein Hal is halogen such as chlorine and other symbols are as defined above, in an inert solvent such as dichloromethane, chloroform, benzene, toluene, carbon tetrachloride, tetrahydrofuran or dioxane in the presence of, where necessary, a base such as triethylamine, pyridine or N-methylmorpholine.

Method 10

A compound of the formula

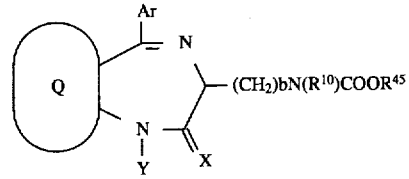
(Ib-4)

wherein each symbol is as defined above, is obtained by reacting a compound of the formula (IIb) with a halide of the formula Hal-COOR⁴⁵ (IVb)

wherein each symbol is as defined above, in an inert solvent such as chloroform, dichloromethane, benzene, toluene, dimethylformamide, tetrahydrofuran or dioxane.

Method 11

A compound of the formula

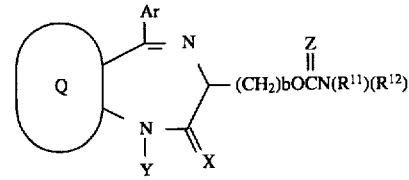
(Ib-5)

wherein each symbol is as defined above, is obtained by reacting a compound of the formula

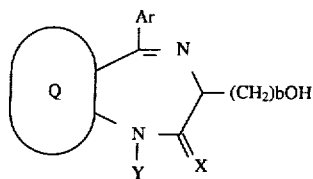

wherein each symbol is as defined above, with a halide of the formula

Hal-CZN(R$^{11}$)(R$^{12}$) (VIb)

wherein each symbol is as defined above, or an isocyanate or an isothiocyanate of the formula Z=C=N—R$^{67}$ (VIIb)

wherein R$^{67}$ is either R$^{11}$ or R$^{12}$, in an inert solvent such as dichloromethane, chloroform, benzene, toluene, dimethylformamide or carbon tetrachloride.

Method 12

A compound of the formula

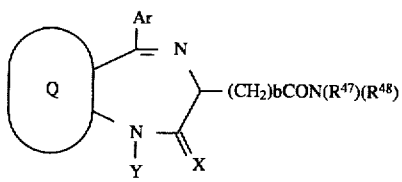

wherein each symbol is as defined above, is obtained by reacting a compound of the formula

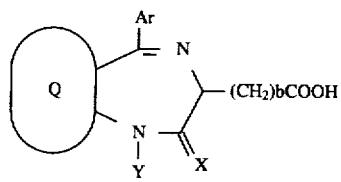

where in each symbol is as defined above, with a compound of the formula

HN(R$^{47}$)(R$^{48}$) (IXb)

where in each symbol is as defined above.

The reaction is carried out according to the conventional peptide synthesis method as previously described in Method 1, in a suitable solvent such as an organic solvent (e.g. tetrahydrofuran, diethyl ether, diisopropyl ether, dioxane, dichloromethane, chloroform, carbon tetrachloride, ethyl acetate, benzene, toluene, xylene, dimethylformamide or dimethylacetamide) in the presence of a base or a dehydrative condensing agent as necessary at a temperature of from −20° C. to the boiling point of the solvent. Examples of the base to be used as necessary include triethylamine, pyridine and N-methylmorpholine. The dehydrative condensing agent is preferably that conventionally used for peptide synthesis, such as dicyclohexylcarbodiimide, N-ethyl-N'-(3-dimethylaminomethyl)carbodiimide hydrochloride, diphenylphospholyl azide, N-methyl-2-chloropyridinium iodide or molecular sieves.

Method 13

A compound of the formula

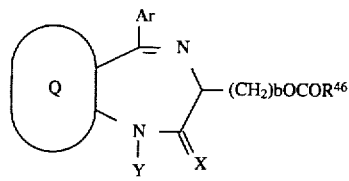

wherein each symbol is as defined above, can be obtained by reacting a compound of the formula (Vb) with an acid halide of the formula Hal-COR$^{46}$ (Xb)

wherein each symbol is as defined above, or an acid anhydride of the formula (R$^{46}$CO)$_2$O (XIb)

wherein each symbol is as defined above, in an inert solvent such as dichloromethane, chloroform, benzene, toluene, dimethylformamide or carbon tetrachloride.

Method 14

A compound of the formula

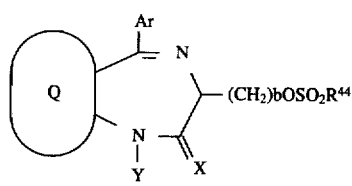

wherein each symbol is as defined above, can be obtained by reacting a compound of the formula (Vb) with a compound of the formula Hal-SO$_2$R$^{44}$ (XIIb)

where in each symbol is as defined above.

Method 15

A compound of the formula

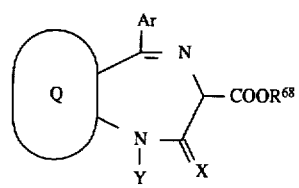

wherein R$^{68}$ is alkyl such as methyl or ethyl and other symbols are as defined above, is obtained by reacting a compound of the formula

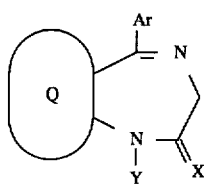

wherein each symbol is as defined above, with dialkyl carbonate such as diethyl carbonate in the presence of a base such as sodium hydride, potassium t-butoxide, lithium diisopropylamide or butyl lithium to introduce alkoxycarbonyl at the 3-position. Then, the compound is reacted with a halide of the formula Hal-(CH$_2$)bCOR$^{49}$ (XIVb)

wherein each symbol is as defined above, and the obtained compound of the formula

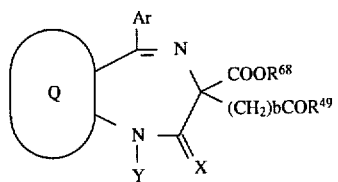

(XVb)

wherein each symbol is as defined above, is hydrolyzed in water or a mixed solvent of water and a suitable solvent such as methanol, ethanol, tetrahydrofuran or dioxane in the presence of a base such as sodium hydroxide, potassium hydroxide, sodium carbonate, potassium carbonate, sodium hydrogencarbonate or barium hydroxide at a temperature of from 0° C. to the boiling point of the solvent used, and then subjected to decarboxylation with an acid such as hydrochloric acid, sulfuric acid, hydrobromic acid, trifluoroacetic acid or trifluoromethanesulfonic acid to give a compound of the formula

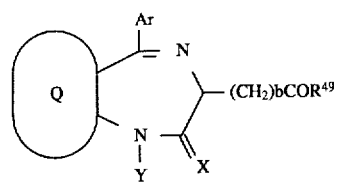

(Ib-9)

wherein each symbol is as defined above.

Method 16

A compound of the formula

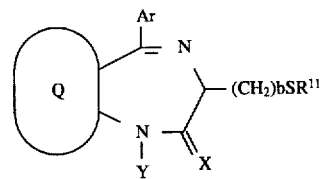

(Ib-10')

wherein each symbol is as defined above, is obtained by halogenating a compound of the formula (Vb) by reacting same with a halogenating agent such as phosphorus oxychloride, phosphorus tribromide, chlorine, bromine or N-bromosuccinimide in an inert solvent such as dichloromethane, chloroform, carbon tetrachloride, benzene, toluene, dioxane or dimethylformamide, and reacting the halogenated compound with thiol or thiolate of the formula $R^{11}SH$ or $R^{11}SNa$    (XVIb)

wherein $R^{11}$ is as defined above, in a suitable solvent such as methanol, ethanol, dimethylacetamide or dimethylformamide. The obtained compound is oxidized with an oxidizing agent such as hydrogen peroxide, potassium permanganate, sodium hypochlorite, ozone or ruthenium oxide in ethanol, methanol, acetic acid or a mixed solvent of acetic acid and water to give a compound of the formula

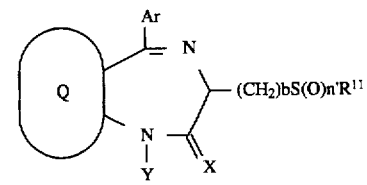

(Ib-10")

wherein n' is 1 or 2 and other symbols are as defined above.

Method 17

A compound of the formula

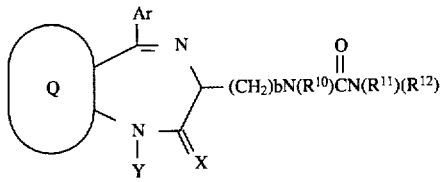

(D-I)

wherein each symbol is as defined above, is obtained by reacting a compound of the formula (IIb) with $COCl_2$ (phosgene) in an organic solvent such as toluene, chloroform or tetrahydrofuran in the presence of an organic base such as triethylamine at room temperature or under ice-cooling and 30 minutes to 1 hour later, adding an amine of the formula $HN(R^{11})(R^{12})$    (Ie)

wherein each symbol is as defined above.

Note that a compound of the formula (D-I) can be also obtained by reacting $COCL_2$ with a compound of the formula (Ie) and then with a compound of the formula (IIb).

In the same manner as above, a compound of the formula

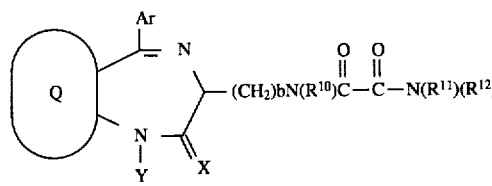

(D-II)

wherein each symbol is as defined above, is obtained by the use of $(COCl)_2$ (oxalyl chloride) in place of $COCl_2$ (phosgene).

Method 18

A compound of the formula

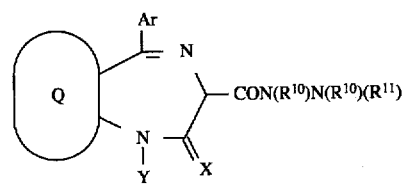

(D-III)

wherein each symbol is as defined above, is obtained by adding a hydrazine of the formula $HN(R^{10})N(R^{10})(R^{11})$ wherein $R^{10}$ and $R^{11}$ are as defined above, to a compound of the formula (XIIIb') in a polar solvent such as dimethyl sulfoxide or dimethylformamide at a temperature of from 0° C. to the boiling point of the solvent used.

Method 19

A compound of the formula

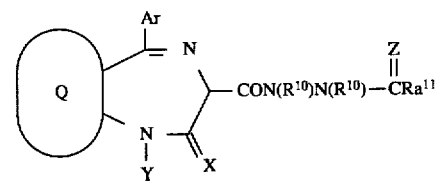

(D-IV)

wherein each symbol is as defined above, is obtained by adding an acid chloride of the formula $Cl-CZ-Ra^{11}$ wherein Ra$^{11}$ and Z are as defined above, to a compound of the formula (D-III) wherein R$^{11}$ is hydrogen in an inert solvent such as toluene, chloroform or tetrahydrofuran in the presence of an organic base such as triethylamine at a temperature of from 0° C. to the boiling point of the solvent used.

By a similar method, a compound of the formula

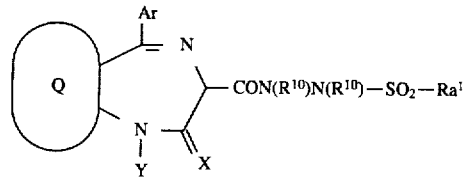
(D-V)

wherein each symbol is as defined above, is obtained by the use of Cl—SO$_2$—Ra$^{11}$ in place of Cl—CZ—Ra$^{11}$.

Method 20

A compound of the formula

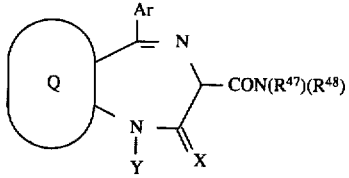
(D-VI)

wherein each symbol is as defined above, is obtained by reacting a compound of the formula (D-III) wherein R$^{11}$ is hydrogen with a nitrite such as isopentyl nitrite in a polar solvent such as dimethyl sulfoxide or dimethylformamide in the presence of an acid such as anhydrous hydrochloric acid at a temperature not more than $-10°$ C., preferably between $-40°$ C. and $-30°$ C., and 30 minutes to 1 hour later, reacting the obtained compound with an amine of the formula

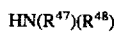
HN(R$^{47}$)(R$^{48}$)

wherein each symbol is as defined above, at a temperature not more than $-50°$ C., preferably not more than $-70°$ C., and gradually raising the temperature of the reaction mixture to 0° C. immediately thereafter.

Method 21

A compound of the formula

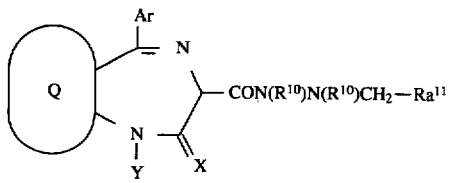
(D-VII)

wherein each symbol is as defined above, is obtained by reacting a compound of the formula (D-III) wherein R$^{11}$ is hydrogen with an alkyl halide of the formula

Ra$^{11}$-CH$_2$-Hal wherein each symbol is as defined above, in a suitable solvent such as diethyl ether, diisopropyl ether, tetrahydrofuran, dioxane, benzene, toluene, xylene or dimethylformamide in the presence of a base such as sodium hydride, potassium tert-butoxide, lithium diisopropylamide, butyl lithium, pyridine, triethylamine, potassium carbonate, sodium carbonate or sodium hydrogencarbonate at a temperature of from 20° C. to the boiling point of the solvent used, or with an aldehyde in the presence of a reducing agent such as sodium borohydride or sodium cyanoborohydride.

Method 22

A compound of the formula

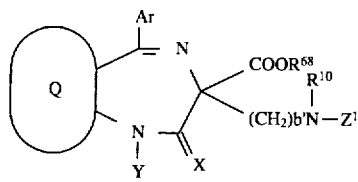
(D-VIII)

wherein each symbol is as defined above, is obtained by reacting a compound of the formula

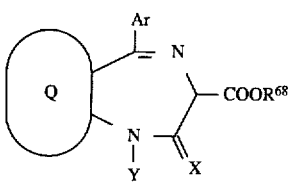
(XIIIb')

wherein each symbol is as defined above, with a compound of the formula

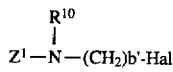
(D-VII)

wherein Z$^1$ is an amino-protecting group except phthaloyl, such as tert-butoxycarbonyl or benzyloxycarbonyl, or hydrogen, according to method 6. The protecting group Z$^1$ is eliminated by a conventional method and reacted with a compound of the formula

O=C=N—R$^{12}$ wherein R$^{12}$ is as defined above, according to Method 4 to give a compound of the formula

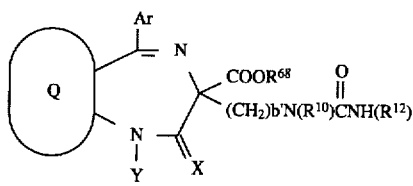
(D-IX)

wherein each symbol is as defined above. This compound is subjected to ring closure reaction, for example, by adding sodium hydride and raising the temperature of the reaction mixture to 70° C. to give a compound of the formula

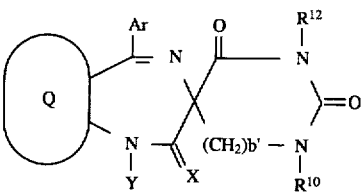
(D-X)

wherein each symbol is as defined above.

Method 23

A compound of the present invention having the following formula wherein the double bond between carbon and nitrogen is reduced can be obtained by a reduction method generally known, which is exemplified in the following.

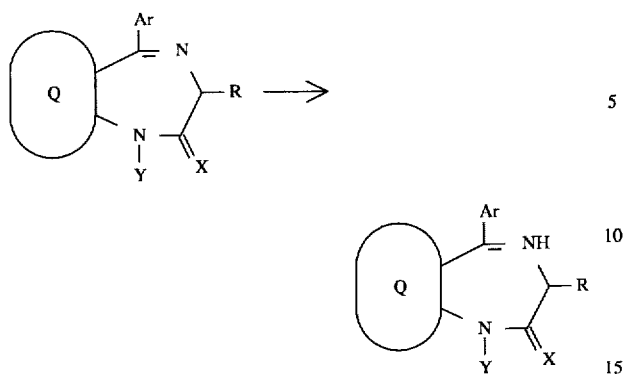

Exemplified are a method of catalytic hydrogenation with hydrogen in the presence of a metal catalyst such as Raney-nickel, palladium black or platinum oxide, a method by the use of a metal hydride such as sodium borohydride, sodium cyanoborohydride or lithium borohydride and a method by a reduction with formic acid or formalin, preferably with zinc in acetic acid.

Method 24

A compound of the formula (I) wherein W is —S— can be synthesized according to the method described in Japanese Patent Unexamined Publication No. 66585/1992.

[Production of Intermediate]

A compound of the formula (IIb) wherein b is 0 can be obtained by reacting a compound of the formula

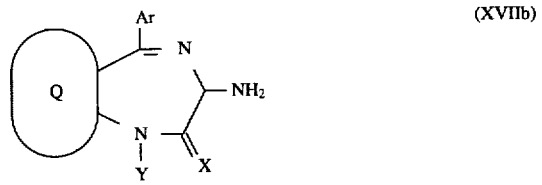
(XVIIb)

wherein each symbol is as defined above, which is obtained by the method described in Japanese Patent Unexamined Publication No. 28181/1990, with an alkyl halide of the formula

$R^{10'}$-Hal    (XVIIIb)

wherein $R^{10'}$ is $R^{10}$ other than hydrogen and Hal is as defined above, in a suitable solvent such as diethyl ether, diisopropyl ether, tetrahydrofuran, dioxane, benzene, toluene, xylene or dimethylformamide in the presence of a base such as sodium hydride, potassium tert-butoxide, lithium diisopropylamide, butyl lithium, pyridine, triethylamine, potassium carbonate, sodium carbonate or sodium hydrogencarbonate at a temperature of from −20° C. to the boiling point of the solvent used, or with an aldehyde in the presence of a reducing agent such as sodium borohydride or sodium cyanoborohydride.

A compound of the formula (IIb) wherein b is 1 to 6 can be synthesized by the following synthesis steps.

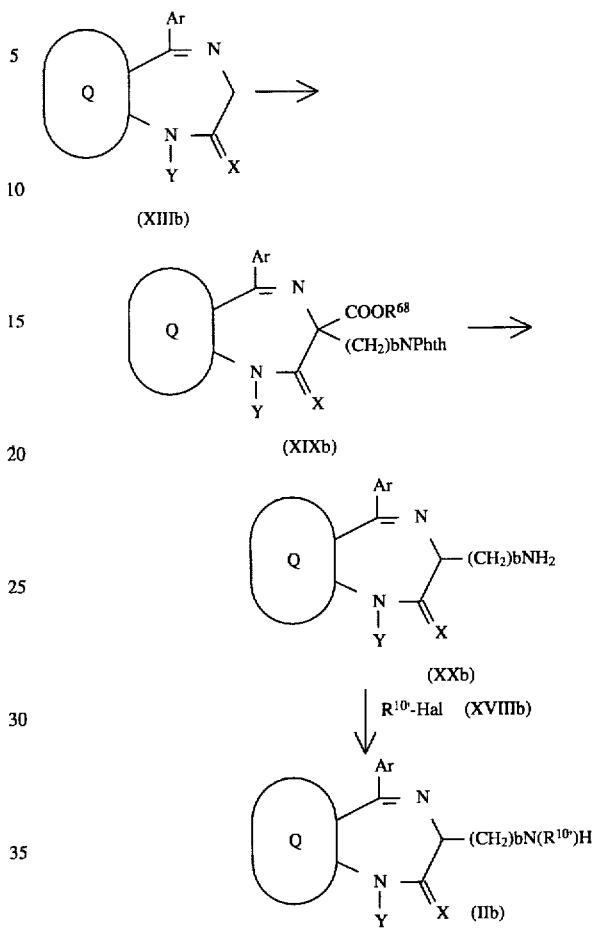

wherein $R^{68}$ is alkyl such as methyl or ethyl, Phth is phthaloyl and other symbols are as defined above.

A compound of the formula (XIIIb) is reacted with dialkyl carbonate such as diethyl carbonate in the presence of a base such as sodium hydride, potassium tert-butoxide, lithium diisopropylamide or butyl lithium to introduce alkoxycarbonyl group such as ethoxycarbonyl at the 3-position and the obtained compound is reacted with a halide of the formula: Hal(CH$_2$)aNPhth wherein Phth is phthaloyl and other symbols are as defined above, to give a compound of the formula (XIXb). The compound of the formula (XIXb) is hydrolyzed in water or a mixed solvent of water and an organic solvent such as, preferably, methanol, ethanol, diethyl ether, tetrahydrofuran or dioxane in the presence of a base such as sodium hydroxide, potassium hydroxide, barium hydroxide or lithium hydroxide at a temperature of from about 0° C. to the boiling point of the solvent used, and the obtained compound is subjected to decarboxylation by making the reaction mixture acidic with an acid such as hydrochloric acid, sulfuric acid, hydrobromic acid, trifluoroacetic acid or trifluoromethanesulfonic acid and then deprotected in a suitable solvent such as water, methanol, ethanol, isopropyl alcohol, tetrahydrofuran, dioxane or a mixed solvent thereof by adding hydrazine at a temperature of from about 0° C. to the boiling point of the solvent used to give a compound of the formula (XXb). The compound of the formula (XXb) is reacted with an alkyl halide of the formula (XVIIIb) in a suitable solvent such as diethyl ether, diisopropyl ether, tetrahydrofuran, dioxane, benzene, toluene, xylene or dimethylformamide in the presence of a base such as sodium hydride, potassium tert-butoxide, lithium diisopropylamide, butyl lithium, pyridine, triethylamine, potassium carbonate, sodium carbonate or sodium hydrogencarbonate at a temperature of from −20° C. to the boiling point of the solvent used, or with an aldehyde in the presence of a reducing agent such as sodium borohydride or sodium cyanoborohydride to give a compound of the formula (IIb).

A compound of the formula (Vb) wherein a is 0 can be synthesized by the following synthesis steps.

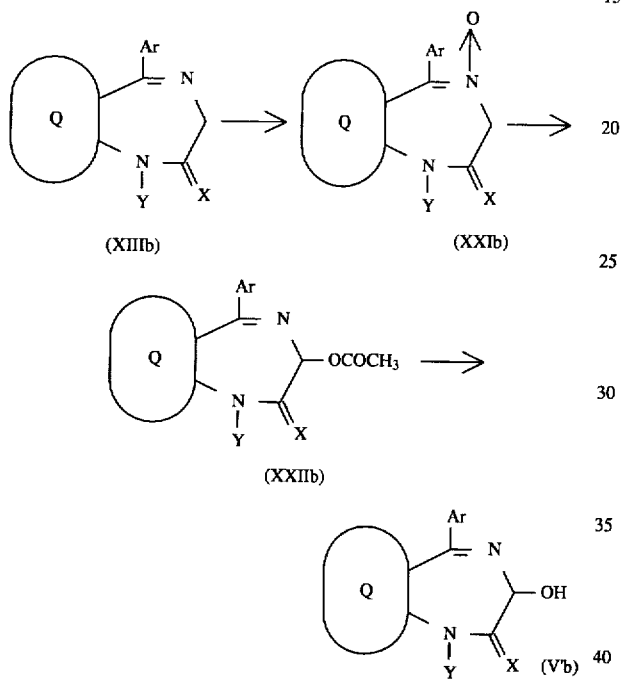

wherein each symbol is as defined above.

A compound of the formula (XIIIb) is converted to N-oxide (XXIb) with a peracid such as m-chloroperbenzoic acid, hydrogen peroxide or peracetic acid in an inert solvent such as chloroform, carbon tetrachloride, dichloroethane, benzene or toluene, and the N-oxide is subjected to Polonovski rearrangement in acetic anhydride to give a compound of the formula (XXIIb). The compound of the formula (XXIIb) is hydrolyzed by the reaction with a base such as sodium hydroxide, barium hydroxide or potassium hydroxide in a mixed solvent of water and a suitable organic solvent such as methanol, ethanol or isopropanol to give a compound of the formula (V'b).

A compound of the formula (Vb) wherein b is 1 to 6 can be obtained by introducing an alkoxycarbonyl at the 3-position of a compound of the formula (XIIIb) in the same manner as described above, reacting the obtained compound with a halide of the formula

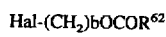 (XXIIIb)

wherein $R^{62}$ is alkyl such as methyl or ethyl and other symbols are as defined above, to give a compound of the formula

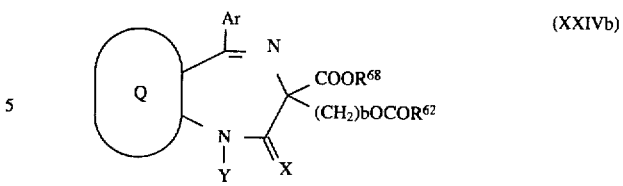

wherein each symbol is as defined above, and subjecting the compound to decarboxylation and hydrolysis as mentioned above.

A compound of the formula (IIb) or (Vb) wherein b is 1 to 6 can be also directly obtained by reacting a compound of the formula (XIIIb) with a compound of the formula: Hal-$(CH_2)$bNPhth or Q—$(CH_2)$bOCOR' wherein each symbol is as defined above, in an inert solvent such as tetrahydrofuran, dioxane, diethyl ether, benzene, toluene or dimethylformamide in the presence of a base such as sodium hydride, potassium tert-butoxide, lithium diisopropylamide or butyl lithium. The reaction generally proceeds at a temperature of from −50° C. to not more than 0° C. and the obtained compound is respectively deprotected and hydrolyzed to give a compound of the formula (IIb) or (Vb).

A compound of the formula (VIIIb) can be synthesized by the following synthesis steps.

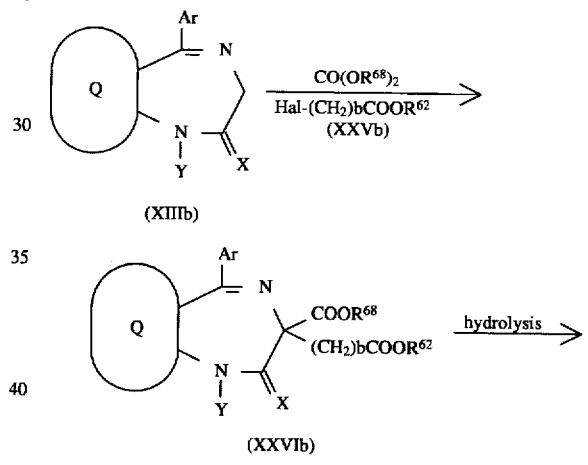

wherein each symbol is as defined above.

A compound of the formula (XIIIb) is reacted with dialkyl carbonate such as diethyl carbonate in the presence of a base such as sodium hydride, potassium tert-butoxide, lithium diisopropylamide or butyl lithium to introduce alkoxycarbonyl such as ethoxycarbonyl at the 3-position of diazepine ring and then reacted with a haloester of the formula

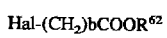

wherein $R^{62}$, Hal and b are as defined above, to give a compound of the formula (XXVIb). The compound of the formula (XXVIb) is hydrolyzed in water or a mixed solvent of water and a suitable solvent such as methanol, ethanol, tetrahydrofuran or dioxane in the presence of a base such as sodium hydroxide, potassium hydroxide, sodium carbonate, potassium carbonate, sodium hydrogencarbonate or barium hydroxide at a temperature of from 0° C. to the boiling point of the solvent used and the obtained compound is subjected to decarboxylation by converting the reaction mixture to acidic with an acid such as hydrochloric acid, sulfuric acid, hydrobromic acid, trifluoroacetic acid or trifluoromethanesulfonic acid to give a compound of the formula (VIIIb).

The compounds of the formula (I) thus obtained can be separated and purified from a reaction mixture by a method known per se such as recrystallization and column chromatography.

The compounds of the formula (I) thus obtained can be converted to pharmaceutically acceptable salts by a conventional method by treating with an inorganic acid such as hydrochloric acid, hydrobromic acid, sulfuric acid, phosphoric acid or nitric acid, an organic acid such as acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid or ascorbic acid, an inorganic base such as sodium hydroxide, potassium hydroxide, calcium hydroxide, magnesium hydroxide, zinc hydroxide or ammonium hydroxide, an organic base such as methylamine, diethylamine, triethylamine, dicyclohexylamine, triethanolamine, ethylenediamine, tris(hydroxymethyl)aminomethane, quinine, guanidine or cinchonine or an amino acid such as lysine, ornithine, arginine or alanine. The compounds of the formula (I) encompass hydrates and other solvates.

When the compounds of the present invention have chiral carbon atom, they can be usually obtained as racemates. The racemates can be resolved into optical isomers by conventional methods. Such optical isomers can be also produced by using optically active starting materials. Individual diastereomers can be purified by fractional crystallization or chromatography.

In the present invention, the compounds of the formula (I) encompass the following compounds.

Each symbol in Tables respectively denotes the following group. Me is methyl, Et is ethyl, Pr is propyl, OMe is methoxy, $c\text{-}C_3H_5$ is cyclopropyl, $c\text{-}C_5H_9$ is cyclopentyl, $c\text{-}C_6H_{11}$ is cyclohexyl, i-Bu is isobutyl, t-Bu is tert-butyl and Ph is phenyl.

TABLE 1

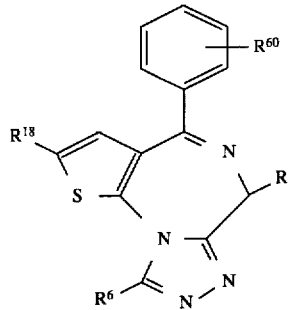

| compound No. | $R^{60}$ | $R^6$ | R | $R^{18}$ | mp. (°C.) |
|---|---|---|---|---|---|
| 1 | H | $CH_3$ | H | | 121–122 |
| 2 | 4-$CH_3$ | $CH_3$ | H | | 140–142 |
| 3 | 4-$OCH_3$ | $CH_3$ | H | | 124–126 |
| 4 | 4-Cl | $CH_3$ | H | | 165–167 |
| 5 | 3-Cl | $CH_3$ | H | | 156–158 |
| 6 | 2-Cl | H | H | | 98–100 |

TABLE 1-continued

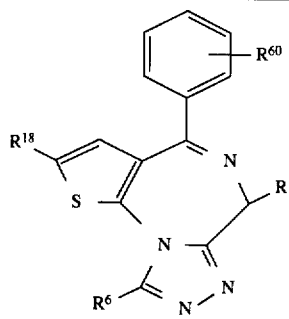

| compound No. | $R^{60}$ | $R^6$ | R | $R^{18}$ | mp. (°C.) |
|---|---|---|---|---|---|
| 7 | 2-Cl | $CH_3$ | H | 4-isobutyl-propyl-phenyl | 118–122 |
| 8 | 2-Cl | $C_2H_5$ | H | 4-isobutyl-propyl-phenyl | 115–116 |
| 9 | 2-Cl | $CH_3$ | $CH_3$ | 4-isobutyl-propyl-phenyl | 130–131 |
| 10 | 2-Cl | $CH_3$ | $C_2H_5$ | 4-isobutyl-propyl-phenyl | 97–99 |
| 11 | 2-Cl | $CH_3$ | H | 4-isobutyl-butyl-phenyl | 122–125 |
| 12 | 2-Cl | $CH_3$ | H | propyl-phenyl | 106–108 |
| 13 | 2-Cl | $CH_3$ | H | $C_4H_9$ | 107–109 |
| 14 | 2-Cl | $CH_3$ | H | $C_8H_{17}$ | 80–82 |

TABLE 2

(continued from Table 1)

| compound No. | $R^{60}$ | $R^6$ | R | $R^{18}$ | mp. (°C.) |
|---|---|---|---|---|---|
| 15 | 2-Cl | $CH_3$ | H | $C_{16}H_{33}$ | 58–60 |
| 16 | 2-Cl | $CH_3$ | $CH_3$ | $C_6H_{13}$ | 108–110 |
| 17 | 2-Cl | $CH_3$ | ◂$CH_3$ | 4-isobutyl-propyl-phenyl | 190–191.5 (p-toluen- sulfonate) |
| 18 | 2-Cl | $CH_3$ | ⋯$CH_3$ | 4-isobutyl-propyl-phenyl | 190–191.5 (p-toluen- sulfonate) |

TABLE 2-continued (continued from Table 1)

| compound No. | $R^{60}$ | $R^6$ | R | $R^{18}$ | mp. (°C.) |
|---|---|---|---|---|---|
| 19 | 2-Cl | $CH_3$ | H | morpholine-N-C(=O)-CH$_2$CH$_2$CH$_3$ | 187–189 |
| 20 | 2-Cl | $CH_3$ | $CH_3$ | morpholine-N-C(=O)-CH$_2$CH$_2$CH$_3$ | 162–163 |
| 21 | 2-Cl | $CH_3$ | H | $C_6H_{13}$ | 111–113 |
| 22 | 2-$CH_3$ | $CH_3$ | H | $C_6H_{13}$ | 135–137 |
| 23 | 2-$OCH_3$ | $CH_3$ | H | $C_6H_{13}$ | 128–130 |
| 24 | 2-$OCH_3$ | $CH_3$ | H | $C_8H_{17}$ | 76–78 |
| 25 | 2-$OCH_3$ | $CH_3$ | H | $C_{10}H_{21}$ | 90–92 |
| 26 | 2-$CH_3$ | $CH_3$ | H | $C_{10}H_{21}$ | 61–63 |
| 27 | 2-Cl | $CH_3$ | H | $C_{12}H_{25}$ | oily substance |
| 28 | 2-Cl | $CH_3$ | H | 4-isobutylphenyl-ethyl | 134–136 |
| 29 | 2-Cl | $CH_3$ | H | 4-octylphenyl-propyl | 112–114 |
| 30 | 2-F | $CH_3$ | H | 4-isobutylphenyl-propyl | 122–124 |
| 31 | 4-OH | $CH_3$ | H | 4-isobutylphenyl-propyl | 240–242 |
| 32 | 4-$OC_2H_4N(CH_3)_2$ | $CH_3$ | H | 4-isobutylphenyl-propyl | 122–125 |
| 33 | 2-Cl | isopropyl | $CH_3$ | 4-isobutylphenyl-propyl | 116–119 |

TABLE 2'

(continued from Table 1)

| compound No. | $R^{60}$ | $R^6$ | R | $R^{18}$ | mp. (°C.) |
|---|---|---|---|---|---|
| 34 | 2-Cl | t-Bu | $CH_3$ | 4-isobutylphenyl-propyl | 125–127 |
| 35 | 2-Cl | $C_3H_7$ | H | 4-isobutylphenyl-propyl | 74–77 |

TABLE 2'-continued (continued from Table 1)

| compound No. | $R^{60}$ | $R^6$ | R | $R^{18}$ | mp. (°C.) |
|---|---|---|---|---|---|
| 36 | 2-Cl | CH₃ | H | Ph₂CH-N(piperazine)-C(O)-CH₂CH₂CH₃ | 173–175 |
| 37 | 2-Cl | CH₃ | H | Ph₂CH-CH-(piperidine)-C(O)-CH₂CH₂CH₃ | 171–173 |
| 38 | 2-Cl | CH₃ | CH₃ | morpholine-C(O)-CH₂CH₂CH₃ | oily substance |
| 39 | 2-Cl | CH₃ | CH₃ | iBu-N(piperazine)-C(O)-CH₂CH₂CH₃ | oily substance |
| 40 | 2-Cl | CH₃ | CH₃ | morpholine-N-CH₂CH₂CH₂CH₃ | 183–184 |
| 41 | 2-Cl | CH₃ | CH₃ | CH₃N(piperazine)N-CH₂CH₂CH₂CH₃ | 195–196 |
| 42 | 4-Cl | CH₃ | n-propyl | 4-isobutylphenyl-CH(CH₃)- | 118–120 |
| 43 | 2-Cl | CH₃ | isobutyl | 4-isobutylphenyl-CH(CH₃)- | 109–111 |
| 44 | 2-Cl | CH₃ | phenyl | 4-isobutylphenyl-CH(CH₃)- | 170–172 |
| 45 | 4-Cl | CH₃ | n-butyl | 4-isobutylphenyl-CH(CH₃)- | 127–128 |
| 46 | 2-Cl | CH₃ | benzyl | 4-isobutylphenyl-CH(CH₃)- | oily substance |
| 47 | 2-Cl | CH₃ | H | C₂H₅ | 143–146 |
| 48 | 2-Cl | CH₃ | CH₃-NH-C(O)-(indole-2-yl) | C₂H₅ | 284–286 (decomposition) |

TABLE 2"

(continued from Table 1)

| compound No. | $R^{60}$ | $R^6$ | R | $R^{18}$ | mp. (°C.) |
|---|---|---|---|---|---|
| 49 | 2-Cl | $CH_3$ | N-methylindole-2-carboxamide | $C_2H_5$ | 259 |
| 50 | 2-Cl | $CH_3$ | N-methylbenzamide | $C_2H_5$ | 159–160 |
| 51 | 2-Cl | $CH_3$ | N-methyl-N'-(m-tolyl)urea | $C_2H_5$ | 250–252 |

TABLE 3

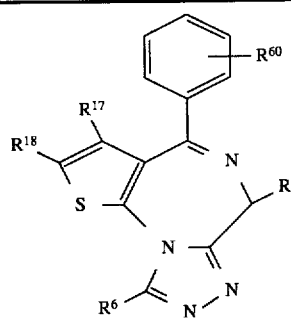

| compound No. | $R^{60}$ | $R^6$ | R | $(R^{17}, R^{18})$ ring formation | mp. (°C.) |
|---|---|---|---|---|---|
| 52 | 2-Cl | $CH_3$ | ◂$CH_3$ | cyclopropyl-C(O)-N-piperidinyl | 150 |
| 53 | 2-Cl | $CH_3$ | H | $(C_3H_7)_2NCO$-cyclopentyl | 136–139 |
| 54 | 2-Cl | $CH_3$ | $CH_3$ | morpholino-C(O)-cyclopentyl | oily substance |
| 55 | 2-Cl | $CH_3$ | $CH_3$ | morpholino-$CH_2$-cyclopentyl | 126–132 |
| 56 | 2-Cl | $CH_3$ | $CH_3$ | morpholino-C(O)-cyclohexyl | 232–238 |

TABLE 3-continued
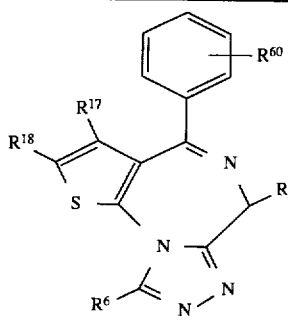
| compound No. | $R^{60}$ | $R^6$ | R | $(R^{17}, R^{18})$ ring formation | mp. (°C.) |
|---|---|---|---|---|---|
| 57 | 2-Cl | $CH_3$ | 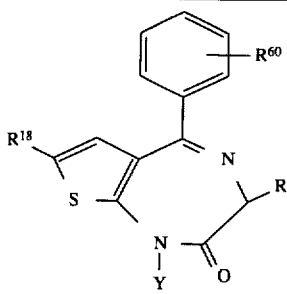 | | 304–306 (decomposition) |
TABLE 4
| compound No. | $R^{60}$ | Y | R | $R^{18}$ | mp. (°C.) |
|---|---|---|---|---|---|
| 58 | 2-Cl | H | H |  | 181–183 |
| 59 | 2-Cl | H | $CH_3$ | 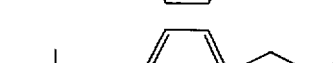 | 185–188 |
| 60 | 2-Cl | H | H | $C_6H_{13}$ | 141–143 |
| 61 | 2-Cl | H | $CH_3$ | $C_6H_{13}$ | 169–171 |
| 62 | 2-Cl |  | H | $C_8H_{17}$ | 117–118 (difumarate) |
| 63 | 2-Cl | 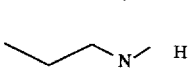 | H | $C_6H_{13}$ | 154–155 (difumarate) |
| 64 | 2-Cl | 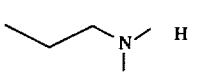 | H | 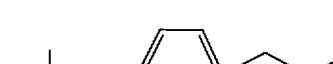 | 181–182.5 (oxalate) |

TABLE 4-continued
| compound No. | R[60] | Y | R | R[18] | mp. (°C.) |
|---|---|---|---|---|---|
| 65 | 2-Cl | 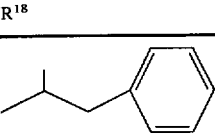 | CH₃ | 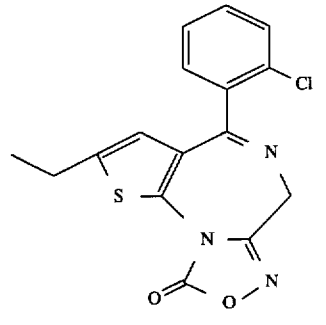 | 172–173 (oxalate) |
TABLE 5
| compound No. | compound | mp. (°C.) |
|---|---|---|
| 66 | 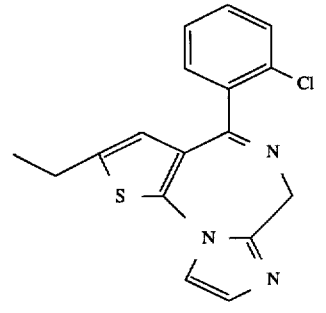 | 131–133 |
| 67 | | 124–127 |
| 68 | 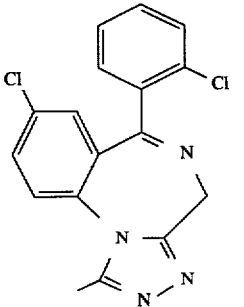 | 218–223 |

TABLE 5-continued

| compound No. | compound | mp. (°C.) |
|---|---|---|
| 69 | | 227–228 |
| 70 | | 164–165 |
| 71 | | 257–259 |

TABLE 6

| compound No. | R60 | R17 | R18 | R6 | R61 | mp. (°C.) |
|---|---|---|---|---|---|---|
| 72 | 4-Cl | H | Et | Me | 3-Me | 261–264 |
| 73 | 4-Cl | H | Et | Me | 2-Cl | 254–258 |
| 74 | 4-Cl | H | Et | Me | 3-Cl | 255–258 |
| 75 | 4-Cl | H | Et | Me | 4-Cl | 280–281 |
| 76 | 4-Cl | H | Et | Me | 3-OMe | 268–270 |
| 77 | 4-Cl | H | $C_6H_{13}$ | Me | 3-Cl | 254–255 |
| 78 | 4-Cl | H | hexyl | Me | 3-Me | 260–262 |
| 79 | 3-Cl | H | Et | Me | 3-Me | 267–270 |
| 80 | 2-Cl | H | 4-i-BuPh(CH2)2 | Me | 3-Me | 235 |
| 81 | 2-Cl | H | Et | Pr | 3-Me | 262–263 |
| 82 | 4-Cl | H | octyl | Me | 3-Me | 231–232 |
| 83 | 2-Cl | Me | Me | Me | 3-Me | 241–243 |

TABLE 6-continued

| compound No. | $R^{60}$ | $R^{17}$ | $R^{18}$ | $R^6$ | $R^{61}$ | mp. (°C.) |
|---|---|---|---|---|---|---|
| 84 | 2-Cl | H | Et | cyclohexyl | 3-Me | 259–260 |
| 85 | 2-Cl | H | Et | Me | 3-Me | 250–252 |
| 86 | 4-Me | H | Et | Me | 3-Me | 267–270 |
| 87 | 4-Cl | H | Et | Me | H | 274–276 |
| 88 | H | H | Et | Me | 3-Me | 272–274 |
| 89 | 2-Cl | —(CH$_2$)$_4$— | | Me | 3-Me | 241–243 |
| 90 | 4-Cl | H | Et | Me | 2-OMe | 250–251 |
| 91 | 2-Cl | H | Et | Me | 3-OMe | 269–272 |
| 92 | 2-Cl | H | Et | Me | 2-OMe | 271 |

TABLE 7

| compound No. | $R^{60}$ | $R^{17}$ | $R^{18}$ | $R^6$ | $R^{61}$ | Z | mp. (°C.) |
|---|---|---|---|---|---|---|---|
| 93 | 2-Cl | H | Et | Me | H | S | 212–214 |
| 94 | 4-Cl | H | Et | Me | 4-OMe | O | 279 |
| 95 | 2-Cl | H | Et | Me | 4-OMe | O | 260–262 |
| 96 | 4-Cl | H | Et | Me | 4-Br | O | 277–278 |
| 97 | 4-Cl | H | C$_4$H$_9$ | Me | 3-OMe | O | 243–245 |
| 98 | 4-Cl | H | C$_4$H$_9$ | Me | 3-Me | O | 259–260 |
| 99 | 4-Cl | H | C$_4$H$_9$ | Me | 2-OMe | O | 176–178 |
| 100 | 2-Cl | H | Et | cyclohexyl | 2-OMe | O | 269–271 |

TABLE 8

| compound No. | $R^{60}$ | $R^{17}$ | $R^{18}$ | Y | $R^{61}$ | mp. (°C.) |
|---|---|---|---|---|---|---|
| 101 | 2-Cl | H | Et | Me | 4-OMe | 201–203 |
| 102 | 2-Cl | H | Et | Me | 4-Cl | 241–243 |
| 103 | 2-Cl | H | Et | Me | 2-OMe | 224–225 |
| 104 | 2-Cl | H | Et | Me | H | 238–239 |
| 105 | 2-Cl | H | Et | Me | 3-Cl | 187–189 |
| 106 | 2-Cl | H | Et | Me | 2-OMe | 164–166 |
| 107 | 2-Cl | H | Et | Me | 4-Me | 228–229 |
| 108 | 2-Cl | H | Et | Me | 4-Br | 229–231 |
| 109 | 2-Cl | H | Et | Me | 2-Me | 166–167.5 |
| 110 | 2-Cl | H | Et | Me | 2-Cl | 173–175 |
| 111 | 2-Cl | H | Et | Me | 3-Me | 226–227 |

TABLE 9

| compound No. | compound | mp. (°C.) |
|---|---|---|
| 112 | (structure) | 176–178 |
| 113 | (structure) | 212–214 |
| 114 | (structure) | 196–199 |

TABLE 10

(structure with $R^{17}$, $R^{18}$, Ar, NHCONHR$^{12}$, $R^6$)

| compound No. | $R^{17}$ | $R^{18}$ | $R^6$ | $R^{12}$ | Ar | mp. (°C.) |
|---|---|---|---|---|---|---|
| 201 | H | Et | c-C$_6$H$_{11}$ | 4-MeO-Ph | 2-ClPh | 268–269 |
| 202 | H | Et | c-C$_6$H$_{11}$ | 2-ClPh | 2-ClPh | 260 |

TABLE 10-continued

| compound No. | R17 | R18 | R6 | R12 | Ar | mp. (°C.) |
|---|---|---|---|---|---|---|
| 203 | H | Et | c-C6H11 | 2-Me-phenyl | 2-ClPh | 265–266 |
| 204 | H | Et | c-C5H9 | 3-Me-phenyl | 2-ClPh | 246–247 |
| 205 | H | Et | c-C5H9 | 4-MeO-phenyl | 2-ClPh | 250–254 |
| 206 | H | Et | c-C3H5 | 4-MeO-phenyl | 2-ClPh | 249–251 |
| 207 | H | Et | c-C3H5 | 3-Me-phenyl | 2-ClPh | 270–272 |
| 208 | H | Et | c-C3H5 | 3-MeO-phenyl | 2-ClPh | 252–253 |
| 209 | H | Et | c-C5H9 | 2-MeO-phenyl | 2-ClPh | 270–272 |
| 210 | H | Et | c-C3H5 | 2-MeO-phenyl | 2-ClPh | 273–276 |
| 211 | H | Et | c-C6H11 | 4-Me-phenyl | 2-ClPh | 262–263 |
| 212 | H | Et | c-C6H11 | phenyl | 2-ClPh | 232–235 |
| 213 | H | Et | Ph | 2-MeO-phenyl | 2-ClPh | 268–270 |
| 214 | H | Et | c-C6H11 | 4-Cl-phenyl | 2-ClPh | 268–269 |

TABLE 11

(continued from Table 10)

| compound No. | R17 | R18 | R6 | R12 | Ar | mp. (°C.) |
|---|---|---|---|---|---|---|
| 215 | H | Et | c-C6H11 | 3-Cl-phenyl | 2-ClPh | 251–253 |
| 216 | H | Et | c-C6H11 | 3-MeO-phenyl | 2-ClPh | 233–236 |

TABLE 11-continued (continued from Table 10)

| compound No. | $R^{17}$ | $R^{18}$ | $R^6$ | $R^{12}$ | Ar | mp. (°C.) |
|---|---|---|---|---|---|---|
| 217 | H | Et | Ph | MeO—C₆H₄— (4-MeOPh) | 2-ClPh | 249–253 |
| 218 | H | Et | c-C₆H₁₁ | c-C₆H₁₁ | 2-ClPh | 257–260 |
| 219 | H | Et | (CH₃)₂CH— | 2-MeOPh | 2-ClPh | 279 |
| 220 | H | Et | butyl | 2-MeOPh | 2-ClPh | 260–261 |
| 221 | H | Et | butyl | 2-ClPh | 2-ClPh | 247–250 |
| 222 | H | Et | Me | Ph | 2-ClPh | 272–273 |
| 223 | H | Et | Me | 2-MePh | 2-ClPh | 254–255 |
| 224 | H | Et | Me | 4-MePh | 2-ClPh | 267–270 |
| 225 | H | Et | Me | 3-ClPh | 2-ClPh | 274–275 |
| 226 | H | Et | Me | 4-ClPh | 2-ClPh | 272–274 |
| 227 | H | Et | tert-butyl | 2-MeOPh | 2-ClPh | 278–279 |
| 228 | H | Et | Et | 2-MeOPh | 2-ClPh | 270–272 |

TABLE 11-continued (continued from Table 10)

| compound No. | $R^{17}$ | $R^{18}$ | $R^6$ | $R^{12}$ | Ar | mp. (°C.) |
|---|---|---|---|---|---|---|
| 229 | H | Et | Me | 2-Cl-phenyl | 2-ClPh | 273–276 |
| 230 | H | Et | tert-butyl | 3-Me-phenyl | 2-ClPh | 232–234 |

TABLE 11'

(continued from Table 10)

| compound No. | $R^{17}$ | $R^{18}$ | $R^6$ | $R^{12}$ | Ar | mp. (°C.) |
|---|---|---|---|---|---|---|
| 231 | H | Et | $(CH_3)_2CH-$ | 3-Me-phenyl | 2-ClPh | 266–267 |
| 232 | H | Et | Et | 3-Me-phenyl | 2-ClPh | 260–262 |
| 233 | H | Et | Et | 3-MeO-phenyl | 2-ClPh | 254–256 |
| 234 | H | Et | Pr | 2-MeO-phenyl | 2-ClPh | 269–270 |
| 235 | H | Et | $(CH_3)_2CH-$ | 3-MeO-phenyl | 2-ClPh | 250–252 |
| 236 | H | Et | butyl | 3-Me-phenyl | 2-ClPh | 229–231 |
| 237 | H | Et | $(CH_3)_2CH-$ | 4-MeO-phenyl | 2-ClPh | 254–255 |
| 238 | H | Et | tert-butyl | 4-MeO-phenyl | 2-ClPh | 251–254 |

TABLE 11'-continued
(continued from Table 10)
| compound No. | $R^{17}$ | $R^{18}$ | $R^6$ | $R^{12}$ | Ar | mp. (°C.) |
|---|---|---|---|---|---|---|
| 239 | H | Et | butyl | 4-MeO-Ph- | 2-ClPh | 251–253 |
| 240 | H | Et | Et | 4-MeO-Ph- | 2-ClPh | 262–263 |
| 241 | H | Me | Me | 2-MeO-Ph- | 2-ClPh | 255–257 |
| 242 | H | Et | Pr | 4-MeO-Ph- | 2-ClPh | 260–263 |
| 243 | H | Et | heptyl | 4-MeO-Ph- | 2-ClPh | 235–237 |
| 244 | H | Et | Me | cyclohexyl | 4-ClPh | 268–269 |
| 245 | H | Et | Me | 2,4-(MeO)$_2$-Ph- | 4-ClPh | 242–244 |
| 246 | H | Et | Me | 2,4-(MeO)$_2$-Ph- | 2-ClPh | 272–274 (decomposition) |
TABLE 12
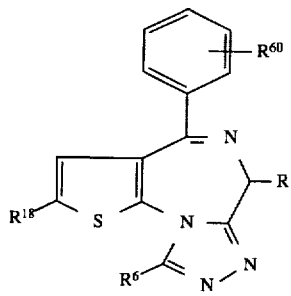
| compound No. | $R^{60}$ | $R^6$ | R | $R^{18}$ | mp. (°C.) |
|---|---|---|---|---|---|
| 247 | 4-Cl | Me | —CH$_2$COOH | Et | 198–202 |

TABLE 12-continued
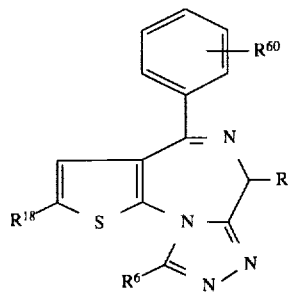
| compound No. | R⁶⁰ | R⁶ | R | R¹⁸ | mp. (°C.) |
|---|---|---|---|---|---|
| 248 | 4-Cl | Me | —CH₂CO—NH—(3-Me-phenyl) | Et | 247–248 |
| 249 | 4-Cl | Me | —CH₂CO—NH—(3-Cl-phenyl) | Et | 217–218 |
| 250 | 4-Cl | Me | —CH₂CO—NH—(2-MeO-phenyl) | Et | 198–200 |
| 251 | 4-Cl | Me | —CH₂CO—NH—phenyl | Et | 238–239 |
| 252 | 4-Cl | Me | —CH₂CO—NH—(3-OMe-phenyl) | Et | 244 |
| 253 | 2-Cl | Me | —NHSO₂—(4-Me-phenyl) | 4-iBu-C₆H₄—(CH₂)₂— | 158–162 |
| 254 | 4-Cl | Me | —NHSO₂—(4-Me-phenyl) | Et | 239–242 |
| 255 | 2-Cl | Me | —NHCOCH₂—phenyl | Et | 244 |
| 256 | 2-Cl | Me | —NHCOO—phenyl | Et | 158–159 |
| 257 | 4-OMe | Me | —OCONH—(3-Me-phenyl) | Et | 190–192 |

TABLE 13

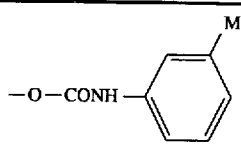

| compound No. | R⁶⁰ | Y | R | R¹⁸ | mp. (°C.) |
|---|---|---|---|---|---|
| 258 | 2-Cl | Me | —O—CONH—(3-Me-phenyl) | Et | 181–182.5 |

TABLE 13-continued

| compound No. | R⁶⁰ | Y | R | R¹⁸ | mp. (°C.) |
|---|---|---|---|---|---|
| 259 | 2-Cl | Me | —$CH_2COOH$ | Et | 228–231 |

TABLE 14

| compound No. | R⁶⁰ | R⁶ | R¹⁸ | R¹⁷ | mp. (°C.) |
|---|---|---|---|---|---|
| 301 | 4-OCH₃ | $C_{11}H_{23}$ | Et | H | 91–93 |
| 302 | 4-OH | $C_{11}H_{23}$ | Et | H | 96–98 |
| 303 | 4-CH₃ | $C_{17}H_{35}$ | Et | H | 83–84 |
| 304 | H | $C_{11}H_{23}$ | Et | H | oily substance |
| 305 | H | PhO(CH₂)₂— | Et | H | 75–78 |
| 306 | 2-Cl | $C_9H_{19}$ | —(CH₂)₄— | | 111–113 |
| 307 | 2-Cl | $C_{11}H_{23}$ | —(CH₂)₄— | | 65–67 |
| 308 | 2-Cl | $C_{15}H_{31}$ | —(CH₂)₄— | | 76–78 |
| 309 | 2-Cl | $C_{17}H_{35}$ | —(CH₂)₄— | | 73–74 |
| 310 | 2-Cl | $C_9H_{19}$ | CH₃ | CH₃ | 83–84 |
| 311 | 2-Cl | $C_{11}H_{23}$ | CH₃ | CH₃ | 93–95 |
| 312 | 2-Cl | $C_{15}H_{31}$ | CH₃ | CH₃ | 63–65 |
| 313 | 2-Cl | $C_{17}H_{35}$ | CH₃ | CH₃ | 93–95(HCl) |
| 314 | 2-Cl | 4-i-BuPh(CH₂)₃— | CH₃ | CH₃ | 115–117 |
| 315 | 2-Cl | $C_9H_{19}$ | Et | H | 113–114(HCl) |
| 316 | 2-Cl | $C_{11}H_{23}$ | Et | H | 88–89(HCl,¼H₂O) |
| 317 | 2-Cl | $C_{15}H_{31}$ | Et | H | 119–121(HCl) |
| 318 | 2-Cl | $C_{17}H_{35}$ | Et | H | 116–119(HCl) |
| 319 | 2-Cl | PhO(CH₂)₂— | Et | H | 126–128 |
| 320 | 3-Cl | PhO(CH₂)₂— | Et | H | 90–92 |
| 321 | 3-Cl | $C_9H_{19}$ | Et | H | 86–87 |
| 322 | 3-Cl | $C_{11}H_{23}$ | Et | H | 74–76 |
| 323 | 3-Cl | $C_{15}H_{31}$ | Et | H | 76–77 |
| 324 | 2-Cl | CH₃ | 4-i-BuPh(CH₂)₂— | H | 85–87 |
| 325 | 4-Cl | PhO(CH₂)₂— | Et | H | 128–130 |
| 326 | 4-Cl | $C_9H_{19}$ | Et | H | 130–131(½H₂O) |
| 327 | 4-Cl | $C_{11}H_{23}$ | Et | H | 107–108 |
| 328 | 4-Cl | $C_{15}H_{31}$ | Et | H | 115–117 |
| 329 | 4-Cl | $C_{17}H_{35}$ | Et | H | 108–109(H₂O) |
| 330 | 4-Cl | 4-i-BuPh(CH₂)₃— | Et | H | 108–109 |
| 331 | 4-Cl | —CH₂NHCOC₁₁H₂₃ | Et | H | 98–99 |
| 332 | 4-Cl | $C_{11}H_{23}$ | —(CH₂)₄— | | 158–160(HCl) |
| 333 | 4-Cl | $C_{15}H_{31}$ | —(CH₂)₄— | | 121–123(HCl) |

TABLE 14-continued

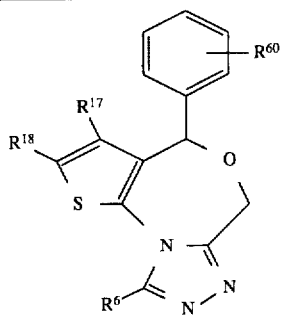

| compound No. | R$^{60}$ | R$^6$ | R$^{18}$ | R$^{17}$ | mp. (°C.) |
|---|---|---|---|---|---|
| 334 | 4-Cl | C$_{11}$H$_{23}$ | C$_8$H$_{17}$ | H | 78–81 |
| 335 | 4-Cl | C$_{15}$H$_{31}$ | C$_8$H$_{17}$ | H | 68–69 |
| 336 | 4-Cl | C$_{17}$H$_{35}$ | C$_8$H$_{17}$ | H | 65–66 |
| 337 | 4-Cl | CH$_3$ | C$_{16}$H$_{33}$ | H | 71–73 |
| 338 | 4-Cl | C$_4$H$_9$ | C$_{16}$H$_{33}$ | H | 135–137(HCl) |
| 339 | 4-Cl | C$_9$H$_{19}$ | C$_{16}$H$_{33}$ | H | 69–70 |
| 340 | 4-Cl | C$_{11}$H$_{23}$ | C$_{16}$H$_{33}$ | H | 60–62 |
| 341 | 4-Cl | C$_{15}$H$_{31}$ | C$_{16}$H$_{33}$ | H | 83–85 |
| 342 | 4-Cl | C$_{17}$H$_{35}$ | C$_{16}$H$_{33}$ | H | 90–92 |
| 343 | 2-OCH$_3$ | PhO(CH$_2$)$_2$— | Et | H | 120–121 |
| 344 | 2-OCH$_3$ | C$_{11}$H$_{23}$ | Et | H | 55–56 |
| 345 | 4-OCH$_3$ | PhO(CH$_2$)$_2$— | Et | H | 111–113 |
| 346 | 4-OCH$_3$ | C$_4$H$_9$ | Et | H | 101–103 |
| 347 | 4-OCH$_3$ | C$_5$H$_{11}$ | Et | H | 113–115 |
| 348 | 4-OCH$_3$ | C$_7$H$_{15}$ | Et | H | 106–108 |
| 349 | 4-OCH$_3$ | C$_9$H$_{19}$ | Et | H | 106–108 |
| 350 | 4-OCH$_3$ | C$_{15}$H$_{31}$ | Et | H | 93–95 |
| 351 | 4-OCH$_3$ | C$_{17}$H$_{35}$ | Et | H | 85–87 |
| 352 | 4-OCH$_3$ | C$_{11}$H$_{23}$ | C$_8$H$_{17}$ | H | 57–58 |
| 353 | 4-OCH$_3$ | C$_{15}$H$_{31}$ | C$_8$H$_{17}$ | H | 66–67(½H$_2$O) |
| 354 | 4-Me$_2$N(CH$_2$)$_2$O— | C$_{11}$H$_{23}$ | Et | H | 79–80(¼H$_2$O) |
| 355 | 2-CH$_3$ | CH$_3$ | C$_6$H$_{13}$ | H | oily substance |
| 356 | 2-CH$_3$ | PhO(CH$_2$)$_2$ | Et | H | 133–135 |
| 357 | 4-CH$_3$ | C$_{11}$H$_{23}$ | Et | H | 77–78 |
| 358 | 4-CH$_3$ | C$_{15}$H$_{31}$ | Et | H | 69–70 |
| 359 | 4-CH$_3$ | C$_{11}$H$_{23}$ | C$_8$H$_{17}$ | H | 71–73 |
| 360 | 4-OCH$_3$ | C$_4$H$_9$ | C$_{16}$H$_{33}$ | H | 56–57 |
| 361 | 4-OCH$_3$ | C$_{11}$H$_{23}$ | C$_{16}$H$_{33}$ | H | 56–58 |
| 362 | 4-OCH$_3$ | C$_7$H$_{35}$ | C$_{16}$H$_{33}$ | H | 79–81 |
| 363 | 4-Cl | C$_{11}$H$_{23}$ | Me | Me | 87–89 |
| 364 | 4-Cl | 4-i-BuPhCH$_2$— | Me | Me | 141–143 |
| 365 | 4-Cl | 4-i-BuPh(CH$_3$)$_3$— | Me | Me | 146–148 |
| 366 | 4-Cl | 4-i-BuPh(CH$_2$)$_4$— | Me | Me | 87–89 |
| 367 | 4-Cl | 4-i-BuPh(CH$_2$)$_5$— | Me | Me | 102–103 |

TABLE 15

| compound No. | R$^{60}$ | R$^6$ | R$^{15}$ | mp. (°C.) |
|---|---|---|---|---|
| 368 | 2-Cl | C$_{11}$H$_{23}$ | Cl | 124–125 |
| 369 | 2-Cl | C$_{15}$H$_{31}$ | Cl | 95–96 |
| 370 | H | C$_{11}$H$_{23}$ | H | 83–84 |

TABLE 16

| compound No. | compound | mp. (°C.) |
|---|---|---|
| 371 | 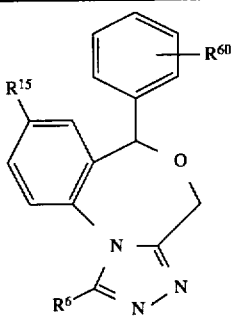 | 112–114 |

TABLE 17
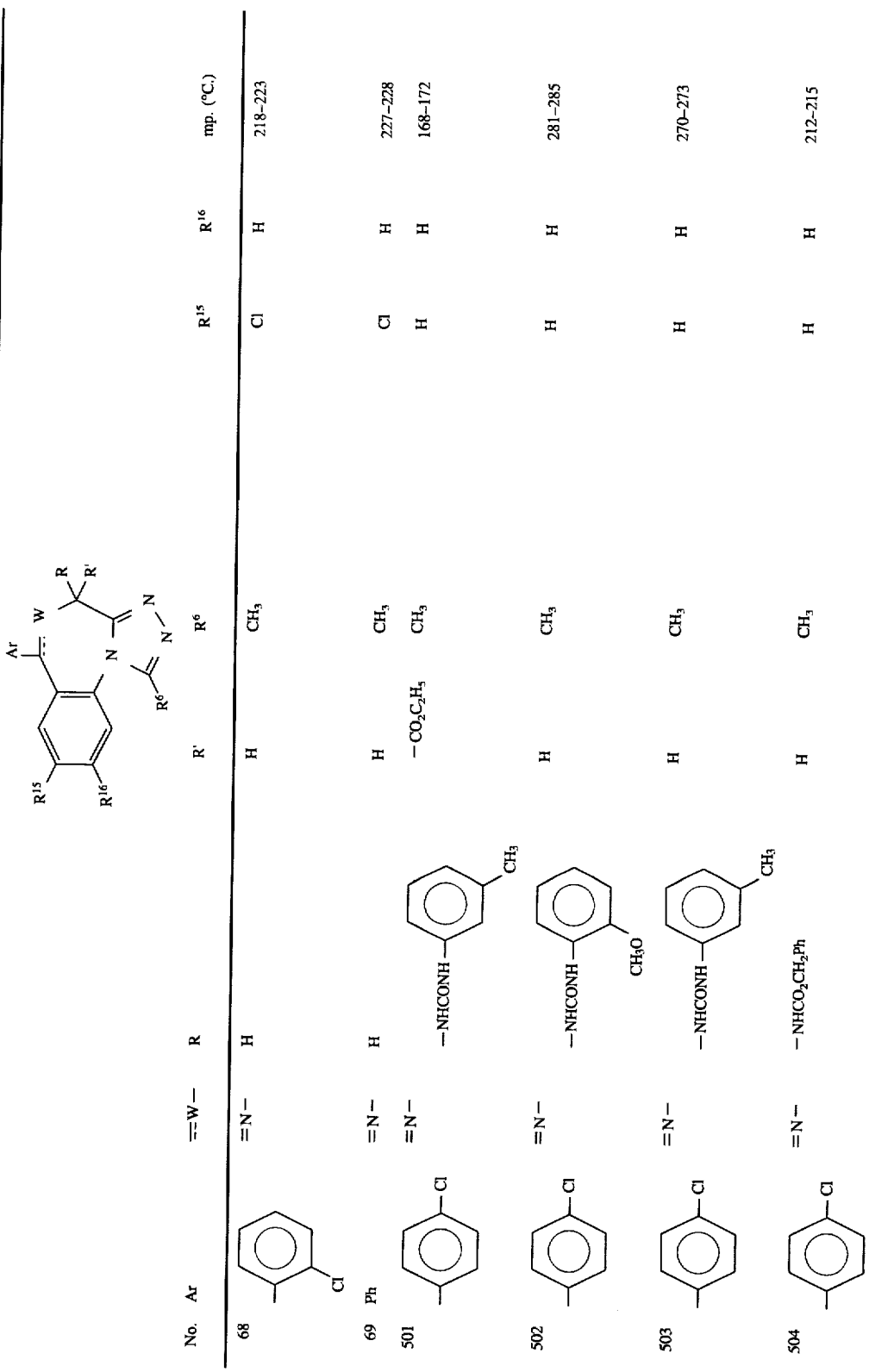
| No. | Ar | =W— | R | R' | R⁶ | R¹⁵ | R¹⁶ | mp. (°C.) |
|---|---|---|---|---|---|---|---|---|
| 68 | 2-Cl-Ph | =N— | H | H | CH₃ | Cl | H | 218–223 |
| 69 | 4-Cl-Ph | =N— | H | H | CH₃ | Cl | H | 227–228 |
| 501 | 4-Cl-Ph | =N— | —CO₂C₂H₅ | H | CH₃ | H | H | 168–172 |
| 502 | 4-Cl-Ph | =N— | —NHCONH-(3-CH₃-Ph) | H | CH₃ | H | H | 281–285 |
| 503 | 4-Cl-Ph | =N— | —NHCONH-(2-CH₃O-3-CH₃-Ph) | H | CH₃ | H | H | 270–273 |
| 504 | 4-Cl-Ph | =N— | —NHCO₂CH₂Ph | H | CH₃ | H | H | 212–215 |

TABLE 17-continued
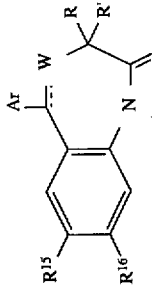
| No. | Ar | =W— | R | R' | R⁶ | R¹⁵ | R¹⁶ | mp. (°C.) |
|---|---|---|---|---|---|---|---|---|
| 505 | 4-Cl-C₆H₄ | =N— | —CH₂NHCONH-(2-OCH₃-C₆H₄) | H | CH₃ | H | H | 198–201 |
| 506 | 4-Cl-C₆H₄ | =N— | —CH₂NHCONH-(3-CH₃-C₆H₄) | H | CH₃ | H | H | 271–273 (decomp.) |
| 507 | 4-Cl-C₆H₄ | =N— | —NHSO₂CH₂Ph | H | CH₃ | H | H | 142–157 (amorphous) |
| 508 | 4-Cl-C₆H₄ | =N— | —CH₂-(indol-2-yl) | H | CH₃ | H | H | 275–279 |
| 509 | Ph | =N— | —CH₂OCONH-(2-OCH₃-C₆H₄) | H | CH₃ | H | H | 109–113 (amorphous) |
| 510 | Ph | =N— | —CH₂OCONH-(3-CH₃-C₆H₄) | H | CH₃ | H | H | 123–126 |

TABLE 17-continued

| No. | Ar | =W— | R | R' | R⁶ | R¹⁵ | R¹⁶ | mp. (°C.) |
|---|---|---|---|---|---|---|---|---|
| 511 | Ph | =N— | —CH₂OCOCH₂Ph | H | CH₃ | H | H | 61–67 (amorphous) |
| 512 | 4-Cl-C₆H₄ | =N— | H | H | n-C₇H₁₅ | H | H | 151–153 |
| 513 | 4-Cl-C₆H₄ | =N— | H | H | n-C₁₁H₂₃ | H | H | 97–98 |
| 514 | 4-Cl-C₆H₄ | =N— | H | H | n-C₁₅H₃₁ | H | H | 95–97 |
| 515 | 4-Cl-C₆H₄ | —NH— | H | H | n-C₁₁H₂₃ | H | H | 94–95 |
| 516 | 4-Cl-C₆H₄ | —O— | H | H | n-C₁₁H₂₃ | H | H | 87–89 |
| 517 | 4-Cl-C₆H₄ | =N— | H | H | 2,5-di-isobutyl-C₆H₃ | H | H | 63–65 |

TABLE 17-continued

| No. | Ar | =W— | R | R' | R⁶ | R¹⁵ | R¹⁶ | mp. (°C.) |
|---|---|---|---|---|---|---|---|---|
| 518 | Ph | =N— | —CH₂OSO₂-(4-CH₃-C₆H₄) | H | CH₃ | H | H | 100–104 (amorphous) |
| 519 | Ph | =N— | CH₃ | H | CH₃ | n-C₁₀H₂₁ | H | oily substance |
| 520 | Ph | =N— | CH₃ | H | CH₃ | H | n-C₁₀H₂₁ | 111–112 |
| 521 | 5-methyl-2-thienyl | =N— | —NHCONH-(3-CH₃-C₆H₄) | H | CH₃ | H | H | 263–265 |
| 522 | 4-Cl-C₆H₄ | =N— | —NHCONH-(2-pyridyl) | H | CH₃ | H | H | 274–278 |
| 523 | 4-Cl-C₆H₄ | =N— | —NHCONH-(3-pyridyl) | H | CH₃ | H | H | 272–274 |
| 524 | 4-Cl-C₆H₄ | =N— | —CONHNHCOPh | H | CH₃ | H | H | 243–245 |
| 525 | 4-Cl-C₆H₄ | =N— | —NHCONHCOPh | H | CH₃ | H | H | 231–233 |

TABLE 17-continued

| No. | Ar | =W— | R | R' | R⁶ | R¹⁵ | R¹⁶ | mp. (°C.) |
|---|---|---|---|---|---|---|---|---|
| 526 | 4-Cl-C₆H₄ | =N— | —NHCONHSO₂(4-CH₃-C₆H₄) | H | CH₃ | H | H | 212–214 |
| 527 | 4-Cl-C₆H₄ | =N— | —CONHNHPh | H | CH₃ | H | H | 175–177 |
| 528 | 4-Cl-C₆H₄ | =N— | —CONHOCH₂Ph | H | CH₃ | H | H | 138–139 |
| 529 | 4-Cl-C₆H₄ | =N— | —CONHCH₂Ph | H | CH₃ | H | H | 265–267 |
| 530 | 4-Cl-C₆H₄ | =N— | —NHCOCONHPh | H | CH₃ | H | H | 247–248 |
| 531 | 4-Cl-C₆H₄ | =N— | (cyclopropyl-C(=O)N(3-CH₃-C₆H₄)-C(=O)NH-) | | CH₃ | H | H | 269–271 |

TABLE 17-continued

| No. | Ar | =W— | R | R' | R⁶ | R¹⁵ | R¹⁶ | mp. (°C.) |
|---|---|---|---|---|---|---|---|---|
| 532 | Ph | =N— | —NHCONH-(2-CH₃O-C₆H₄) | H | CH₃ | Cl | H | 270–274 |
| 533 | Ph | =N— | —OCONH-(3-CH₃-C₆H₄) | H | CH₃ | Cl | H | 158–161 |
| 534 | Ph | =N— | —CH₂OC(CH₃)₃ | H | CH₃ | H | H | 202–206 |
| 535 | 4-Cl-C₆H₄ | =N— | —NHCONH—CH₂Ph | H | CH₃ | H | H | 270–273 |
| 536 | 4-Cl-C₆H₄ | =N— | —NHCONH-cyclohexyl | H | CH₃ | H | H | 257–259 |
| 537 | 4-Cl-C₆H₄ | =N— | —NHCO-(2-quinolinyl) | H | CH₃ | H | H | 287–290 |
| 538 | 4-Cl-C₆H₄ | =N— | —CONHNHSO₂-(4-CH₃-C₆H₄) | H | CH₃ | H | H | 285–287 |

TABLE 17-continued

| No. | Ar | =W— | R | R' | R⁶ | R¹⁵ | R¹⁶ | mp. (°C.) |
|---|---|---|---|---|---|---|---|---|
| 539 | 4-Cl-C₆H₄ | =N— | —CH₂NHCO-(1H-indol-2-yl) | H | CH₃ | H | H | 196–200 |
| 540 | 4-Cl-C₆H₄ | =N— | —NHCOCH₂-(3-methoxy-4-methylphenyl) | H | CH₃ | H | H | 133–137 |

TABLE 18

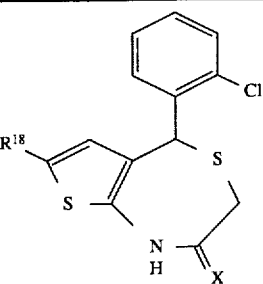

| compound No. | R¹⁸ | X | mp. (°C.) |
|---|---|---|---|
| 601 | H | O | 186–188 |
| 602 | Et | O | 181–183 |
| 603 | H | S | 178–179 |
| 604 | Et | S | |
| 605 | Br | S | |

TABLE 19

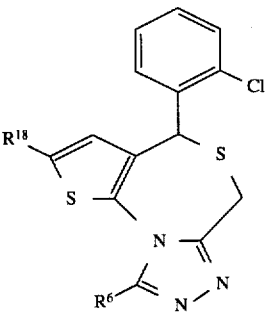

| compound No. | R¹⁸ | R⁶ | mp. (°C.) |
|---|---|---|---|
| 606 | H | Me | 212 |
| 607 | Et | Me | 159–161 |
| 608 | Br | Me | |

The method for determining the bone resorption-inhibitory activity of the Compound (I) and the results are shown in the following.

Bone resorption-inhibitory activity

The determination of the bone resorption-inhibitory activity basically followed the method of Raisz [J. Clin. Invest., vol. 44, pp. 103–116 (1965)].

A 1–2 days old new born ICR mouse was intraperitoneally administered with 1.5μ Ci $^{45}$Ca (CaCl$_2$ solution of isotope of calcium) and parietal bone was asceptically removed the next day. The parietal bone was split into two along the central sature line and one of them was used as a control and the other was used for the experiment. The bone was preincubated in 0.5 ml of a BGJb medium (Fitton-Jackson modification, GIBCO Laboratories, U.S.A.) added with the test compound to a concentration of 5 μM or 20 μM and bovine serum albumin (1 mg/ml) at 37° C. for 2 days, and further incubated in the aforementioned medium containing 50 nM hPTH (1–34) for 3 days. After the incubation, the radioactivity of $^{45}$Ca in the medium and in the bone was measured and the ratio (%) of $^{45}$Ca released from the bone into the medium was calculated.

Percent $^{45}$Ca released from the bone into the medium (%) =

$$\frac{^{45}\text{Ca count in the medium}}{^{45}\text{Ca count in the medium} + ^{45}\text{Ca count in the bone}} \times 100$$

Using the bone obtained from the same mouse and treated in the same manner without the test compound as a control, the ratio (%) against the control was calculated according to the following equation.

Ratio against the control (%) =

$$\frac{\text{ratio of }^{45}\text{Ca released from the experiment bone into the medium (\%)}}{\text{ratio of }^{45}\text{Ca released from the control bone into the medium (\%)}} \times 100$$

The average of these values obtained from four pairs from each group was calculated. The results are shown in Tables 20 and 21.

TABLE 20

| compound No. | concentration (μM) | bone resorption-inhibitory action, % against control |
|---|---|---|
| 1 | 20 | 30.7 |
| 5 | " | 26.7 |
| 6 | " | 30.2 |
| 9 | " | 23.7 (7.5) |
| 11 | " | 23.4 |
| 19 | " | 61.7 |
| 22 | " | 23.4 |
| 25 | " | 17.5 |
| 27 | " | 17.0 |
| 28 | " | 16.5 |
| 29 | " | 16.4 |
| 30 | " | 20.6 |
| 31 | " | 26.4 |
| 32 | " | 16.0 |
| 34 | " | 15.5 |
| 35 | " | 20.0 |
| 36 | " | 21.9 |
| 38 | " | 46.0 |
| 40 | " | 32.8 |
| 42 | " | 16.9 |
| 43 | " | 21.2 |
| 44 | " | 15.7 |
| 46 | " | 21.1 |
| 48 | " | 25.7 |
| 49 | " | 22.3 |
| 50 | " | 26.4 |
| 51 | " | 26.9 |
| 52 | " | 29.9 |
| 53 | " | 73.5 |
| 54 | " | 31.7 |
| 60 | " | 58.6 |
| 62 | " | 27.4 |
| 64 | 20 | 25.2 |
| 66 | " | 56.3 |
| 67 | " | 55.3 |
| 68 | " | 57.5 |
| 69 | " | 21.9 |
| 70 | " | 50.3 |
| 75 | 5 | 47.7 |
| 76 | " | 29.5 |
| 78 | " | 45.4 |
| 83 | " | 35.0 |
| 84 | " | 65.3 |
| 86 | " | 30.3 |
| 87 | " | 31.6 |
| 88 | " | 33.8 |
| 90 | " | 34.2 (0.25) |
| 93 | " | 63.5 |
| 98 | " | 35.0 |
| 100 | " | 55.5 |
| 112 | " | 54.8 |
| 250 | 20 | 27.3 |
| 254 | " | 32.5 |

TABLE 20-continued

| compound No. | concentration (μM) | bone resorption-inhibitory action, % against control |
|---|---|---|
| 255 | " | 54.3 |
| 257 | " | 27.1 |
| 302 | " | 22.4 |
| 304 | " | 28.6 |
| 307 | " | 42.4 |
| 324 | " | 33.1 |
| 330 | " | 35.6 |
| 348 | " | 30.3 |
| 354 | " | 23.2 |
| 357 | " | 24.7 |

Note:
The figures in parentheses show IC$_{50}$(μM).

TABLE 21

| compound No. | concentration (μM) | bone resorption-inhibitory action, % against control |
|---|---|---|
| 501 | 20 | 29.5 |
| 502 | " | 31.8 |
| 503 | " | 30.4 |
| 504 | " | 24.6 |
| 505 | " | 53.5 |
| 506 | " | 32.5 |
| 507 | " | 35.6 |
| 508 | " | 48.1 |
| 509 | " | 35.0 |
| 510 | " | 28.3 |
| 511 | " | 37.7 |
| 513 | " | 43.3 |
| 515 | " | 29.9 |
| 516 | 20 | 22.4 |
| 517 | " | 47.3 |
| 518 | " | 45.4 |
| 519 | " | 21.1 |
| 520 | " | 22.5 |
| 521 | " | 29.6 |
| 522 | " | 32.8 |
| 523 | " | 26.7 |
| 525 | " | 26.8 |
| 530 | " | 28.2 |
| 531 | " | 34.4 |
| 532 | " | 28.1 (0.93 |

Note:
The figures in parentheses show IC$_{50}$(μM).

The acute toxicity of the compounds of the present invention was examined using 6 male mice. The test compound was orally administered and the mice were observed for 5 days. As a result, no death case was found at the dose of 1000 mg/kg.

As demonstrated in the above, the compounds of the formula (I) of the present invention have superior bone resorption-inhibitory activity and are low toxic. It is evident from the results of the aforementioned bone resorption-inhibitory action test that these compounds have an action to reduce the increased amount of calcium in blood serum, which is caused by bone resorption. Accordingly, these compounds are usable as pharmaceutical agents to effectively inhibit bone resorption, to prevent decrease of bone mass and to prevent or suppress the increase of calcium amount in blood serum which is caused by the progress of bone resorption, with regard to Paget's disease, hypercalcemia, osteoporosis and so on in which the progress of bone resorption is considered to be deeply associated with the symptom, and to the symptoms of progressing bone resorption (development into osteoporosis) along with inflammatory joint diseases such as rheumatoid arthritis.

The compounds of the formula (I) and pharmaceutically acceptable salts thereof of the present invention are used as they are or as pharmaceutical compositions admixed with carrier, excipient and so on known per se such as lactose, starch, sucrose and magnesium stearate. The administration route may be oral or parenteral. The composition for oral administration may be solid or liquid. Specific examples include tablets, pills, granules, powders, capsules, syrups, emulsions and suspensions. Examples of the composition for parenteral administration include injections, suppositories, inhalations and percutaneous agents and the injections may be subcutaneous injections, intradermal injections or intramuscular injections. Such injections are prepared by a method known per se, by suspending or emulsifying the compound in a sterile aqueous solution such as physiological saline or isotonic solution or oily solution such as sesami oil or soy bean oil. Where necessary, a suitable suspending agent such as sodium carboxymethylcellulose or non-ionic surfactant, a solubilizer such as benzyl benzoate or benzyl alcohol, or the like may be added. While the dose varies depending on administration targets, administration route, symptom etc., it is generally 0.1–500 mg, preferably 0.1–100 mg daily for an adult.

The present invention is hereinbelow described in datail by way of examples and pharmaceutical examples. It should be understood that the present invention is not limited to these examples.

EXAMPLE 1

2-Amino-5-(2-(4-isobutylphenyl)ethyl)-3-(2-chlorobenzoyl)thiophene (4.7 g) was dissolved in chloroform (100 ml) and D,L-N-phthalylphenylalanyl chloride (4.7 g) was added thereto with stirring. The mixture was refluxed under heating for 10 hours. After cooling, the reaction mixture was washed with 5% aqueous solution of sodium hydrogencarbonate and water, and dried over anhydrous magnesium sulfate. The mixture was filtered and concentrated under reduced pressure. After the residue was purified by silica gel column chromatography, the objective fraction was concentrated under reduced pressure to give 4.2 g of 2-(N-phthalylphenylalanyl)amino-5-(2-(4-isobutylphenyl)ethyl)-3-(2-chlorobenzoyl)thiophene as an oily substance.

The compound (4.1 g) obtained as above was dissolved in methanol (50 ml) and hydrazine hydrate (0.9 g) was added thereto with stirring. The mixture was stirred at room temperature for 4 hours. Conc. hydrochloric acid (3 ml) was added thereto and the mixture was heated and stirred at 60° C. for 3 hours. The mixture was concentrated under reduced pressure. The residue was dissolved in chloroform (200 ml), washed with 5% sodium hydrogencarbonate and water, and dried over anhydrous magnesium sulfate. After filtration, the mixture was concentrated under reduced pressure. The obtained oily substance was dissolved in isopropyl alcohol (100 ml) and acetic acid (1.8 g) was added thereto. The mixture was heated and stirred at 75° C. for 20 hours. The reaction mixture was concentrated under reduced pressure. The residue was dissolved in chloroform, washed with 5% aqueous solution of sodium hydrogencarbonate and water, and dried over anhydrous magnesium sulfate. After filtration, the mixture was concentrated under reduced pressure and the residue was purified by silica gel column chromatography. The objective fraction was concentrated under reduced pressure to give 1.75 g of 5-(2-chlorophenyl)-7-(2-(4-isobutylphenyl)ethyl)1,3-dihydro-3-benzyl-2H-thieno[2,3-e][1,4]diazepin-2-one as an amorphous powder.

The compound (0.8 g) obtained as above was dissolved in chloroform (40 ml) and phosphorus pentasulfide (0.67 g) was added thereto with stirring. The mixture was refluxed under heating for 4 hours. After cooling, the mixture was washed with 5% sodium hydrogencarbonate and water, and dried over anhydrous magnesium sulfate. After filtration, the mixture was concentrated under reduced pressure and the residue was dissolved in tetrahydrofuran (40 ml). Hydrazine hydrate (0.2 g) was added thereto with stirring and the mixture was stirred for 1 hour. The reaction mixture was concentrated under reduced pressure and toluene (30 ml) was added to the residue. The mixture was dried over anhydrous magnesium sulfate and filtered. Ethyl orthoacetate (0.8 g) was added to the filtrate with stirring and the mixture was stirred while heating at 75° C. for 2 hours. The reaction mixture was concentrated under reduced pressure and the obtained oily substance was purified by silica gel column chromatography. The objective fraction was concentrated under reduced pressure to give 0.4 g of 4-(2-chlorophenyl)-2-(2-(4-isobutylphenyl)ethyl)-6-benzyl-9-methyl-6H-thieno[3,2-f][1,2,4]triazolo[4,3-a][1,4]diazepine as an amorphous powder.

EXAMPLE 2

2-Amino-5-(2-(4-isobutylphenyl)ethyl)-3-(2-chlorobenzoyl)thiophene (6.0 g) was dissolved in chloroform (100 ml) and D,L-N-phthalylphenylglycyl chloride (6.2 g) was added thereto with stirring. The mixture was refluxed under heating for 5 hours. After cooling, the reaction mixture was washed with 5% aqueous sodium hydrogencarbonate and water, and dried over anhydrous magnesium sulfate. The mixture was filtered and concentrated under reduced pressure. The residue was purified by silica gel column chromatography and the objective fraction was concentrated under reduced pressure to give 6.3 g of 2-(N-phthalylphenylglycyl)amino-5-(2-(4-isobutylphenyl)ethyl)-3-(2-chlorobenzoyl)thiophene as an oily substance.

Said compound (5.0 g) was dissolved in tetrahydrofuran (60 ml) and hydrazine hydrate (1.0 g) was added thereto with stirring and the mixture was stirred for 2 hours. Conc. hydrochloric acid (3 ml) was added thereto and the mixture was stirred while heating at 60° C. for 1 hour. The reaction mixture was concentrated under reduced pressure. The residue was dissolved in chloroform (200 ml), washed with 5% aqueous sodium hydrogencarbonate and water, and dried over anhydrous magnesium sulfate. After filtration, the residue was dissolved in isopropyl alcohol (120 ml). Acetic acid (2.3 g) was added thereto and the mixture was stirred while heating at 70°–75° C. for 40 hours. After cooling, the reaction mixture was concentrated under reduced pressure. The oily substance obtained was dissolved in chloroform (300 ml), washed with 5% aqueous sodium hydrogencarbonate and water, and dried over anhydrous magnesium sulfate. After filtration, the oily substance obtained was purified by silica gel column chromatography. The objective fraction was concentrated under reduced pressure and the residue was crystallized from isopropyl ether to give 0.4 g of 5-(2-chlorophenyl)-7-(2-(4-isobutylphenyl)ethyl)-1,3-dihydro-3-phenyl-2H-thieno[2,3-e][1,4]diazepin-2-one as colorless crystals, melting point 201°–203° C.

The aforementioned compound (0.35 g) was dissolved in chloroform (30 ml) and phosphorus pentasulfide (0.3 g) was added thereto with stirring. The mixture was refluxed under heating for 6.5 hours. After cooling, the reaction mixture was washed with water and 5% sodium hydrogencarbonate, and dried over anhydrous magnesium sulfate. After filtration, the filtrate was concentrated under reduced pressure and the residue was dissolved in tetrahydrofuran (20 ml). Hydrazine hydrate (0.2 g) was added thereto with stirring and the mixture was stirred for 1 hour. The reaction mixture was concentrated under reduced pressure and the residue was dissolved in toluene (20 ml). The mixture was dried over anhydrous magnesium sulfate and filtered. Ethyl orthoacetate (0.4 g) was added thereto with stirring and the mixture was stirred while heating at 80° C. for 2 hours. After cooling, the reaction mixture was concentrated and the oily substance obtained was purified by silica gel column chromatography. The objective fraction was concentrated under reduced pressure and the residue was crystallized from a mixture of isopropyl ether-n-hexane to give 0.12 g of 4-(2-chlorophenyl)-2-(2-(4-isobutylphenyl)ethyl)-6-phenyl-9-methyl-6H-thieno[3,2-f][1,2,4]triazolo[4,3-a][1,4]diazepine as colorless crystals, melting point 170°–172° C.

EXAMPLE 3

7-n-Octyl-5-(2-chlorophenyl)-2,3-dihydro-1H-thieno[2,3-e][1,4]diazepin-2-one (3.68 g) was dissolved in dry dimethylformamide (30 ml). In an ice bath, sodium hydride (60%, 0.5 g) and then dimethylaminoethyl chloride (1.3 g) were added thereto and the mixture was stirred at room temperature for 25 hours. The reaction mixture was poured into water (100 ml), extracted with ethyl acetate, and an organic layer was dried over anhydrous magnesium sulfate. After filtration, the oily substance obtained by concentration under reduced pressure was purified by silica gel column chromatography. The objective fraction was concentrated under reduced pressure and the residue (3.55 g) was dissolved in ethyl acetate (20 ml). A solution of fumaric acid (1.9 g) in ethanol (20 ml) was added thereto, and the mixture was allowed to stand. The obtained crystals were recrystallized from isopropyl alcohol to give 2.0 g of 7-n-octyl-5-(2-chlorophenyl)-1-(2-dimethylaminoethyl)1,3-dihydro-2H-thieno[2,3-e][1,4]diazepin-2-one difumarate as white crystals, melting point 117°–118° C.

Preparation of Starting Material 1

5-(2-Chlorophenyl)-7-ethyl1,3-dihydro-2H-thieno[2,3-e]-1,4-diazepin-2-one (40 g) was dissolved in chloroform (600 ml) and phosphorus pentasulfide (117 g) was added thereto with stirring. The mixture was refluxed for 3 hours. After the reaction, the reaction mixture was neutralized with saturated aqueous sodium bicarbonate, washed with water, and dried over anhydrous magnesium sulfate. The solvent was distilled away under reduced pressure and precipitated crystals were collected by filtration with diisopropyl ether and recrystallized from ethanol-chloroform to give 42 g of 5-(2-chlorophenyl)-7-ethyl-1,3-dihydro-2H-thieno[2,3-e]1,4-diazepine-2-thione having a melting point of 198°–199° C. The thione compound obtained (42 g) was suspended in methanol (300 ml) and 100% hydrazine hydrate (19 ml) was added thereto under cooling. The mixture was stirred at room temperature for 2 hours. After the reaction, the precipitated crystals were collected by filtration and recrystallized from ethanol-dimethylformamide to give 34 g of 5-(2-chlorophenyl)-7-ethyl-1,3-dihydro-2H-thieno[2,3-e]1,4-diazepine-2-hydrazine, melting point 214°–216° C. The hydrazone compound (20 g) was dissolved in chloroform (200 ml) and cyclohexylcarbonyl chloride (10 g) was added thereto with stirring. The mixture was stirred at room temperature for 1 hour. After the reaction, the reaction mixture was washed with a saturated aqueous solution of sodium bicarbonate and water, dried over anhydrous magnesium sulfate, and concentrated under reduced pressure. The residue obtained was dissolved in toluene (200 ml) and acetic acid (5.4 ml) was added thereto. The mixture was refluxed for 3 hours. After the completion of the reaction, the reaction mixture was washed with a saturated aqueous solution of sodium bicarbonate and water, and dried over anhydrous magnesium sulfate. The mixture was concentrated under reduced pressure and the residue was purified by silica gel column chromatography. The objective fraction was concentrated under reduced pressure to give 15 g of 4-(2-chlorophenyl)-9-cyclohexyl-2-ethyl-6H-thieno[3,2-f] [1,2,4]triazolo[4,3-a][1,4]diazepine, melting point 116°–119° C.

Preparation of Starting Material-2

4-(2-Chlorophenyl)-9-cyclohexyl-2-ethyl-6H-thieno[3,2-f][1,2,4]triazolo[4,3-a][1,4]diazepine (3.4 g) and sodium hydride (0.56 g) were added to diethyl carbonate (50 ml) and the mixture was heated. After refluxing for 1 hour, the reaction mixture was cooled to 20° C., and O-(2,4-dinitrophenyl)-hydroxylamine (2.1 g) was added thereto. The mixture was stirred for 2 hours. After the reaction, the reaction mixture was poured into ice water, and the diethyl carbonate layer was separated. The diethyl carbonate layer was washed twice with water, and dried over anhydrous magnesium sulfate. Diisopropyl ether was added to the residue obtained by distilling away diethyl carbonate under reduced pressure. The precipitated crystals were collected by filtration and recrystallized from ethyl acetate to give 2.1 g of ethyl(6-amino-4-(2-chlorophenyl)-9-cyclohexyl-2-ethyl-6H-thieno [3,2-f][1,2,4]triazolo[4,3-a][1,4]diazepin-6-yl)carboxylate having a melting point of 140°–145° C. Ethyl(6-amino-4-(2-chlorophenyl)-9-cyclohexyl-2-ethyl-6H-thieno[3,2-f][1, 2,4]triazolo[4,3-a][1,4]diazepin-6-yl)carboxylate (1.8 g) was dissolved in a mixture of ethanol (60 ml) and water (20 ml) and barium hydroxide 8 hydrate (1.14 g) was added thereto. The mixture was stirred at room temperature for 24 hours. The solvent was distilled away under reduced pressure and water (50 ml) was added thereto. The mixture was adjusted to pH 2 with 1N hydrochloric acid and stirred for 1 hour. The reaction mixture was neutralized with aqueous sodium hydrogencarbonate and extracted twice with chloroform. The organic layer was dried over anhydrous magnesium sulfate, and the solvent was distilled away under reduced pressure. The residue was purified by silica gel column chromatography. The solvent was distilled away and the crystals obtained were recrystallized from diisopropyl ether to give 1.0 g of 6-amino-4-(2-chlorophenyl)-9-cyclohexyl-2-ethyl-6H-thieno[3,2-f][1,2,4]triazolo[4,3-a][1,4]diazepine having a melting point of 175°–176° C.

Preparation of Starting Material-3

In the same manner as in Preparation of Starting Material-2, 6-amino-4-(2-chlorophenyl)-2-ethyl-9-phenyl-6H-thieno [3,2-f][1,2,4]triazolo[4,3-a][1,4]diazepine was obtained from 4-(2-chlorophenyl)-2-ethyl-9-phenyl-6H-thieno[3,2-f] [1,2,4]-triazolo[4,3-a][1,4]diazepine.

Preparation of Starting Material-4

In the same manner as in Preparation of Starting Material-2, 6-amino-4-(2-chlorophenyl)-9-cyclopentyl-2-ethyl-6H-thieno[3,2-f][1,2,4]triazolo[4,3-a][1,4]diazepine was obtained from 4-(2-chlorophenyl)-9-cyclopentyl-2-ethyl-6H-thieno[3,2-f][1,2,4]triazolo[4,3-a][1,4]diazepine.

Preparation of Starting Material-5

In the same manner as in Preparation of Starting Material-2, 6-amino-4-(2-chlorophenyl)-9-cyclopropyl-2-ethyl-6H-thieno[3,2-f][1,2,4]triazolo[4,3-a][1,4]diazepine was obtained from 4-(2-chlorophenyl)-9-cyclopropyl-2-ethyl-6H-thieno[3,2-f][1,2,4]triazolo[4,3-a][1,4]diazepine.

Preparation of Starting Material-6

4-(2-Chlorophenyl)-9-cyclohexyl-2-ethyl-6H-thieno[3,2-f][1,2,4]triazolo[4,3-a][1,4]diazepine (3.4 g) and sodium hydride (0.56 g) were added to diethyl carbonate (50 ml) and the mixture was heated. After refluxing for 1 hour, the reaction mixture was cooled to room temperature and 3-bromo-N-phthaloylpropylamine (2.3 g) was added thereto. The mixture was refluxed for 1 hour and the reaction mixture was poured into ice water. The diethyl carbonate layer was separated, washed twice with water, and dried over anhydrous magnesium sulfate. Diethyl carbonate was distilled away under reduced pressure and the residue was purified by silica gel column chromatography to give 2.4 g of ethyl(4-(2-chlorophenyl)-2-ethyl-9-cyclohexyl-6-(N-phthalylpropylamino)-6H-thieno[3,2-f][1,2,4]triazolo[4,3-a] [1,4]diazepin-6-yl)carboxylate. Ethyl(4-(2-chlorophenyl)-9-cyclohexyl-2-ethyl-6-(N-phthalylpropylamino)-6H-thieno [3,2-f][1,2,4]triazolo[4,3-a][1,4]diazepin-6-yl)carboxylate (2.4 g) was dissolved in a mixture of ethanol (60 ml) and water (20 ml) and barium hydroxide 8 hydrate (1.14 g) was added thereto. The mixture was stirred at room temperature for 24 hours. The solvent was distilled away under reduced pressure and water (50 ml) was added thereto. The mixture was adjusted to pH 2 with 1N hydrochloric acid. After stirring for 1 hour, the mixture was neutralized with aqueous sodium hydrogencarbonate and extracted twice with chloroform. The organic layer was dried over anhydrous magnesium sulfate and the solvent was distilled away under reduced pressure. The residue was dissolved in ethanol (50 ml), and hydrazine hydrate (1.25 g) was added thereto. The mixture was refluxed for 3 hours. After the reaction, ethanol was distilled away under reduced pressure and chloroform and water were added to the residue to allow precipitation of crystals. The crystals were filtered off and the chloroform layer was washed with a saturated aqueous solution of sodium bicarbonate. The chloroform layer separated was dried over anhydrous magnesium sulfate. The solvent was distilled away under reduced pressure and the residue was purified by silica gel column chromatography to give 1.2 g of 6-(3-aminopropyl)-4-(2-chlorophenyl)-9-cyclohexyl-2-ethyl-6H-thieno[3,2-f][1,2,4]triazolo[4,3-a][1,4]diazepine.

EXAMPLE 4

6-Amino-4-(2-chlorophenyl)-9-cyclohexyl-2-ethyl-6H-thieno[3,2-f][1,2,4]triazolo[4,3-a][1,4]diazepine (0.6 g) was dissolved in chloroform (15 ml) and 4-methoxyphenyl isocyanate (0.2 ml) was added thereto. The mixture was stirred for 30 minutes. The reaction mixture was purified by silica gel column chromatography and crystals obtained were recrystallized from methanol to give 0.49 g of N-(4-(2-chlorophenyl)-9-cyclohexyl-2-ethyl-6H-thieno[3,2-f][1,2,4] triazolo[4,3-a][1,4]diazepin-6-yl)-N'-(4-methoxyphenyl)urea having a melting point of 268°–269° C.

EXAMPLE 5

In the same manner as in Example 4, N-(2-chlorophenyl)-N'-(4-(2-chlorophenyl)-9-cyclohexyl-2-ethyl-6H-thieno[3, 2-f][1,2,4]triazolo[4,3-a][1,4]diazepin-6-yl)urea having a melting point of 260° C. was obtained from 6-amino-4-(2-chlorophenyl)-9-cyclohexyl-2-ethyl-6H-thieno[3,2-f][1,2,4]triazolo[4,3-a][1,4]diazepine and (2-chlorophenyl)-isocyanate.

EXAMPLE 6

In the same manner as in Example 4, N-(4-(2-chlorophenyl)-9-cyclohexyl-2-ethyl-6H-thieno[3,2-f][1,2,4]triazolo[4,3-a][1,4]diazepin-6-yl)-N'-(3-methylphenyl)urea having a melting point of 259°–260° C. was obtained from 6-amino-4-(2-chlorophenyl)-9-cyclohexyl-2-ethyl-6H-thieno[3,2-f][1,2,4]triazolo[4,3-a][1,4]diazepine and (3-chlorophenyl)isocyanate.

Reference Example 1

In a nitrogen atmosphere, 4-(4-chlorophenyl)-2-ethyl-9-methyl-6H-thieno[3,2-f][1,2,4]triazolo[4,3-a][1,4]diazepine (1 g) was dissolved in diethyl carbonate (35 ml) and 60% sodium hydride was added thereto at room temperature with stirring. After refluxing under heating for 2 hours, the reaction mixture was cooled to room temperature and ethyl bromoacetate (0.32 ml) was added thereto. After stirring at room temperature for 3 hours, the reaction mixture was poured into cold water and extraceted with ethyl acetate. The extract was washed with water, dried over anhydrous magnesium sulfate, filtered, and concentrated under reduced pressure. The residue was purified by silica gel column chromatography and the objective fraction was concentrated under reduced pressure. The residue concentrated was suspended in a mixture of ethanol (90 ml) and water (30 ml). To the suspension was added barium hydroxide 8 hydrate (0.65 g) at room temperature with stirring and the mixture was stirred at room temperature for 10 hours. The reaction mixture was concentrated under reduced pressure and water was added to the residue. The mixture was washed with ethyl acetate. The aqueous layer was adjusted to pH 2 with 6N hydrochloric acid and allowed to stand at room temperature overnight. The reaction mixture was neutralized with sodium hydrogencarbonate and extracted with ethyl acetate. The extract was dried over anhydrous magnesium sulfate and filtered. The filtrate was concentrated under reduced pressure and isopropyl ether was added for crystallization. As a result, 0.15 g of (4-(4-chlorophenyl)-2-ethyl-9-methyl-6H-thieno[3,2-f][1,2,4]triazolo[4,3-a][1,4]diazepin-6-yl)acetic acid (0.15 g) was obtained as pale brown crystals, melting point 198°–202° C.

Reference Example 2

5-(2-Chlorophenyl)-7-ethyl-1-methyl-2-oxo-1,3-dihydro-2H-thieno[2,3-e]-1,4-diazepin-3-yl)acetic acid having a melting point of 228°–231° C. was obtained from 5-(2-chlorophenyl)-7-ethyl-1-methyl-1,3-dihydro-2H-thieno[2,3-e]-1,4-diazepin-2-one by the same reaction and treatment as in Reference Example 1.

EXAMPLE 7

(4-(4-Chlorophenyl)-2-ethyl-9-methyl-6H-thieno[3,2-f][1,2,4]triazolo[4,3-a][1,4]diazepin-6-yl)acetic acid (2 g) obtained in Reference Example 1 was dissolved in dimethylformamide (50 ml), and aniline (0.59 ml), triethylamine (1.4 ml) and 1-hydroxybenzotriazole (0.75 g) were added thereto at room temperature with stirring. The mixture was cooled to 0° C. or below with stirring and N-ethyl-N'-(3-dimethylaminomethyl)carbodiimide hydrochloride (1.05 g) was added thereto. The mixture was heated to room temperature and allowed to stand overnight. The reaction mixture was poured into water and extrated with ethyl acetate. The organic layer was washed with 1N acetic acid, 1N sodium hydroxide and water, and dried over an hydrous magnesium sulfate. After filtration, the filtrate was concentrated under reduced pressure, and crystals obtained were recrystallized from ethanol to give 1.4 g of N-phenyl-(4-(4-chlorophenyl)-2-ethyl-9-methyl-6H-thieno[3,2-f][1,2,4]triazolo[4,3-a][1,4]diazepin-6-yl)acetamide having a melting point of 238°–239° C.

The following compounds were obtained in the same manner as above.

EXAMPLE 8

N-(3-Methylphenyl)-(4-(4-chlorophenyl)-2-ethyl-9-methyl-6H-thieno[3,2-f][1,2,4]triazolo[4,3-a][1,4]diazepin-6-yl)-acetamide, melting point 247°–248° C.

EXAMPLE 9

N-(3-Chlorophenyl)-(4-(4-chlorophenyl)-2-ethyl-9-methyl-6H-thieno[3,2-f][1,2,4]triazolo[4,3-a][1,4]diazepin-6-yl) acetamide, melting point 217°–218° C.

EXAMPLE 10

N-(2-Methoxyphenyl)-(4-(4-chlprophenyl)-2-ethyl-9-methyl-6H-thieno[3,2-f][1,2,4]triazolo[4,3-a][1,4]diazepin-6-yl)acetamide, melting point 198°–200° C.

EXAMPLE 11

N-(3-Methoxyphenyl)-(4-(4-chlorophenyl)-2-ethyl-9-methyl-6H-thieno[3,2-f][1,2,4]triazolo[4,3-a][1,4]diazepin-6-yl)acetamide, melting point 244° C.

EXAMPLE 12

6-Amino-4-(4-chlorophenyl)-2-ethyl-9-methyl-6H-thieno[3,2-f][1,2,4]triazolo[4,3-a][1,4]diazepine (1.6 g) was dissolved in chloroform (8 ml) and triethylamine (0.69 ml) was added thereto with stirring. p-Toluenesulfonyl chloride (0.94 g) was added thereto with stirring at room temperature and the mixture was refluxed under heating with stirring for 2 hours in an oil bath. After cooling, the reaction mixture was concentrated under reduced pressure and the residue was purified by silica gel column chromatography. The objective fraction was concentrated under reduced pressure and isopropyl ether was added to the residue for crystallization. As a result, 1.25 g of crystals of N-(4-(4-chlorophenyl)-2-ethyl-9-methyl-6H-thieno[3,2-f][1,2,4]triazolo[4,3-a][1,4]diazepin-6-yl)-p-toluenesulfonamide having a melting point of 239°–242° C. was obtained.

The following compound was obtained in the same manner as above.

EXAMPLE 13

N-(4-(2-Chlorophenyl)-2-(4-isobutylphenyl)ethyl-9-methyl-6H-thieno[3,2-f][1,2,4]triazolo[4,3-a][1,4]diazepin-6-yl)-p-toluenesulfonamide, melting point 158°–162° C.

EXAMPLE 14

5-(2-Chlorophenyl)-7-ethyl-1-methyl-1,3-dihydro-2H-thieno[2,3-e][1,4]diazepin-2-one (3 g) was dissolved in chloroform (60 ml) and m-chloroperbenzoic acid (4.3 g) was added thereto with stirring at room temperature. The mixture was further stirred for 8 hours. The reaction mixture was washed with 0.5N sodium hydroxide and water and dried over magnesium sulfate. After filtration, the filtrate was concentrated under reduced pressure and the residue obtained was dissolved in acetic anhydride (30 ml). The mixture was stirred while heating at 70° C. After cooling, the reaction mixture was poured into water and neutralized with sodium hydrogen-carbonate. After the mixture was extracted with ethyl acetate, the organic layer was washed with an aqueous solution of sodium hydrogencarbonate and water, and dried over anhydrous magnesium sulfate. After filtration, the filtrate was concentrated under reduced pressure, and the residue was dissolved in methanol (40 ml). A solution of sodium hydroxide (0.6 g) in water (10 ml) was added thereto at room temperature with stirring and the mixture was stirred at room temperature for 3 hours. The reaction mixture was concentrated under reduced pressure and water (50 ml) was added thereto. After the mixture was extracted with ethyl acetate, the organic layer was dried over anhydrous magnesium sulfate, filtered, and concentrated under reduced pressure. The residue obtained was purified by silica gel column chromatography to give 1.3 g of crude 5-(2-chlorophenyl)-7-ethyl-3-hydroxy-1-methyl-1,3-dihydro-2H-thieno[2,3-e][1,4]diazepin-2-one. This compound (0.7 g) was dissolved in toluene (20 ml) and 3-methylphenylisocyanate (0.31 g) was added thereto. The mixture was stirred for 2 days while heating at 90° C. After cooling, the reaction mixture was concentrated under reduced pressure and the residue was purified by silica gel column chromatography to give 0.25 g of (5-(2-chlorophenyl)-7-ethyl-1-methyl-oxo-1,3-dihydro-2H-thieno[2,3-e][1,4]-diazepin-3-yl)-N-(3-methylphenyl)carbamate having a melting point of 181°–182.5° C.

The following compound was obtained in the same manner as above.

EXAMPLE 15

(4-(4-Methoxyphenyl)-2-ethyl-9-methyl-6H-thieno[3,2-f][1,2,4]triazolo[4,3-a][1,4]diazepin-6-yl)-N-(3-methylphenyl)carbamate, melting point 190°–192° C.

Reference Example 3

4-Methoxycyanoacetophenone (89 g) and sulfur (16 g) were suspended in dimethylformamide (200 ml) and butyraldehyde (36.1 g) was added thereto under ice-cooling. Then, triethylamine (50.6 g) was added thereto and the mixture was allowed to react at 50°–55° C. for 1.5 hours with stirring. The reaction mixture was poured into ice water and extracted with ethyl acetate (1500 ml). The extract was washed with water and dried over anhydrous magnesium sulfate. After filtration, the filtrate was concentrated under reduced pressure and crystallized from hexane-isopropyl ether (4:1) to give 110 g of 2-amino-5-ethyl-3-(4-methoxybenzoyl)-thiophene as dark brown crystals.

The compound (110 g) obtained as above was dissolved in chloroform (400 ml) and chloroacetyl chloride (50.1 g) was added thereto with stirring. The mixture was refluxed for 1 hour under heating with stirring. After cooling, the reaction mixture was washed with 5% aqueous sodium hydrogencarbonate and water, and dried over anhydrous magnesium sulfate. After filtration, the filtrate was concentrated under reduced pressure and crystallized from isopropyl ether to give 125 g of 2-chloroacetylamino-5-ethyl-3-(4-methoxybenzoyl)thiophene as brown crystals.

Said chloroacetyl compound (125 g) and sodium iodide (62 g) were suspended in tetrahydrofuran (500 ml) and the suspension was refluxed for 2 hours under heating with stirring. The reaction mixture was cooled to −50° C. and liquid ammonia (ca. 100 ml) was added thereto at once with stirring. The temperature of the reaction mixture was raised to room temperature over 2 hours. After removing ammonia with an aspirator, the reaction mixture was concentrated under reduced pressure and the residue was dissolved in isopropyl alcohol (500 ml). Thereto was added acetic acid (26.7 g) and the mixture was refluxed for 14 hours under heating with stirring. After concentration under reduced pressure, the residue was dissolved in chloroform (500 ml), and washed with 5% aqueous sodium hydrogencarbonate and saline, and dried over anhydrous magnesium sulfate. After filtration, the filtrate was concentrated under reduced pressure and the residue was crystallized from isopropyl ether-ethyl acetate (5:1) to give 52 g of 7-ethyl1,3-dihydro-5-(4-methoxyphenyl)thieno[2,3-e][1,4]diazepin-2-one as yellow crystals.

The diazepine compound (52 g) obtained as above was dissolved in dichloromethane (500 ml), and phosphorus pentasulfide (46 g) was added thereto. The mixture was refluxed for 3 hours under heating with stirring. After cooling, the reaction mixture was washed with 5% aqueous sodium hydrogencarbonate and water, and dried over anhydrous magnesium sulfate. After filtration, the filtrate was concentrated under reduced pressure to give 7-ethyl-5-(4-methoxyphenyl)-1,3-dihydro-2H-thieno[2,3-e][1,4]diazepine-2-thione as an oily substance.

The thione compound obtained as above was suspended in methanol (600 ml) and 100% hydrazine hydrate (25.1 ml) was added thereto under ice-cooling with stirring. The mixture was stirred at room temperature for 1 hour and concentrated under reduced pressure. The residue was crystallized from isopropyl ether to give 39 g of 7-ethyl-2-hydrazino-5-(4-methoxyphenyl)-3H-thieno[2,3-e][1,4]diazepine as reddish brown crystals.

Reference Example 4

4-Methylcyanoacetophenone (120 g) and sulfur (24.2 g) were suspended in dimethylformamide (300 ml) and butyraldehyde (54.4 g) was added thereto. Then, triethylamine (76.3 g) was added thereto and the mixture was reacted at 70° C. for 1.5 hours with stirring. The reaction mixture was poured into ice water, extracted with ethyl acetate, washed with water and dried over anhydrous magnesium sulfate. After filtration, the filtrate was concentrated under reduced pressure to give 244 g of 2-amino-5-ethyl-3-(4-methylbenzoyl)thiophene as dark brown crystals.

Said compound (244 g) was dissolved in chloroform (1200 ml) and chloroacetyl chloride (112 g) was added thereto with stirring. The mixture was stirred at room temperature for 1 hour. The reaction mixture was washed with 5% aqueous sodium hydrogencarbonate and water, and dried over anhydrous magnesium sulfate.

After filtration, the residue obtained by concentration under reduced pressure was suspended in tetrahydrofuran (1000 ml) and sodium iodide (149 g) was added thereto. The mixture was refluxed under heating with stirring for 2 hours. The reaction mixture was cooled to −50° C. and liquid ammonia (ca. 120 ml) was added at once with stirring. The temperature of the reaction mixture was raised to room temperature over 2 hours. After removing ammonia with an aspirator, the reaction mixture was concentrated under reduced pressure and the residue was dissolved in isopropyl alcohol (1200 ml). Thereto was added acetic acid (72 g) and the mixture was allowed to react at 70° C. for 14 hours with stirring. After concentration under reduced pressure, the residue was dissolved in chloroform (1000 ml), washed with 5% aqueous sodium hydrogencarbonate and saline and dried over anhydrous magnesium sulfate. After filtration, the filtrate was concentrated under reduced pressure and the residue was purified by silica gel chromatography to give 25 g of 7-ethyl-1,3-dihydro-5-(4-methylphenyl)-thieno[2,3-e][1,4]diazepin-2-one.

The aforementioned diazepine compound (25 g) was dissolved in chloroform (300 ml) and phosphorus pentasulfide (7.5 g) was added thereto, followed by reflux under heating with stirring for 3 hours. After cooling, the mixture was washed with 5% aqueous sodium hydrogencarbonate and water and dried over anhydrous magnesium sulfate. After filtration, the filtrate was concentrated under reduced pressure to give 20 g of 7-ethyl-5-(4-methylphenyl)-1,3-dihydro-2H-thieno[2,3-e][1,4]diazepine-2-thione as orange crystals.

The thione compound (20 g) as mentioned above was suspended in methanol (100 ml) and 100% hydrazine hydrate (13.2 g) was added thereto. The mixture was stirred at room temperature for 0.5 hour. Concentration under reduced pressure gave 18.3 g of 7-ethyl-2-hydrazino-5-(4-methylphenyl)-3H-thieno[2,3-e][1,4]diazepine as red brown crystals.

Reference Example 5

2-Aminobenzophenone (25 g) was dissolved in chloroform (250 ml) and chloroacetyl chloride (17.2 g) was added thereto with stirring. The mixture was refluxed under heating for 1 hour. The reaction mixture was washed with water and dried over anhydrous magnesium sulfate. After filtration, the filtrate was concentrated under reduced pressure and the residue was suspended in tetrahydrofuran (250 ml). Thereto was added sodium iodide (28.6 g) and the mixture was refluxed under heating with stirring for 2 hours.

The reaction mixture was cooled to −50° C. and liquid ammonia (ca. 50 ml) was added at once with stirring. The temperature of the reaction mixture was raised to room temperature over 2 hours. After removing ammonia with an aspirator, the reaction mixture was distilled under reduced pressure and ethyl acetate (250 ml) was added thereto. After washing with water, the mixture was dried over magnesium sulfate. After filtration, the filtrate was concentrated under reduced pressure. The residue was dissolved in isopropyl alcohol (300 ml). Thereto was added acetic acid (9.1 g) and the mixture was refluxed under heating with stirring for 14 hours. After concentration under reduced pressure, the residue was dissolved in chloroform (300 ml), washed with 5% aqueous sodium hydrogencarbonate and saline, and dried over anhydrous magnesium sulfate. After filtration, the filtrate was concentrated under reduced pressure and ethyl acetate (100 ml) was added to the residue to allow crystallization to give 21 g of 1,3-dihydro-5-phenyl-2H-1,4-benzodiazepin-2-one as crystals.

The aforementioned diazepine compound (18 g) was dissolved in dioxane (150 ml) and phosphorus pentasulfide (6.8 g) was added thereto, followed by reflux under heating with stirring for 2 hours. After cooling, the mixture was washed with 5% aqueous sodium hydrogencarbonate and saline and dried over anhydrous magnesium sulfate. After filtration, the filtrate was concentrated under reduced pressure to give 10.6 g of 1,3-dihydro-5-phenyl-2H-1,4-benzodiazepine-2-thione.

The thione compound (5.5 g) mentioned above was suspended in methanol (50 ml) and 100% hydrazine hydrate (2.1 ml) was added thereto with stirring under ice-cooling. The mixture was stirred at room temperature for 3 hours. Concentration under reduced pressure gave 5.0 g of a hydrazono compound as an oily substance.

EXAMPLE 16

The hydrazono compound (5 g) obtained in Reference Example 3 was suspended in chloroform (100 ml) and n-dodecanoyl chloride (4.2 g) was added thereto. The mixture was stirred at room temperature for 1 hour. After washing with 5% aqueous sodium hydrogencarbonate and water, the mixture was dried over anhydrous magnesium sulfate. After filtration, the filtrate was concentrated under reduced pressure and the residue was dissolved in toluene (100 ml). Thereto was added acetic acid (1.1 ml) with stirring and the mixture was refluxed under heating with stirring for 1 hour. After cooling, the reaction mixture was washed with 5% aqueous sodium hydrogencarbonate and water, and dried over anhydrous magnesium sulfate. After filtration, the filtrate was concentrated under reduced pressure. The residue obtained was crystallized from isopropyl ether to give 7.8 g of 2-ethyl-4-(4-methoxylphenyl)-9-undecyl-6H-thieno[3,2-f][1,2,4]triazolo[4,3-a][1,4]diazepine as white crystals.

EXAMPLE 17

Anhydrous aluminum chloride (78.1 g) was suspended in dichloromethane (700 ml) and thereto was dropwise added n-butylmercaptan (106 ml) with stirring under ice-cooling. Thereto was added 2-ethyl-4-(4-methoxylphenyl)-9-undecyl-6H-thieno[3,2-f][1,2,4]triazolo[4,3-a][1,4]diazepine (40 g) obtained in Example 1 under ice-cooling. After stirring at room temperature for 20 hours, the reaction mixture was washed with 5% aqueous sodium hydrogencarbonate and water and dried over anhydrous magnesium sulfate. After filtration, the filtrate was concentrated under reduced pressure and purified by silica gel column chromatography to give 20 g of 2-ethyl-4-(4-hydroxyphenyl)-9-undecyl-6H-thieno[3,2-f][1,2,4]triazolo[4,3-a][1,4]diazepine as crystals, melting point 164.5°–166.5° C.

EXAMPLE 18

The hydrazono compound (6 g) obtained in Reference Example 4 was suspended in chloroform (50 ml) and thereto was added stearyl chloride (6.7 g). The mixture was stirred at room temperature for 1 hour. After washing with 5% aqueous sodium hydrogencarbonate and water, the mixture was dried over anhydrous magnesium sulfate. After filtration, the filtrate was concentrated under reduced pressure and the residue was dissolved in toluene (100 ml). Thereto was added acetic acid (1.25 ml) with stirring and the mixture was refluxed under heating with stirring for 1 hour. After cooling, the mixture was washed with 5% aqueous sodium hydrogencarbonate and water and dried over anhydrous magnesium sulfate. After filtration, the filtrate was concentrated under reduced pressure and the residue was purified by silica gel column chromatography. The obtained oily substance was crystallized from ethyl acetate-hexane to give 2-ethyl-9-heptadecyl-4-(4-methylphenyl)-6H-thieno[3,2-f][1,2,4]triazolo[4,3-a][1,4]diazepine as white crystals, melting point 78°–80° C.

EXAMPLE 19

The hydrazono compound (5.0 g) obtained in Reference Example 5 was suspended in chloroform (50 ml) and thereto was added n-dodecanoyl chloride (5.8 g). The mixture was stirred at room temperature for 1 hour. After washing with 5% aqueous sodium hydrogencarbonate and water, the reaction mixture was dried over anhydrous magnesium sulfate. After filtration, the filtrate was concentrated under reduced pressure and the residue was dissolved in toluene (50 ml). Thereto was added acetic acid (1.5 ml) with stirring and the mixture was refluxed under heating with stirring for 1 hour. After cooling, the mixture was washed with 5% aqueous sodium hydrogencarbonate and water and dried over anhydrous magnesium sulfate. After filtration, the filtrate was concentrated under reduced pressure and the residue was purified by silica gel column chromatography. The oily substance obtained was crystallized from hexane to give 3.4 g of 6-phenyl-1-undecyl-4H-[1,2,4]triazolo[4,3-a][1,4]benzodiazepine as white crystals, melting point 76°–77° C.

EXAMPLE 20

2-Ethyl-4-(4-methoxylphenyl)-9-undecyl-6H-thieno[3,2-f][1,2,4]triazolo[4,3-a][1,4]diazepine (8.0 g) obtained in Example 16 was suspended in water (200 ml). Thereto was added sulfuric acid (7.6 ml) and the mixture was stirred at 80° C. for 2 hours. Thereto was gradually added dropwise a solution of sodium nitrite (7.6 g) in water (25 ml) and the mixture was stirred at 80° C. for 3 hours. After cooling, potassium carbonate was added thereto to make the reaction mixture alkaline. The mixture was extracted with ethyl acetate, washed with water and dried over anhydrous magnesium sulfate. After filtration, the filtrate was concentrated under reduced pressure and the residue was purified by silica gel column chromatography to give 4.4 g of 5-ethyl-3-(4-methoxybenzoyl)-2-(3-hydroxymethyl-5-undecyl1,2,4-triazol-4-yl)thiophene as an oily substance.

EXAMPLE 21

2-Ethyl-4-(4-hydroxyphenyl)-9-undecyl-6H-thieno[3,2-f][1,2,4]triazolo[4,3-a][1,4]diazepine (20 g) obtained in Example 17 was dissolved in dioxane (300 ml). Thereto were added water (300 ml) and sulfuric acid (12 ml) and the mixture was stirred at 80° C. for 2 hours. Thereto was gradually added dropwise a solution of sodium nitrite (30 g) in water (100 ml) and the mixture was stirred at 80° C. for 3 hours. After cooling, potassium carbonate was added thereto to make the reaction mixture alkaline. The mixture was extracted with ethyl acetate, washed with water and dried over anhydrous magnesium sulfate. After filtration, the filtrate was concentrated under reduced pressure and purified by silica gel column chromatography to give 11 g of 5-ethyl-3-(4-hydroxybenzoyl)-2-(3-hydroxymethyl-5-undecyl1,2,4-triazol-4-yl)thiophene as an oily substance.

EXAMPLE 22

2-Ethyl-9-heptadecyl-4-(4-methylphenyl)-6H-thieno[3,2-f][1,2,4]triazolo[4,3-a][1,4]diazepine (6 g) obtained in Example 18 was dissolved in dioxane (60 ml). Thereto were added water (60 ml) and sulfuric acid (2.9 ml) and the mixture was stirred at 80° C. for 2 hours. A solution of sodium nitrite (7.6 g) in water (25 ml) was gradually added dropwise and the mixture was stirred at 80° C. for 3 hours. After cooling, potassium carbonate was added thereto to make the reaction mixture alkaline. The mixture was extracted with ethyl acetate, washed with water and dried over anhydrous magnesium sulfate. After filtration, the filtrate was concentrated under reduced pressure and the residue was purified by silica gel column chromatography. The oily substance obtained was crystallized from hexane to give 0.6 g of 5-ethyl-3-(4-methylbenzoyl)-2-(5-heptadecyl-3-hydroxymethyl-1,2,4-triazol-4-yl)thiophene as white crystals, melting point 68°–69° C.

EXAMPLE 23

6-phenyl-1-undecyl-4H-[1,2,4]triazolo[4,3-a][1,4]benzodiazepine (3.2 g) obtained in Example 19 was dissolved in dioxane (30 ml). Thereto were added water (30 ml) and sulfuric acid (2.1 ml) and the mixture was stirred at 60° C. for 1 hour. Thereto was gradually added dropwise a solution of sodium nitrite (5.5 g) in water (20 ml) and the mixture was stirred at 70° C. for 2 hours. After cooling, potassium carbonate was added thereto to make the reaction mixture alkaline. The mixture was extracted with ethyl acetate, washed with water and dried over anhydrous magnesium sulfate. After filtration, the filtrate was concentrated under reduced pressure and the residue was purified by silica gel column chromatography to give 0.4 g of 2-(3-hydroxymethyl-5-undecyl1,2,4-triazol-4-yl)benzophenone as an oily substance, melting point 111°–112° C.

EXAMPLE 24

5-Ethyl-3-(4-methoxybenzoyl)-2-(3-hydroxymethyl-5-undecyl-1,2,4-triazol-4-yl)thiophene (4.4 g) obtained in Example 20 was dissolved in ethanol (100 ml). Thereto was added sodium borohydride (0.16 g) with stirring and the mixture was stirred at room temperature for 1 hour. After the ethanol was distilled away, 5% aqueous sodium hydrogencarbonate was added thereto and the liberated oily substance was extracted with ethyl acetate. The extract was washed with water and dried over anhydrous magnesium sulfate. After filtration, the filtrate was concentrated under reduced pressure and toluene (100 ml) was added to the residue. The mixture was refluxed under heating with stirring and sulfuric acid was gradually added dropwise until the reaction ended. After cooling, 5% aqueous sodium hydrogencarbonate was added thereto and the mixture was extracted with ethyl acetate. The extract was washed with water and dried over anhydrous magnesium sulfate. After filtration, the residue was concentrated under reduced pressure and the residue was purified by silica gel column chromatography. The oily substance obtained was crystallized from hexane to give 1.64 g of 2-ethyl-4-(4-methoxyphenyl)-9-undecyl-4H,6H-thieno[2,3-e][1,2,4]triazolo[3,4-c][1,4]oxazepine as white crystals, melting point 91°–93° C.

EXAMPLE 25

5-Ethyl-3-(4-hydroxybenzoyl)-2-(3-hydroxymethyl-5-undecyl-1,2,4-triazol-4-yl)thiophene (11 g) obtained in Example 21 was dissolved in ethanol (60 ml). Thereto was added sodium borohydride (431 mg) with stirring and the mixture was stirred at room temperature for 1 hour. After the ethanol was distilled away, 5% aqueous sodium hydrogencarbonate was added to the residue and the liberated oily substance was extracted with ethyl acetate. The extract was washed with water and dried over anhydrous magnesium sulfate. After filtration, the filtrate was concentrated under reduced pressure and toluene (150 ml) was added to the residue. The mixture was refluxed under heating with stirring and sulfuric acid was gradually added dropwise until the reaction ended. After cooling, 5% aqueous sodium hydrogencarbonate was added thereto and the mixture was extracted with ethyl acetate. The extract was washed with water and dried over anhydrous magnesium sulfate. After filtration, the filtrate was concentrated under reduced pressure and the oily substance obtained was crystallized from isopropyl etherethyl acetate (4:1) to give 6.5 g of 2-ethyl-4-(4-hydroxyphenyl)-9-undecyl-4H,6H-thieno[2,3-e][1,2,4]triazolo[3,4-c][1,4]oxazepine as white brown crystals, melting point 96°–98° C.

EXAMPLE 26

5-Ethyl-3-(4-methylbenzoyl)-2-(5-heptadecyl-3-hydroxymethyl-1,2,4-triazol-4-yl)thiophene (3 g) obtained in Example 22 was dissolved in ethanol (30 ml). Thereto was added sodium borohydride (0.1 g) with stirring and the mixture was stirred at room temperature for 1 hour. After the ethanol was distilled away, 5% aqueous sodium hydrogencarbonate was added thereto and the liberated oily substance was extracted with ethyl acetate. The extract was washed with water and dried over anhydrous magnesium sulfate. After filtration, the filtrate was concentrated under reduced pressure and toluene (120 ml) was added to the residue. The mixture was refluxed under heating with stirring and sulfuric acid was gradually added dropwise until the reaction ended. After cooling, 5% aqueous sodium hydrogencarbonate was added thereto and the mixture was extracted with ethyl acetate. The extract was washed with water and dried over anhydrous magnesium sulfate. After filtration, the filtrate was concentrated under reduced pressure and the residue was purified by silica gel chromotography. The oily substance obtained was crystallized from hexane to give 0.9 g of 2-ethyl-9-heptadecyl-4-(4-methylphenyl-4H,6H-thieno[2,3-e][1,2,4]triazolo[3,4-c][1,4]oxazepine as white crystals, melting point 83°–84° C.

EXAMPLE 27

2-(3-Hydroxymethyl-5-undecyl1,2,4-triazol-4-yl)benzophenone (2.7 g) obtained in Example 23 was dissolved in ethanol (30 ml). Thereto was added sodium borohydride (240 mg) with stirring and the mixture was stirred at room temperature for 2 hours. After the ethanol was distilled away, 5% aqueous sodium hydrogencarbonate was added thereto and the liberated oily substance was extracted with ethyl acetate. The extract was washed with water and dried over anhydrous magnesium sulfate. After filtration, the filtrate was concentrated under reduced pressure and toluene (150 ml) was added to the residue. The mixture was refluxed under heating with stirring and sulfuric acid was gradually added dropwise until the reaction ended. After cooling, 5% aqueous sodium hydrogencarbonate was added thereto and the mixture was extracted with ethyl acetate. The extract was washed with water and dried over anhydrous magnesium sulfate. After filtration, the filtrate was concentrated under reduced pressure and the residue was purified by silica gel chromotography. The oily substance obtained was crystallized from hexane to give 1 g of 6-phenyl-1-undecyl-4H,6H-[1,2,4]triazolo[4,3-a][4,1]benzoxazepine, melting point 83°–84° C.

Reference EXAMPLE 6 phosphonium salt (141 g) obtained from n-nonyl bromide (115 ml) and triphenylphosphine (78.5 g) was dissolved in dry tetrahydrofuran (500 ml) and thereto was dropwise added n-butyl lithium (372 ml, 1.6M hexane solution) over not less than 1 hour at 0° C. After the dropwise addition, the reaction mixture was stirred at said temperature for 30 minutes and at room temperature for 1 hour. A solution of 4-nitrobenzaldehyde (45.3 g) in tetrahydrofuran (150 ml) was dropwise added thereto at 0° C. over 1 hour. The reaction mixture was stirred at room temperature for 10 hours and filtered. The residue was washed with ether. The filtrate was concentrated under reduced pressure and purified by silica gel column chromatography (hexane/ethyl acetate= 100:1) to give 70.9 g of 4-(1-decenyl)nitrobenzene (cis/trans=7:3).

A mixture of 4-(1-decenyl)nitrobenzene (12.2 g), acetic acid (120 ml) and palladium black (0.84 g) was hydrogenated at room temperature and at 3–4 atm for 12 hours. The catalyst was changed and the reaction was continued under the same conditions for 12 hours. The catalyst was filtered off and the filtrate was concentrated under reduced pressure to give 10.9 g of 4-decylaniline.

A solution of 4-decylaniline (4.50 g) in dry benzene (20 ml) was dropwise added to a solution of boron trichloride (21.2 ml, 1M methylene chloride solution) in dry benzene (10 ml) under ice-cooling. After the dropwise addition, benzonitrile (2.96 ml) and aluminum chloride (2.83 g) were added in order and the mixture was stirred at room temperature for 20 minutes, followed by reflux under heating overnight. After cooling, 2N hydrochloric acid was added thereto and the mixture was stirred at 80° C. for 30 minutes. The residue was filtered off and the filtrate was extracted with ether and dried over anhydrous magnesium sulfate. After filtration, the filtrate was concentrated under reduced pressure and the residue was purified by silica gel chromotography (hexane/ethyl acetate=:10:1) to give 2.89 g of 2-amino-5-decylbenzophenone.

Reference Example 7 phosphonium salt (141 g) obtained from n-nonyl bromide (115 ml) and triphenylphosphine (78.5 g) was dissolved in dry tetrahydrofuran (500 ml) and thereto was dropwise added n-butyl lithium (372 ml, 1.6M hexane solution) over not less than 1 hour at 0° C. After the dropwise addition, the reaction mixture was stirred at said temperature for 30 minutes and at room temperature for 1 hour, and a solution of 3-nitrobenzaldehyde (45.3 g) in tetrahydrofuran (150 ml) was dropwise added thereto at 0° C. over 1 hour. The reaction mixture was stirred at room temperature for 10 hours and filtered. The residue was washed with ether. The filtrate was concentrated under reduced pressure and purified by silica gel column chromatography (hexane/ethyl acetate= 100:1) to give 57.3 g of 3-(1-decenyl)nitrobenzene (cis/trans=7:3).

A mixture of 3-(1-decenyl)nitrobenzene (43.9 g), acetic acid (200 ml) and palladium black (2.0 g) was hydrogenated at room temperature and at atmospheric pressure for 12 hours. The catalyst was changed and the reaction was continued for 12 hours under the same conditions. The catalyst was filtered off and the residue was concentrated under reduced pressure. The residue obtained was purified by silica gel column chromatography (hexane/chloroform= 10:1→1:2) to give 7.36 g of 3-decylaniline.

A solution of 3-decylaniline (3.82 g) in dry benzene (10 ml) was dropwise added to a solution of boron trichloride (36 ml, 1M methylene chloride solution) in dry benzene (10 ml) under ice-cooling. After the dropwise addition, benzonitrile (2.51 ml) and aluminum chloride (4.80 g) were added in order and the mixture was stirred at room temperature for 2 hours, followed by reflux under heating overnight. Thereto were added boron trichloride (18 ml, 1M methylene chloride solution), benzonitrile (2.5 ml) and aluminum chloride (2.4 g) and the mixture was refluxed under heating for 16 hours. After cooling, 2N hydrochloric acid (42 ml) was added thereto and the mixture was stirred at 80° C. for 45 minutes. The residue was filtered off and the filtrate was extracted with ether and dried over anhydrous magnesium sulfate. After filtration, the filtrate was concentrated under reduced pressure and the residue was purified by silica gel chromotography (hexane/ethyl acetate=10:1) to give 4.16 g of 2-amino-4-decylbenzophenone.

EXAMPLE 28

(±)-4-Amino-6-(4-chlorophenyl)-1-methyl-4H-[1,2,4]triazolo[4,3-a][1,4]benzodiazepine (300 mg) and activated charcoal (30 mg) were suspended in anhydrous methylene chloride (2 ml). Thereto was added trichloromethyl chloroformate (0.09 ml) and the mixture was allowed to react with phosgene evolved in the reaction system, at room temperature for 1.5 hours. After the termination of the reaction, the reaction mixture was filtered through celite and 2-aminopyridine (130 mg) was added to the filtrate. The mixture was reacted at room temperature for 1 hour and concentrated under reduced pressure. The crystals obtained were recrystallized from N,N-dimethylformamide/water to give 84 mg of (±)-N-[6-(4-chlorophenyl)-1-methyl-4H-[1,2,4]triazolo[4,3-a][1,4]benzodiazepin-4-yl]-N'-(2-pyridyl)urea as colorless crystals, mp. 274°–278° C.

EXAMPLE 29

A solution of aniline (0.22 ml) in methylene chloride (3 ml) was dropwise added to a solution of oxalyl chloride (0.42 ml) in methylene chloride (8 ml) under ice-cooling over 5 minutes. The mixture was stirred at said temperature for 10 minutes, added with triethylamine (0.33 ml) and stirred for 1 hour. The reaction mixture was concentrated to dryness under reduced pressure. Methylene chloride (8 ml) was added to the residue and the mixture was ice-cooled. Thereto was dropwise added a solution of 4-amino-6-(4-chlorophenyl)-1-methyl-4H-[1,2,4]triazolo[4,3-a][1,4]benzodiazepine (208 mg) in methylene chloride (2 ml) over 5 minutes. The reaction mixture was stirred at room temperature for 2 hours. Thereto was added chloroform (5 ml) and the reaction mixture was washed with water, aqueous sodium hydrogencarbonate and water in order. The organic layer was dried over anhydrous sodium sulfate and filtered. The filtrate was concentrated to dryness and the residue was purified by silica gel chromotography (developing solvent; chroloform/methanol=50:1) and the obtained pure fraction was concentrated to dryness. The concentrate was then crystallized from a mixed solvent of ethyl acetate-ether to give 99.0 mg of (±)-N-[6-(4-chlorophenyl)-1-methyl-4H-[1,2,4]triazolo[4,3-a][1,4]benzodiazepin-4-yl]-N'-phenyloxalyldiamide as colorless needle crystals, mp. 247°–248° C.

EXAMPLE 30

Phenyl hydrazine (0.5 ml) was added to a solution of (±)-6-(4-chlorophenyl)-4-ethoxycarbonyl-1-methyl-4H-[1,2,4]triazolo[4,3-a][1,4]benzodiazepine (190 mg) in dimethyl sulfoxide (5 ml), and the mixture was stirred at 90° C. for 2 days. Thereto was added chloroform (50 ml) and the reaction mixture was washed with water, 0.3N hydrochloric acid and water in order. The chloroform layer was dried and concentrated to dryness. The residue was purified by silica gel chromotography (chroloform/methanol=30:1) and the obtained pure fraction was concentrated. Thereto was added ethyl acetate to give the objective crystals. The crystals were recrystallized from a mixed solvent of chloroform-ethyl acetate to give 134.3 mg of pure (±)-N'-phenyl-[6-(4-chlorophenyl)-1-methyl-4H-[1,2,4]triazolo[4,3-a][1,4]benzodiazepin-4-yl]carbohydrazide as colorless needle crystals, mp. 175°–177° C.

In the same manner, hydrazine (H$_2$NNH$_2$) was added to a solution of (±)-6-(4-chlorophenyl)-4-ethoxycarbonyl-1-methyl-4H-[1,2,4]triazolo[4,3-a][1,4]benzodiazepine (660 mg) in dimethylformamide (7 ml) and the mixture was reacted at room temperature for 1 hour. The mixture was extracted in the same manner as above and the residue was crystallized from chloroform-ether to give 415 mg of (±)-6-(4-chlorophenyl)-1-methyl-4H-[1,2,4]triazolo[4,3-a][1,4]benzodiazepin-4-yl]carbohydrazide as colorless needle crystals, mp. 175°–178° C.

EXAMPLE 31

Benzoyl chloride (64 ml) was added to a solution of (±)-N-[6-(4-chlorophenyl)-1-methyl-4H-[1,2,4]triazolo[4,3-a][1,4]benzodiazepin-4-yl]carbohydrazide (183 mg) in pyridine (4 ml) under ice-cooling. After stirring the mixture at said temperature for 30 minutes, water (0.1 ml) was added thereto and the mixture was stirred for 10 minutes. Pyridine was distilled away under reduced pressure and the residue was dissolved in chloroform and washed with water. The organic layer was dried, concentrated and added with ethyl acetate to give 195 mg of crystals. The crystals were recrystallized from a mixed solvent of chlorofom-ethyl acetate to give 164.4 mg of pure (±)-N'-benzoyl-[6-(4-chlorophenyl)-1-methyl-4H-[1,2,4]triazolo[4,3-a][1,4]benzodiazepin-4-yl]carbohydrazide as colorless needle crystals, mp. 243°–245° C.

EXAMPLE 32

A solution of (±)-[6-(4-chlorophenyl)-1-methyl-4H-[1,2,4]triazolo[4,3-a][1,4]benzodiazepin-4-yl]carbohydrazide (109.7 mg) in dimethylformamide (1 ml) was cooled to –40° C. and 4N dioxane hydrochloride (0.23 ml) was added thereto. The temperature of the mixture was raised to 0° C. The reaction mixture was cooled again to –40° C. and isopentyl nitrite (40 µl) was added thereto. The mixture was stirred at –30° C. for 1 hour. The temperature of the mixture was again cooled to –70° C. Triethylamine (0.125 ml) was added to the mixture and 10 minutes later, benzyl amine (77 µl) was added thereto. Then, the temperature of the mixture was raised to 0° C. and the mixture was stirred for 3 hours. The mixture was stirred at room temperature for 10 hours. Dimethylformamide was distilled away under reduced pressure and the residue obtained was dissolved in chloroform and washed with 0.3N hydrochloric acid, an aqueous solution of sodium bicarbonate and water in order and dried over anhydrous sodium sulfate. Chloroform was distilled away under reduced pressure and ethyl acetate was added to the residue to give 95.1 mg of (±)-N-benzyl-[6-(4-chlorophenyl)-1-methyl-4H-[1,2,4]triazolo[4,3-a][1,4]-benzodiazepin-4-yl]carboxamide as colorless needle crystals, mp. 265°–267° C.

In the same manner, (±)-O-benzyl-N-[6-(4-chlorophenyl)-1-methyl-4H-[1,2,4]triazolo[4,3-a][1,4]benzodiazepin-4-yl]carbohydroxamate was synthesized, mp. 138°–139° C.

EXAMPLE 33

In a nitrogen atmosphere, 4-amino-6-(4-chlorophenyl)-4-ethoxycarbonyl-1-methyl-4H-[1,2,4]triazolo[4,3-a][1,4]-benzodiazepine (373 mg) was dissolved in dry tetrahydrofuran (4 ml) and thereto was added 3-methylphenyl isocyanate (139 μl), followed by reaction at room temperature for 3.5 hours. After the completion of the reaction, water was added to the reaction mixture and the mixture was extracted with ethyl acetate. The organic layer was washed with a 5% aqueous solution of citric acid, water and saturated brine, and dried over anhydrous magnesium sulfate. The residue was concentrated under reduced pressure. The concentrate was purified by silica gel column chromatography (chroloform:methanol=45:1) and crystallized to give 219 mg of N-[6-(4-chlorophenyl)-4-ethoxycarbonyl-1-methyl-4H-[1,2,4]triazolo[4,3-a][1,4]benzodiazepin-4-yl]-N'-(3-methylphenyl)urea as pale yellow needle crystals, mp. 168°–172° C.

EXAMPLE 34

In a nitrogen atmosphere, N-[6-(4-chlorophenyl)-4-ethoxycarbonyl-1-methyl-4H-[1,2,4]triazolo[4,3-a][1,4]-benzodiazepin-4-yl]-N'-(3-methylphenyl)urea dissolved in anhydrous tetrahydrofuran (2 ml) was dropwise added to a suspension of 60% sodium hydride (10 mg) in anhydrous tetrahydrofuran (1 ml) at room temperature and the mixture was refluxed under heating for 30 minutes. After the reaction mixture was cooled, water was added thereto and the mixture was extracted with ethyl acetate. The organic layer was washed with a 5% aqueous solution of citric acid, water and saturated brine and dried over anhydrous magnesium sulfate. The residue was concentrated under reduced pressure. The concentrate was recrystallized from ether-ethyl acetate to give 37 mg of 6-(4-chlorophenyl)-1-methyl-4H-[1,2,4] triazolo[4,3-a][1,4]benzodiazepine-4-spiro-5'-[3'-(3-methylphenyl)-2',4'-dioxoimidazolidine] as colorless needle crystals, mp. 269°–271° C.

EXAMPLE 35

6-(4-Chlorophenyl)-1-undecyl-4H-[1,2,4]triazolo[4,3-a] [1,4]benzodiazepine (1.23 g) was dissolved in dichloromethane (10 ml) and acetic acid (5 ml) and zinc powder (540 mg) were added thereto with stirring. After stirring at room temperature for 6 hours, the mixture was washed with 5% aqueous sodium hydrogencarbonate and water. The reaction mixture was dried over anhydrous magnesium sulfate. After filtration, the filtrate was concentrated under reduced pressure. The residue was purified by silica gel column chromatography and the oily substance obtained was crystallized from ethyl acetate to give 320 mg of 6-(4-chlorophenyl)-1-undecyl-4H,5H,6H-[1,2,4]triazolo[4,3-a][1,4]benzodiazepine, mp. 94°–95° C.

EXAMPLE 36

2-Amino-4-decylbenzophenone (4.16 g) was dissolved in chloroform (40 ml) and phthaloylalanyl chloride (3.22 g) was added thereto with stirring at room temperature. The mixture was stirred for 0.5 hour. The reaction mixture was washed with 5% aqueous sodium hydrogencarbonate and water and dried over anhydrous magnesium sulfate. After filtration, the filtrate was concentrated under reduced pressure. The concentrate was purified by silica gel column chromatography and the oily substance obtained was dissolved in a mixed solvent of methanol (20 ml) and tetrahydrofuran (40 ml). Thereto was added hydrazine monohydrate (1.56 g) with stirring under ice-cooling and the mixture was stirred for 2 hours. Conc. hydrochloric acid (1 ml) was added thereto with stirring at room temperature and the mixture was stirred at 60° C. for 2 hours. After cooling, the mixture was concentrated under reduced pressure and the residue was extracted with chloroform and washed with 5% aqueous sodium hydrogencarbonate and water. The residue was dried over anhydrous sodium sulfate. After filtration, the filtrate was concentrated under reduced pressure. Isopropyl alcohol (60 ml) and acetic acid (1 ml) were added to the concentrate and the mixture was stirred at 70° C. for 1 hour. After cooling, the residue obtained by concentration under reduced pressure was extracted with chloroform and washed with 5% aqueous sodium hydrogencarbonate and water. The extract was dried over anhydrous sodium sulfate. After filtration, the filtrate was concentrated under reduced pressure and purified by silica gel column chromatography to give 3.2 g of 8-decyl-1,3-dihydro-3-methyl-5-phenyl-2H-1, 4-benzodiazepin-2-one as crystals.

The thione compound (2.8 g) as mentioned above was suspended in methanol (30 ml) and hydrazine monohydrate (400 μl) was added thereto with stirring at room temperature. The mixture was stirred at room temperature for 1 hour. After concentration under reduced pressure, the residue was dissolved in chloroform, washed with water and dried over anhydrous magnesium sulfate. After filtration, the filtrate was concentrated under reduced pressure and purified by silica gel column chromatography to give 1.9 g of a hydrazono compound as an oily substance.

The hydrazono compound (1.9 g) obtained was suspended in toluene (20 ml) and thereto was added triethyl orthoacetate (1.6 g). The mixture was refluxed under heating for 16 hours. After cooling, the mixture was extracted with ethyl acetate, washed with 5% aqueous sodium hydrogencarbonate and water and dried over anhydrous magnesium sulfate. After filtration, the filtrate was concentrated under reduced pressure and purified by silica gel column chromatography. The oily substance obtained was crystallized from isopropyl ether to give 0.3 g of 9-decyl-1,4-dimethyl-6-phenyl-4H-[1, 2,4]triazolo[4,3-a][1,4]benzodiazepine, mp. 111°–112° C.

The formulation examples of the preparation of the present invention are given in the following.

(1) Tablet

The above-mentioned compound (I) (0.5 part), lactose (25 parts), crystalline cellulose (35 parts) and corn starch (3 parts) are thoroughly mixed and kneaded well with a binder prepared from corn starch (2 parts). The kneaded composition is passed through a 16-mesh sieve, dried in an oven at 50° C. and passed through a 24-mesh sieve. The obtained kneaded powder, corn starch (8 parts), crystalline cellulose (11 parts) and talc (9 parts) are thoroughly mixed and compressed to give tablets containing 0.5 mg of an active ingredient per tablet.

(2) 1% Powder

The above-mentioned compound (I) (1 part) and lactose (90 parts) are thoroughly mixed and kneaded well with a binder prepared from a suitable amount of methylcellulose. The kneaded composition is passed through a 16-mesh sieve and dried in an oven at 50° C. The dry granule was press passed through a 32-mesh sieve and mixed well with a suitable amount of silicon dioxide to give a 1% powder.

We claim:

1. A method for treating osteoporosis comprising administering an azepine compound or a pharmaceutically acceptable salt thereof of the formula

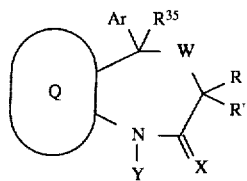

wherein

Ar is phenyl;

X and Y combinedly form =N—N=C(R⁶)— or =N—N(R⁵)—CO— wherein R⁵ and R⁶ are each hydrogen, halogen, alkyl, alkenyl, alkynyl, cycloalkyl, cycloalkylalkyl, aryl, aralkyl, aryloxyalkyl, —(CH₂)aCOOR⁷ wherein a is an integer of 1 to 6 and R⁷ is hydrogen, alkyl, alkenyl or aralkyl, or —(CH₂)aNHCOR⁴³ wherein a is an integer of 1 to 6 and R⁴³ is alkyl or aralkyl;

W is —N(R³⁶)— wherein R³⁶ is hydrogen or forms a bond with R³⁵;

R³⁵ is hydrogen or forms a bond with

R is hydrogen, alkyl, haloalkyl, aryl, heteroaryl, aralkyl, heteroarylalkyl or a group of a formula selected from the group consisting of:

—(CH₂)bN(R⁸)(R⁹)   (1)

—(CH₂)bOR¹⁰   (2)

$$-(CH_2)bN(R^{10})\overset{\overset{Z}{\|}}{C}N(R^{11})(R^{12})$$   (3)

—(CH₂)bN(R¹⁰)CORa¹¹   (4)

—(CH₂)bN(R¹⁰)SO₂R⁴⁴   (5)

—(CH₂)bN(R¹⁰)COOR⁴⁵   (6)

$$-(CH_2)bO\overset{\overset{Z}{\|}}{C}N(R^{11})(R^{12})$$   (7)

—(CH₂)bOCOR⁴⁶   (8)

—(CH₂)bCON(R⁴⁷)(R⁴⁸)   (9)

—(CH₂)bOSO₂R⁴⁴   (10)

—(CH₂)bCOR⁴⁹   (11)

—(CH₂)bS(O)nR¹¹   (12)

—CON(R¹⁰)OR⁸   (13)

$$-CON(R^{10})N(R^{10})\overset{\overset{Z}{\|}}{C}Ra^{11}$$   (14)

—CON(R¹⁰)N(R¹⁰)SO₂Ra¹¹   (15)

$$-N(R^{10})\overset{\overset{Z}{\|}}{C}N(R^{10})CORa^{11}$$   (16)

$$-(R^{10})\overset{\overset{Z}{\|}}{C}N(R^{10})SO_2Ra^{11}$$   (17)

—CON(R¹⁰)N(R¹⁰)(R¹¹)   (18)

—(CH₂)bN(R¹⁰)COCON(R¹¹)(R¹²)   (19)

and

—(CH₂)aCOOR¹   (20)

wherein b is 0 or an integer of 1 to 6, Z is an oxygen atom or sulfur atom, R⁸ and R⁹ are the same or different and each is hydrogen, alkyl, aryl or aralkyl, R¹⁰ is hydrogen, alkyl or aralkyl, R¹¹ and R¹² are the same or different and each is hydrogen, alkyl, cycloalkyl, cycloalkylalkyl, aryl, aralkyl, heteroaryl or heteroarylalkyl, Ra¹¹ is alkyl, cycloalkyl, cycloalkylalkyl, aryl, aralkyl, heteroaryl or heteroarylalkyl, R⁴⁴ is alkyl, aryl, aralkyl, cycloalkyl or heteroaryl, R⁴⁵ is alkyl, aryl or aralkyl, R⁴⁶ is alkyl, alkenyl, alkynyl, cycloalkyl, cycloalkylalkyl, aryl, aralkyl, heteroaryl or heteroarylalkyl, R⁴⁷ and R⁴⁸ are the same or different and each is hydrogen, alkyl, acyl, aryl or aralkyl, R⁴⁹ is alkyl, aryl, aralkyl, heteroaryl or heteroarylalkyl, n is 0, 1 or 2, a is an integer of 1 to 6 and R¹ is hydrogen, alkyl, aryl or aralkyl;

R' is hydrogen or —COOR⁸ wherein R⁸ is hydrogen, alkyl, aryl or aralkyl, ring Q is a ring selected from

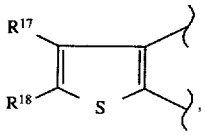

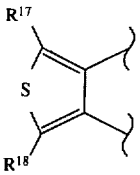

and

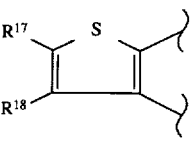

R¹⁷ and R¹⁸ are the same or different and each is hydrogen, halogen, alkyl, alkenyl, alkynyl, haloalkyl, alkoxy, nitro, amino, amino substituted by alkyl, cyclic amino selected from the group consisting of pyrrolidinyl, piperidino, morpholino, thiomorpholino and piperazinyl in each of which the nitrogen atom may be substituted by alkyl or aralkyl, hydroxy, acyloxy, cyano, carbamoyl, carbamoyl substituted by alkyl, cyclic aminocarbonyl, carboxyl, alkoxycarbonyl, aralkyloxycarbonyl, cycloalkyl, alkylcarbonyl, a group of the formula

R¹⁹—A— wherein

A is alkylene, alkenylene or alkynylene each of which may be substituted by 1 to 3 hydroxys and R¹⁹ is alkoxy, nitro, amino, hydroxy, acyloxy, cyano, carboxyl, alkoxycarbonyl, aralkyloxycarbonyl, phenyl optionally substituted by 1 to 3 substituents selected from the group consisting of halogen, hydroxy, alkyl, alkoxy, aryl, aryloxy, aralkyl, aralkyloxy, alkenyl having 2 to 18 carbon atoms which may be substituted by 1 to 3 hydroxys, alkynyl having 2 to 18 carbon atoms which may be substituted by 1 to 3 hydroxys, aralkenyl having an alkenyl moiety having 2 to 18 carbon atoms which may be substituted by 1 to 3 hydroxys and aralkynyl having an alkynyl moiety having 2 to 18 carbon atoms which may be substituted by 1 to 3 hydroxys, a group of the formula $(R^{20})(R^{21})NCO-$ or $(R^{20})(R^{21})N-SO_2-$ wherein $R^{20}$ and $R^{21}$ are the same or different and each is hydrogen, aryl, aralkyl or straight- or branched chain alkyl, alkenyl or alkynyl wherein the alkyl, alkenyl and alkynyl may be substituted by halogen, hydroxy, nitro or amino or $R^{20}$ and $R^{21}$ may, together with the adjacent nitrogen atom, form a 3 to 7-membered ring which may be substituted by straight- or branched chain alkyl and may have, in the ring, nitrogen, oxygen or sulfur atom as a hetero atom (the additional nitrogen atom may be substituted by straight- or branched chain alkyl having to 1 to 4 carbon atoms, aralkyl or diarylalkyl), a group of the formula $(R^{22})(R^{23})N-$ wherein $R^{22}$ and $R^{23}$ are the same or different and each is hydrogen, straight- or branched chain alkyl, alkenyl or alkynyl wherein the alkyl, alkenyl and alkynyl may be substituted by halogen, hydroxy, amino, alkylamino, dialkylamino, cyclic amino selected from the group consisting of pyrrolidinyl, piperidino, morpholino, thiomorpholino and piperazinyl in each of which the nitrogen atom may be substituted by alkyl or aralkyl, or C-bonded heterocyclic group (carbons may be interrupted by nitrogen, oxygen or sulfur atom), straight- or branched chain alkylcarbonyl which may be mono- or di-substituted by hydroxy, halogen, amino, alkylamino, dialkylamino, cyclic amino selected from the group consisting of pyrrolidinyl, piperidino, morpholino, thiomorpholino and piperazinyl in each of which the nitrogen atom may be substituted by alkyl or aralkyl, or straight- or branched chain alkyl (this alkyl may be substituted by halogen or hydroxy), arylcarbonyl, arylsulfonyl, alkylsulfonyl, or $R^{22}$ and $R^{23}$ may form, together with the adjacent nitrogen atom, a saturated or unsaturated 3 to 7-membered ring which may be substituted by straight- or branched chain alkyl and may have, in the ring, nitrogen, oxygen or sulfur atom as a hetero atom (each additional nitrogen atom may be substituted by straight- or branched chain alkyl), a group of the formula

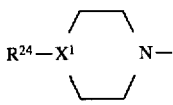

wherein $R^{24}$ is aryl, aralkyl, arylcarbonyl, a group of the formula

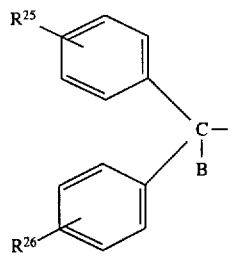

wherein $R^{25}$ and $R^{26}$ are the same or different and each is hydrogen, halogen, haloalkyl, amino, nitro, cyano, hydroxy, alkyl or alkoxy and B is hydrogen, hydroxy or esterified hydroxy, or alkyl having hydroxy and/or carbonyl and $X^1$ is CH or nitrogen atom, or a group of the formula

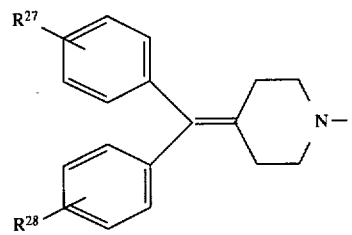

wherein $R^{27}$ and $R^{28}$ are the same or different and each is hydrogen, halogen, haloalkyl, amino, nitro, cyano, hydroxy, alkyl or alkoxy, a group of the formula $R^{29}-(CH_2)d-C\equiv C-$ wherein $R^{29}$ is aryl or optionally hydrogenated heteroaryl and d is 0, 1 or 2, a group of the formula $R^{29}-O-(CH_2)e-C\equiv C-$ wherein $R^{29}$ is as defined above and e is 1 or 2, or a group of the formula

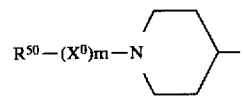

wherein $X^0$ is $-OCO-$, $-CO-$ or $-N(R^{51})CO-$ where $R^{51}$ is hydrogen or alkyl, m is 0 or 1, $R^{50}$ is alkyl, alkynyl, 2-phenylethynyl, 2-thienylsulfonyl, $-(CH_2)aCN$ where a is an integer of 1 to 6, $-(CH_2)b-R^{52}$ where b is 0 or an integer of 1 to 6 and $R^{52}$ is cycloalkyl, morpholino, thienyl, alkoxy, aryl, imidazolyl or tetrahydropyranyl or $SO_2N(R^{53})(R^{54})$ where $R^{53}$ and $R^{54}$ are the same or different and each is hydrogen, alkyl, or $R^{53}$ and $R^{54}$, with the adjacent nitrogen atom, form a heterocycle, or adjacent $R^{17}$ and $R^{18}$ may combinedly form a saturated or unsaturated 5, 6 or 7-membered ring which is condensed to a thiophene ring, said ring being optionally substituted by a substituent $Ra^{30}$ selected from hydrogen, halogen, alkyl, a group of the formula $R^{19}-A-$ wherein each symbol is as defined above and a group of the formula $(R^{20})(R^{21})NCO-$ or $(R^{20})(R^{21})N-SO_2-$ wherein each symbol is as defined above, or $R^{17}$ and $R^{18}$ may combinedly form a 5, 6 or 7-membered hetero ring which may have oxygen, sulfur or $-N(Rb^{30})-$ as a hetero atom;

$Rb^{30}$ is hydrogen, alkyl, alkenyl, alkynyl, cycloalkyl, alkoxycarbonyl, alkanoyl, aroyl, cycloalkylcarbonyl, cycloalkoxycarbonyl, cycloalkylalkylcarbonyl, cycloalkylalkoxycarbonyl, cycloalkylaminocarbonyl, a group of the formula $R^{19}-A-$ wherein each symbol is as defined above, a group of the formula $(R^{20})(R^{21})NCO-$ wherein each symbol is as defined above, a group of the formula $(R^{20})(R^{21})N-SO_2-$ wherein each symbol is as defined above, a group of the formula $Ra^{31}-SO_2-$ wherein $Ra^{31}$ is alkyl, phenyl, phenyl substituted by halogen, alkyl, alkoxy, carboxy, alkylsulfonyl, alkylthio, haloalkyl or optionally substituted phenoxy, heteroaryl or naphthyl, a group of the formula

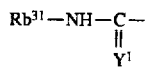

wherein $Y^1$ is oxygen atom or sulfur atom and $Rb^{31}$ is alkenyl, alkyl, cycloalkyl, aryl, aralkyl, heteroaryl, heteroarylalkyl, phenyl substituted by 1 to 3 substituents selected from alkyl, alkoxy, aryloxy, alkylsulfonyl, halogen and haloalkyl, quinolyl or sulfonyl substituted by phenyl, heteroaryl or naphthyl, or a group of the formula

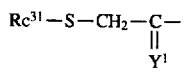

wherein $Y^1$ is oxygen atom or sulfur atom and $Rc^{31}$ is alkyl, phenyl substituted by phenyl, halogen, alkyl, alkoxy, haloalkyl or phenoxy, or heteroaryl;

in the above definitions, phenyl, aryl, aryloxy, aryloxyalkyl, arylcarbonyl, arylsulfonyl, aralkyl, aralkyloxy, aralkyloxycarbonyl, aralkenyl, aralkynyl, diarylalkyl, heteroaryl and heteroarylalkyl may have, on the ring, 1 to 3 substituents selected from halogen, alkyl, alkoxy, haloalkyl, hydroxy, nitro, amino, cyano and acyloxy; cycloalkyl of cycloalkyl, cycloalkylalkyl, cycloalkylcarbonyl, cycloalkylalkylcarbonyl, cycloalkoxycarbonyl, cycloalkylalkoxycarbonyl and cycloalkylaminocarbonyl may have 1 to 3 substituents selected from halogen, alkyl, alkoxy, haloalkoxy and aryl.

2. The method for treating osteoporosis according to claim 1, comprising administering a compound of the formula (I) wherein W is $-(NR^{36})-$ where $R^{36}$ forms a bond with $R^{35}$, or a pharmaceutically acceptable salt thereof.

3. The method for treating osteoporosis according to claim 1, comprising administering a compound of the formula (I) wherein W is $-N(R^{36})-$ where $R^{36}$ forms a bond with $R^{35}$ and X and Y combinedly form $=N-N=C(R^6)-$ where $R^6$ is as defined in claim 1, or a pharmaceutically acceptable salt thereof.

4. The method for treating osteoporosis according to claim 1, comprising administering a compound of the formula (I) wherein W is $-N(N^{36})-$ where $R^{36}$ forms a bond with $R^{35}$ and X and Y combinedly form $=N-N=C(R^{6'})-$ where $R^{6'}$ is alkyl having 6 to 20 carbon atoms, or a pharmaceutically acceptable salt thereof.

5. The method for treating osteoporosis according to claim 1, comprising administering a compound of the formula (I) wherein W is $-N(R^{36})-$ where $R^{36}$ forms a bond with $R^{35}$, R is alkyl, aryl, heteroaryl, aralkyl, heteroarylalkyl or a group of a formula selected from the group consisting of:

 (1)

 (2)

 (3)

 (4)

 (5)

 (6)

 (7)

 (8)

 (9)

 (10)

 (11)

 (12)

 (13)

 (14)

 (15)

 (16)

 (17)

 (18)

 (19)

and $-(CH_2)aCOOR^1$ (20)

wherein each symbol is as defined in claim 1 and the ring Q is a group of the formula

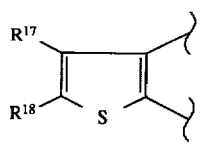

wherein each symbol is as defined in claim 1, or a pharmaceutically acceptable salt thereof.

6. The method for treating osteoporosis according to claim 1, comprising administering a compound of the formula (I) wherein is $-(NR^{36})-$ wherein $R^{36}$ forms a bond with $R^{35}$, R is alkyl, aryl, aralkyl or a group of a formula selected from the group consisting of:

 (1)

$$-(CH_2)bN(R^{10})\overset{Z}{\overset{\|}{C}}N(R^{11})(R^{12}) \quad (3)$$

$$-(CH_2)bN(R^{10})CORa^{11} \quad (4)$$

$$-(CH_2)bN(R^{10})SO_2R^{44} \quad (5)$$

$$-(CH_2)bN(R^{10})COOR^{45} \quad (6)$$

$$-(CH_2)bO\overset{Z}{\overset{\|}{C}}N(R^{11})(R^{12}) \quad (7)$$

$$-(CH_2)bCON(R^{47})(R^{48}) \quad (9)$$

$$-(CH_2)bOSO_2R^{44} \quad (10)$$

$$-(CH_2)bCOR^{49} \quad (11)$$

and $$-(CH_2)aCOOR^1 \quad (20)$$

wherein each symbol is as defined in claim 1 and the ring Q is a group of the formula

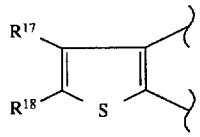

wherein each symbol is as defined in claim 1, or a pharmaceutically acceptable salt thereof.

7. The method for treating osteoporosis according to claim 1, comprising administering a compound of the formula (I) which selected from the group consisting of:
9-tert-butyl-4-(2-chlorophenyl)-2-(2-(4-isobutylphenyl)ethyl)-6-methyl-6H-thieno[3,2-f][1,2,4]triazolo[4,3-a][1,4]-diazepine,
3-[4-(2-chlorophenyl)-6,9-dimethyl-6H-thieno[3,2-f]-[1,2,4]triazolo[4,3-a][1,4]diazepin-2-yl]propionic morpholide,
4-(2-chlorophenyl)-6,9-dimethyl-2-(3-morpholinopropyl)-6H-thieno[3,2-f][1,2,4]triazolo[4,3-a][1,4]diazepine,
4-(2-chlorophenyl)-2-(2-(4-isobutylphenyl)ethyl)-9-methyl-6-propyl-6H-thieno[3,2-f][1,2,4]triazolo[4,3-a][1,4]diazepine,
4-(2-chlorophenyl)-6-isobutyl-2-(2-(4-isobutylphenyl)ethyl)-9-methyl-6H-thieno[3,2-f][1,2,4]triazolo[4,3-a][1,4]diazepine,
4-(2-chlorophenyl)-2-(2-(4-isobutylphenyl)ethyl)-9-methyl-6-phenyl-6H-thieno[3,2-f][1,2,4]triazolo[4,3-a][1,4]diazepine,
6-benzyl-4-(2-chlorophenyl)-2-(2-(4-isobutylphenyl)ethyl)-9-methyl-6H-thieno[3,2-f][1,2,4]triazolo[4,3-a][1,4]diazepine,
N-(4-(2-chlorophenyl)-2-ethyl-9-methyl-6H-thieno[3,2-f]-[1,2,4]triazolo[4,3-a][1,4]diazepin-6-yl)-2-indolecarboxamide,
N-(4-(2-chlorophenyl)-2-ethyl-9-methyl-6H-thieno[3,2-f]-[1,2,4]triazolo[4,3-a][1,4]diazepin-6-yl)-3-indoleacetamide,
6-benzoylamino-4-(2-chlorophenyl)-2-ethyl-9-methyl-6H-thieno[3,2-f][1,2,4]triazolo[4,3-a][1,4]diazepine,
4-(2-chlorophenyl)-2-ethyl-9-methyl-6-(3-(3-tolyl)ureido)-6H-thieno[3,2-f][1,2,4]triazolo[4,3-a][1,4]diazepine,
8S-(+)-6-(2-chlorophenyl)-3-cyclopropanecarbonyl-8,11-dimethyl-2,3,4,5-tetrahydro-8H-pyrido[4',3':4,5]thieno[3,2-f]-[1,2,4]triazolo[4,3-a][1,4]diazepine,
6-(2-chlorophenyl)-8,9-dihydro1,4-dimethyl-8-morpholinocarbonyl-4H,7H-cyclopenta[4,5]thieno[3,2-f][1,2,4]triazolo-[4,3-a][1,4]diazepine,
(4-(4-chlorophenyl)-2-ethyl-9-methyl-6H-thieno[3,2-f]-[1,2,4]triazolo[4,3-a][1,4]diazepin-6-yl)acetic acid,
N-(2-methoxyphenyl)-(4-(4-chlorophenyl)-2-ethyl-9-methyl-6H-thieno[3,2-f][1,2,4]triazolo[4,3-a][1,4]diazepin-6-yl)acetamide,
N-phenyl-(4-(4-chlorophenyl)-2-ethyl-9-methyl-6H-thieno[3,2-f][1,2,4]triazolo[4,3-a][1,4]diazepin-6-yl)acetamide,
N-(4-(4-chlorophenyl)-2-ethyl-9-methyl-6H-thieno[3,2-f]-[1,2,4]triazolo[4,3-a][1,4]diazepin-6-yl)-p-toluenesulfonamide,
(4-(4-methoxyphenyl)-2-ethyl-9-methyl-6H-thieno[3,2-f]-[1,2,4]triazolo[4,3-a][1,4]diazepin-6-yl)-N-(3-methylphenyl)carbamate,
4-(2-chlorophenyl)-2-ethyl-9-methyl-6-phenylacetylamino-6H-thieno[3,2-f][1,2,4]triazolo[4,3-a][1,4]diazepine,
N-(4-chlorophenyl)-N'-(4-(4-chlorophenyl)-2-ethyl-9-methyl-6H-thieno[3,2-f][1,2,4]triazolo[4,3-a][1,4]diazepin-6-yl)urea,
N-(4-(4-chlorophenyl)-2-ethyl-9-methyl-6H-thieno[3,2-f]-[1,2,4]triazolo[4,3-a][1,4]diazepin-6-yl)-N'-(3-methoxyphenyl)urea,
N-(4-(4-chlorophenyl)-2-hexyl-9-methyl-6H-thieno[3,2-f]-[1,2,4]triazolo[4,3-a][1,4]diazepin-6-yl)-N'-(3-methylphenyl)urea,
N-(4-(2-chlorophenyl)-2,3,9-trimethyl-6H-thieno[3,2-f]-[1,2,4]triazolo[4,3-a][1,4]diazepin-6-yl)-N'-(3-methylphenyl)urea,
N-(4-(2-chlorophenyl)-9-cyclohexyl-2-ethyl-6H-thieno-[3,2-f][1,2,4]triazolo[4,3-a][1,4]diazepin-6-yl)-N'-(3-methoxyphenyl)urea,
N-(2-ethyl-9-methyl-4-(4-methylphenyl)-6H-thieno[3,2-f]-[1,2,4]triazolo[4,3-a][1,4]diazepin-6-yl)-N'-(3-methylphenyl)urea,
N-(4-(2-chlorophenyl)-2-ethyl-9-methyl-6H-thieno[3,2-f]-[1,2,4]triazolo[4,3-a][1,4]diazepin-6-yl)-N'-phenylurea,
N-(2-ethyl-9-methyl-4-phenyl-6H-thieno[3,2-f][1,2,4]triazolo[4,3-a][1,4]diazepin-6-yl)-N'-(3-methylphenyl)urea,
N-(4-(4-chlorophenyl)-2-ethyl-9-methyl-6H-thieno[3,2-f]-[1,2,4]triazolo[4,3-a][1,4]diazepin-6-yl)-N'-(2-methoxyphenyl)urea,
N-(4-(2-chlorophenyl)-2-ethyl-9-methyl-6H-thieno[3,2-f]-1,2,4]triazolo[4,3-a][1,4]diazepin-6-yl)-N'-phenylthiourea,
N-(2-butyl-4-(4-chlorophenyl)-9-methyl-6H-thieno[3,2-f]-[1,2,4]triazolo[4,3-a][1,4]diazepin-6-yl)-N'-(3-methylphenyl)urea,
N-(4-(2-chlorophenyl)-2-ethyl-9-cyclohexyl-6H-thieno-[3,2-f][1,2,4]triazolo[4,3-a][1,4]diazepin-6-yl)-N'-(2-methylphenyl)urea,
4-(4-chlorophenyl)-2-ethyl-9-methyl-6-(3-phenylpropyl)-6H-thieno[3,2-f][1,2,4]triazolo[4,3-a][1,4]diazepine,
or a pharmaceutically acceptable salt thereof.

* * * * *